United States Patent
Lachia et al.

(10) Patent No.: US 9,751,867 B2
(45) Date of Patent: Sep. 5, 2017

(54) PLANT GROWTH REGULATING COMPOUNDS

(71) Applicant: Syngenta Participations AG, Basel (CH)

(72) Inventors: Mathilde Denise Lachia, Stein (CH); Claudio Screpanti, Stein (CH); Alain De Mesmaeker, Stein (CH); Alexandre Franco Jean Camille Lumbroso, Stein (CN); Stefano Rendine, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/121,074

(22) PCT Filed: Feb. 24, 2015

(86) PCT No.: PCT/EP2015/053826
§ 371 (c)(1),
(2) Date: Aug. 24, 2016

(87) PCT Pub. No.: WO2015/128321
PCT Pub. Date: Sep. 3, 2015

(65) Prior Publication Data
US 2016/0368900 A1  Dec. 22, 2016

(30) Foreign Application Priority Data
Feb. 26, 2014  (GB) .................................. 1403334.4

(51) Int. Cl.
| | | |
|---|---|---|
| *C07D 403/12* | (2006.01) | |
| *C07D 403/14* | (2006.01) | |
| *C07D 403/04* | (2006.01) | |
| *C07D 401/12* | (2006.01) | |
| *C07D 409/04* | (2006.01) | |
| *C07D 409/14* | (2006.01) | |
| *C07D 417/14* | (2006.01) | |
| *C07D 207/36* | (2006.01) | |
| *C07D 207/38* | (2006.01) | |
| *A01N 43/38* | (2006.01) | |
| *A01N 43/40* | (2006.01) | |
| *C07D 405/12* | (2006.01) | |
| *A01N 43/36* | (2006.01) | |
| *A01N 43/54* | (2006.01) | |
| *A01N 43/60* | (2006.01) | |
| *A01N 43/78* | (2006.01) | |
| *A01N 47/16* | (2006.01) | |

(52) U.S. Cl.
CPC .......... *C07D 403/12* (2013.01); *A01N 43/36* (2013.01); *A01N 43/38* (2013.01); *A01N 43/40* (2013.01); *A01N 43/54* (2013.01); *A01N 43/60* (2013.01); *A01N 43/78* (2013.01); *A01N 47/16* (2013.01); *C07D 207/36* (2013.01); *C07D 207/38* (2013.01); *C07D 401/12* (2013.01); *C07D 403/04* (2013.01); *C07D 403/14* (2013.01); *C07D 405/12* (2013.01); *C07D 409/04* (2013.01); *C07D 409/14* (2013.01); *C07D 417/14* (2013.01)

(58) Field of Classification Search
CPC .. C07D 403/14; C07D 403/12; C07D 403/04; C07D 401/12; C07D 405/12; C07D 409/04; C07D 409/14; C07D 417/14; C07D 207/36; C07D 207/38; A01N 47/16; A01N 43/40; A01N 43/54; A01N 43/38; A01N 43/78; A01N 43/60
See application file for complete search history.

(56) References Cited

FOREIGN PATENT DOCUMENTS

| WO | 2005/077177 A2 | 8/2005 |
| WO | 2006/098626 A2 | 9/2006 |
| WO | 2009/138655 A2 | 11/2009 |
| WO | 2010/125065 A2 | 11/2010 |
| WO | 2012/080115 A1 | 6/2012 |
| WO | 2013/139949 A1 | 9/2013 |
| WO | 2013/171092 A1 | 11/2013 |
| WO | 2013/174846 A1 | 11/2013 |
| WO | 2014/131843 A1 | 9/2014 |

OTHER PUBLICATIONS

International Search Report and Written Opinion for International Patent Application No. PCT/EP2015/053826 dated Mar. 23, 2015.

(Continued)

*Primary Examiner* — Sun Jae Yoo
(74) *Attorney, Agent, or Firm* — R. Kody Jones

(57) ABSTRACT

The present invention relates to novel heterocyclic derivatives of Formula (I), to processes and intermediates for preparing them, to plant growth regulator and seed germination promoting compositions comprising them and to methods of using them for controlling the growth of plants and/or promoting the germination of seeds.

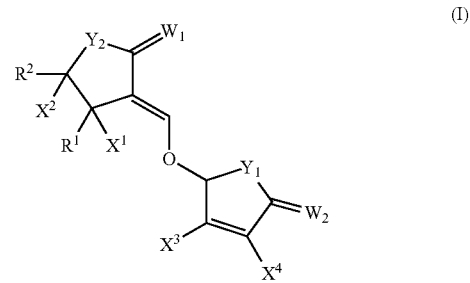

13 Claims, No Drawings

(56) References Cited

OTHER PUBLICATIONS

Johnson A W et al: "The Preparation of Synthetic Analogues of Strigol", Journal of the Chemical Society, Perkin Transactions I, Royal Society of Chemistry, GB, No. 6, Jan. 1, 1981 (Jan. 1, 1981), pp. 1734-1743.

M. Sortino et al: "Antifungal, cytotoxic and SAR studies of a series of N-alkyl, N-aryl and N-alkylphenyl-1,4-pyrrolediones and related compounds," Bioorganic & Medicinal Chemistry, vol. 19, No. 9, May 1, 2011 (May 1, 2011), pp. 2823-2834.

Eisenreichova E et al: "A pyrroline-pyrrolidine alkaloid from lilium candidum bulbs", Phytochemistry, Pergamon Press, GB, vol. 31, No. 3, Mar. 1, 1992 (Mar. 1, 1992), pp. 1084-1085.

K. V. Nikit in et al: "Synthesis of N-Substituted 5-Alkoxy-3-aryl-4-methyl-2,5-dihydro-2-pyrrolones.", Chem Inform, vol. 36, No. 7. Feb. 15, 2005.

Nobuyuki Mase et al: "Regioselective reduction of maleimide and citraconimide derivatives: general preparation of 5-hydroxy-1,5-dihydropyrrol-2-one", Journal of the Chemical Society, Perkin Transactions 1, No. 6, Feb. 12, 2002, pp. 707-709.

Frederic Pin et al: "Intermolecular and Intramolecular [alpha]-Amidoalkylation Reactions Using Bismuth Triflate as the Catalyst", The Journal of Organic Chemistry, vol. 72, No. 4, Feb. 1, 2007, pp. 1181-1191.

Tu Ngoc Duong et al: "Putrescine Bisamides from Aglaia gigantea", Journal of Natural Products, vol. 70. No. 1. Oct. 1, 2007, pp. 1640-1643.

Yakushijin, K. et al.: "Synthesis of (+-)-Jatropham, an Antitumor Alkaloid", Heterocycles, vol. 16, No. 7, Jan. 1, 1981, pp. 1157-1160.

Jan Willem J. F. Thuring et al: "N-Phthaloylglycine-Derived Strigol Analogues. Influence of the D-Ring on Seed Germination Activity of the Parasitic Weeds Striga hermonthica and Orobanche crenata", Journal of Agricultural and Food Chemistry, vol. 45, No. 6, Jun. 1, 1997, pp. 2284-2290.

F.-D. Boyer et al: "Structure-Activity Relationship Studies of Strigolactone-Related Molecules for Branching Inhibition in Garden Pea: Molecule Design for Shoot Branching", Plant Physiology, vol. 159, No. 4, Aug. 1, 2012 pp. 1524-1544.

Search Report for GB1403334.4 mailed Sep. 17, 2014.

PLANT GROWTH REGULATING COMPOUNDS

RELATED APPLICATION INFORMATION

This application is a 371 of International Application No. PCT/EP2015/053826, filed 24 Feb. 2015, which claims priority to EP Patent Application No. 1403334.4, filed 26 Feb. 2014, the contents of which are incorporated by reference herein.

The present invention relates to novel heterocyclic derivatives, to processes and intermediates for preparing them, to plant growth regulating or seed germination promoting compositions comprising them and to methods of using them for controlling the growth of plants and/or promoting the germination of seeds.

Strigolactone derivatives are phytohormones with plant growth regulation and seed germination properties. They have been described, for example, in WO 2009/138655, WO 2010/125065, WO 2005/077177, WO 2006/098626 and *Molecular Plant* (2013), 6, 18-28.

Strigolactone derivatives, like the synthetic analogue GR24, are known to have an effect on the germination of parasitic weeds, such as *Orobanche* species. It is well established in the art that testing for germination of *Orobanche* seeds is a useful test to identify strigolactone analogues (for example, see *Plant and Cell Physiology* (2010), 51(7), 1095 and *Organic & Biomolecular Chemistry* (2009), 7(17), 3413).

Recently, strigolactam derivatives have been reported with similar activity to strigolactones, as described for example in WO 2012/080115 and WO 2013/139949. These derivatives retain similar activity to GR-24 and natural strigolactones in biological assay on plants, controlling plant branching or germination of parasitic weed seeds and mychorrization.

The butenolide ring of strigolactone is considered an important part of the strigolactone compound. Recently, it has also been proposed that an α/β hydrolase (D14 in rice or DAD2 in petunia) acts as the strigolactone receptor and that this protein hydrolyses the butenolide ring of strigolactones (*Current Biology* (2012), 22, 2032-2036 and *Genes to Cell* (2013), 18, 147-160). Even more recently, it has been reported that the hydrolysis of strigolactone by D14 releases the butenolide group that has been proposed to then mediate the interaction with the partner protein SLR1 (*Nature Communication* (2013), 4, 2613).

In the past, it has been reported that the modification of this group has led to a loss of activity on germination (*Journal Agriculture and Food Chemistry* (1997), 2284-2290) or to a loss of control on the plant architecture (*Plant Physiol* (2012), 159, 1524-1544).

The present invention is based on the finding that certain modifications of the butenolide ring surprisingly retain some biological activity exhibited by strigolactone.

According to a first aspect of the present invention, there is provided a compound of Formula (I):

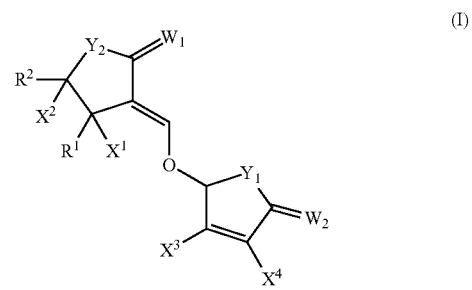

wherein
$W^1$ and $W^2$ are each independently O or S;
$R^1$ and $R^2$ are each independently hydrogen, halogen, nitro, hydroxyl, cyano, substituted or unsubstituted $C_1$-$C_6$alkyl, substituted or unsubstituted $C_1$-$C_6$alkoxy, substituted or unsubstituted aryl, or substituted or unsubstituted heteroaryl; or
$R^1$ and $R^2$ together with the carbon atoms to which they are joined form a saturated or unsaturated, aromatic or non-aromatic, substituted or unsubstituted 3-7-membered carbocycle; or
$R^1$ and $R^2$ together with the carbon atoms to which they are joined form a saturated or unsaturated, aromatic or non-aromatic, substituted or unsubstituted 4-7-membered carbocycle fused to another saturated or unsaturated, aromatic or non-aromatic, substituted or unsubstituted 3-7-membered carbocycle or heterocycle;
$X_1$ and $X_2$ are independently hydrogen, $C_1$-$C_6$ alkyl, $C_1$-$C_6$ haloalkyl, halogen, $C_1$-$C_6$ alkoxy, cyano, nitro, $C_1$-$C_6$alkylsulfinyl, $C_1$-$C_6$alkylsulfonyl or $C_1$-$C_6$alkylthio;
$Y_2$ is oxygen, or $-(CR^4R^7)_p(CR^3R^8)_n-N(R^6)-$, wherein n is 0 or 1, and p is 0 or 1;
$R^3$ and $R^4$ are each independently hydrogen, halogen, nitro, hydroxyl, cyano, substituted or unsubstituted $C_1$-$C_6$alkyl, substituted or unsubstituted $C_1$-$C_6$alkoxy, substituted or unsubstituted aryl, or substituted or unsubstituted heteroaryl; or
$R^3$ and $R^4$ together with the carbon atoms to which they are joined form a saturated or unsaturated, non-aromatic, substituted or unsubstituted 3-7-membered carbocycle; or
$R^3$ and $R^4$ together with the carbon atoms to which they are joined form a saturated or unsaturated, aromatic or non-aromatic, substituted or unsubstituted 4-7-membered carbocycle fused to another saturated or unsaturated, aromatic or non-aromatic, substituted or unsubstituted 3-7-membered carbocycle; or
$R^2$ and $R^3$ together with the carbon atoms to which they are joined form (i) a saturated or unsaturated, non-aromatic, substituted or unsubstituted 3-7-membered carbocycle, or (ii) a saturated or unsaturated, aromatic or non-aromatic, substituted or unsubstituted 4-7-membered carbocycle fused to another saturated or unsaturated aromatic or non-aromatic, substituted or unsubstituted 3-7-membered carbocycle;
$R^7$ and $R^8$ are each independently selected from hydrogen, $C_1$-$C_6$ alkyl, $C_1$-$C_6$ haloalkyl, halogen, $C_1$-$C_6$ alkoxy, aryloxy, $C_1$-$C_6$ alkylsulfinyl, $C_1$-$C_6$ alkylsulfonyl, $C_1$-$C_6$ alkylthio;
$Y_1$ is S or $NR^5$;
$R^5$ and $R^6$ are each independently hydrogen, $C_1$-$C_6$ alkoxy, hydroxyl, amine, N—$C_1$-$C_6$ alkylamine, N,N-di-$C_1$-$C_6$ alkylamine, substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_2$-$C_6$ alkynyl, substituted or unsubstituted $C_1$-$C_8$ alkylcarbonyl, substituted or unsubstituted $C_1$-$C_8$ alkoxycarbonyl, substituted or unsubstituted aryl, substituted or unsubstituted heteroaryl, substituted or unsubstituted heterocyclyl, substituted or unsubstituted benzyl; and $X^3$ and $X^4$ are each independently selected from hydrogen, $C_1$-$C_6$ alkyl, $C_2$-$C_3$ alkynyl, $C_1$-$C_6$ haloalkyl, halogen, hydroxyl, $C_1$-$C_6$ alkoxy, $C_1$-$C_6$ alkylsulfinyl, $C_1$-$C_6$ alkylsulfonyl, $C_1$-$C_6$ alkylthio; or $X^3$ and $X^4$ together with the carbon atoms to which they are attached form a $C_5$- or $C_6$-cycloalkyl;

or an agrochemically acceptable salt or N-oxide thereof.

The compounds of Formula (I) may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of Formula (I).

The term "alkyl" refers to a straight or branched hydrocarbon chain radical consisting solely of carbon and hydrogen atoms, containing no unsaturation, and which is attached to the rest of the molecule by a single bond. Each alkyl moiety either alone or as part of a larger group (such as alkoxy, alkoxycarbonyl, alkylcarbonyl, alkylaminocarbonyl, dialkylaminocarbonyl) can be, for example, methyl, ethyl, n-propyl, n-butyl, n-pentyl, n-hexyl, iso-propyl, n-butyl, sec-butyl, iso-butyl, tert-butyl and neo-pentyl. The alkyl groups may include $C_1$ to $C_6$ alkyl, $C_1$-$C_4$ alkyl and $C_1$-$C_3$ alkyl.

The term "alkenyl" refers to a straight or branched hydrocarbon chain radical consisting solely of carbon and hydrogen atoms, containing at least one double bond that can be of either the (E)- or (Z)-configuration, which is attached to the rest of the molecule by a single bond. Each alkenyl moiety either alone or as part of a larger group (such as alkenoxy, alkenoxycarbonyl, alkenylcarbonyl, alkenylaminocarbonyl, dialkenylaminocarbonyl) can be, for example, vinyl, allyl, prop-1-enyl, but-1-enyl. The alkenyl groups may include $C_2$-$C_6$ alkenyl and $C_2$-$C_4$ alkenyl.

The term "alkynyl" refers to a straight or branched hydrocarbon chain radical consisting solely of carbon and hydrogen atoms, containing at least one triple bond, and which is attached to the rest of the molecule by a single bond. Each alkynyl moiety either alone or as part of a larger group (such as alkynoxy, alkynoxycarbonyl, alkynylcarbonyl, alkynylaminocarbonyl, dialkynylaminocarbonyl) can be, for example, ethynyl, propargyl. The alkynyl groups may include $C_2$-$C_6$ alkynyl and $C_2$-$C_4$ alkynyl.

The term "alkoxy" refers to a radical of the formula —$OR_a$, where $R_a$ is an alkyl radical as generally defined above. Examples of alkoxy include, but are not limited to, methoxy, ethoxy, propoxy, iso-propoxy, butoxy.

The term "alkylthio" refers to a radical of the formula —$SR_a$, where each $R_a$ is an alkyl radical as defined above.

The term "alkylsulfinyl" refers to a radical of the formula —$S(O)R_a$, where each $R_a$ is an alkyl radical as defined above.

The term "alkylsulfonyl" refers to a radical of the formula —$S(O)_2R_a$, where each $R_a$ is an alkyl radical as defined above.

The term "cycloalkyl" refers to a cyclic hydrocarbon radical consisting solely of carbon and hydrogen atoms, containing no unsaturation, and which is attached to the rest of the molecule by a single bond. The cycloalkyl group may be mono-, bi- or tri-cyclic and include $C_3$-$C_6$ cycloalkyl.

Examples of cycloalkyl include, but are not limited to, cyclopropyl, cyclobutyl, cyclopentyl and cyclohexyl.

The term "aryl" refers to an aromatic ring system consisting solely of carbon and hydrogen atoms which may be mono-, bi- or tricyclic. Examples of such ring systems include, but are not limited to, phenyl, naphthalenyl, anthracenyl, indenyl or phenanthrenyl.

The term "aryloxy" refers to a radical of the formula —$OR_a$, where $R_a$ is an aryl radical as generally defined above. Examples of aryloxy include, but are not limited to, phenoxy.

The term "carbocycle" is defined to include ring systems consisting solely of carbon and hydrogen atoms, which may be aromatic or non-aromatic, and include cycloalkyl and aryl.

The term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded to the rest of the molecule via a carbon atom or heteroatom. Examples of heteroaryl include, but are not limited to, furanyl, pyrrolyl, thiophenyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

The term "heterocycle" or "heterocyclyl", as well as referring to heteroaryl, is defined as referring to saturated analogs of heteroaryl, in addition to their unsaturated or partially saturated analogues. In particular, to a cycloalkyl radical, which is a non-aromatic monocyclic or polycyclic ring comprising carbon and hydrogen atoms and at least one heteroatom, for example, 1 to 4 heteroatoms, selected from nitrogen, oxygen, and sulphur. The heterocycle or heterocyclyl radical may be bonded to the rest of the molecule via a carbon atom or a heteroatom. Examples of heterocycle include, but are not limited to, azetidinyl, oxetanyl, pyrrolinyl, pyrrolidyl, tetrahydrofuranyl, tetrahydrothienyl, thietanyl, piperidyl, piperazinyl, tetrahydropyranyl, morpholinyl or perhydroazepinyl. The term "heterocyclyl" also includes 4,5,6,7-tetrahydro-benzothiophenyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl and 4,5-dihydroisoxazolyl groups.

When referred to as, for example, a 3-7-membered carbocycle or heterocycle, this refers to the number of atoms in the cyclic framework, ie, carbon atoms, or carbon atoms and heteroatoms.

The term "halogen" refers to fluorine (F), chlorine (Cl), bromine (Br) or iodine (I).

The term "nitro" refers to a radical of the formula —$NO_2$.

The term "hydroxyl" refers to a radical of the formula —OH.

The term "cyano" refers to a radical of the formula —C≡N.

The term "haloalkyl" (either alone or as part of a larger group, such as haloalkoxy or haloalkylthio) refers to alkyl groups which are substituted with one or more of the same or different halogen atoms and include, but are not limited to, —$CF_3$, —$CF_2Cl$, —$CH_2CF_3$ and —$CH_2CHF_2$.

The term "alkylcarbonyl" refers to a radical of the formula —C(=O)—$R_a$ where $R_a$ is an alkyl radical as defined above. Examples of alkylcarbonyl include, but are not limited to, acetyl.

The term "alkoxycarbonyl" refers to a radical of the formula —C(=O)—O—$R_a$, where $R_a$ is an alkyl radical as defined above. Examples of $C_1$-$C_6$ alkoxycarbonyl include, but are not limited to, methoxycarbonyl, ethoxycarbonyl and iso-propoxycarbonyl.

The term "N-alkylamine" refers to a radical of the formula —NH—$R_a$ where $R_a$ is an alkyl radical as defined above.

The term "N,N-dialkylamino" refers to a radical of the formula —N($R_a$)—$R_a$ where each $R_a$ is an alkyl radical, which may be the same or different, as defined above.

The term "benzyl" refers to a —$CH_2C_6H_5$ radical.

Where a group is stated as being substituted, typically such substituents will be selected from one or more of halogen, amino, cyano, nitro, $C_1$-$C_3$ alkyl, $C_1$-$C_3$ haloalkyl, $C_1$-$C_3$ alkoxy, hydroxyl. In particular, where a carbocyle or heterocycle is substituted, it will comprise 1 to 3 substituents independently selected from halogen, amino, cyano, nitro, $C_1$-$C_3$alkyl, $C_1$-$C_3$haloalkyl, $C_1$-$C_3$alkoxy. Where a carbon chain is substituted, preferred substituents include halogen, amino, cyano and nitro. The skilled man will appreciate that a substituted $C_1$-$C_6$ alkyl group includes inter alia $C_1$-$C_6$haloalkyl, and a substituted $C_1$-$C_6$alkoxy group includes inter alia $C_1$-$C_6$haloalkoxy. In certain embodiments such carbon chains may be substituted by 1 to 5 (more preferably 1 to 3) substituents independently selected from halogen, amino, cyano and nitro.

Preferred values of $W_1$, $W_2$, $Y_1$, $Y_2$, $X_1$, $X_2$, $X_3$, $X_4$, $R^1$, $R^2$, $R^3$, $R^4$, $R^5$, $R^6$, $R^7$ and $R^8$ are, in any combination, as set out below.

Preferably, $W_1$ is oxygen. Preferably, $W_2$ is oxygen. More preferably, $W_1$ and $W_2$ are oxygen.

Preferably, $R^1$, $R^2$ and $R^3$ are each independently hydrogen, substituted or unsubstituted $C_1$-$C_6$ alkyl, substituted or unsubstituted $C_1$-$C_6$ haloalkyl, substituted or unsubstituted aryl, substituted or unsubstituted heteroaryl; or, $R^1$ and $R^2$, or $R^2$ and $R^3$, together with the carbon atoms to which they are joined form a substituted or unsubstituted, saturated or unsaturated, aromatic or non-aromatic 5-6-membered carbocycle; or, $R^1$ and $R^2$, or $R^2$ and $R^3$, together with the carbon atoms to which they are joined form a substituted or unsubstituted, saturated or unsaturated 5-6-membered carbocycle fused to a further saturated or unsaturated, aromatic or non-aromatic, substituted or unsubstituted 5-6-membered carbocycle or heterocycle.

More preferably, $R^1$ and $R^2$, together with the carbon atoms to which they are joined form a substituted or unsubstituted, saturated or unsaturated, 5-6-membered carbocycle; or, $R^1$ and $R^2$, together with the carbon atoms to which they are joined form a substituted or unsubstituted, saturated or unsaturated 5-6-membered carbocycle fused to a further saturated or unsaturated, aromatic or non-aromatic, substituted or unsubstituted 5-6-membered carbocycle or heterocycle.

$R^1$ and $R^2$ together with the carbon atoms to which they are joined may form a substituted or unsubstituted, saturated or unsaturated, 5 membered carbocycle fused to a further substituted or unsubstituted, saturated or unsaturated, aromatic or non-aromatic, 5-6-membered carbocycle or heterocycle. Alternatively, $R^1$ and $R^2$ together with the carbon atoms to which they are joined may form an unsubstituted, saturated or unsaturated non-aromatic 5-membered carbocycle fused to another unsubstituted unsaturated aromatic 6-membered carbocycle. Further, $R^1$ and $R^2$ together with the carbon atoms to which they are joined may form an unsubstituted saturated or unsaturated non-aromatic 5-membered carbocycle fused to another unsubstituted saturated or unsaturated non-aromatic 6-membered carbocycle. Even further, $R^1$ and $R^2$ together with the carbon atoms to which they are joined may form an unsubstituted unsaturated non-aromatic 5-membered carbocycle.

In one set of preferred embodiments $R^1$ and $R^2$ together with the carbon atoms to which they are joined form a substituted or unsubstituted, unsaturated non-aromatic 5-membered carbocycle fused to another substituted or unsubstituted aromatic 6-membered carbocycle, as exemplified in ring system A in Table 1 below.

In a further set of preferred embodiments $R^1$ and $R^2$ together with the carbon atoms to which they are joined form an unsubstituted saturated or unsaturated non-aromatic 5-membered carbocycle fused to another unsubstituted saturated or unsaturated non-aromatic 6-membered carbocycle, as exemplified in ring system B in Table 1 below.

In a further set of preferred embodiments $R^1$ and $R^2$ together with the carbon atoms to which they are joined form an substituted or unsubstituted unsaturated non-aromatic 5-membered carbocycle fused to a substituted unsaturated non-aromatic 6-membered carbocycle, as exemplified in ring system C in Table 1 below.

In a further set of preferred embodiments $R^1$ and $R^2$ together with the carbon atoms to which they are joined form an unsubstituted unsaturated non-aromatic 5-membered carbocycle, as exemplified in ring system D in Table 1 below.

In a further set of preferred embodiments $R^1$ and $R^2$ together with the carbon atoms to which they are joined form an unsubstituted saturated 5-membered carbocycle, as exemplified in ring system E in Table 1 below.

In a further set of preferred embodiments, $R^1$ and $R^2$ together with the carbon atoms to which they are joined do not form a fused cyclic structure, as exemplified in ring system F in Table 1 below.

Preferably, the compound according to Formula (I) is selected from one of Formula (IA), (ID) or (IF) below:

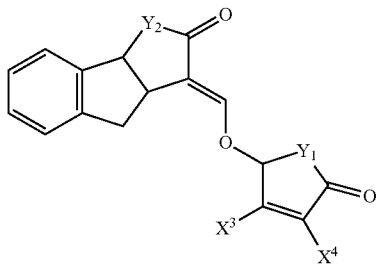

(IA)

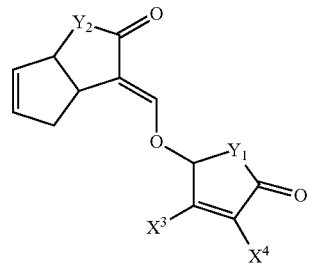

(ID)

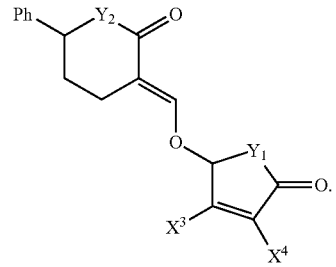

(IF)

Most preferably, the compound according to Formula (I) is the compound of Formula (IA).

As described herein, $Y_2$ is oxygen, or $-(CR^4R^7)_p(CR^3R^8)_nN(R^6)-$. Preferably, $Y_2$ is $-N(R^6)-$.

$R^6$ is preferably hydrogen, substituted or unsubstituted $C_1$-$C_6$ alkyl, $C_1$-$C_8$ alkylcarbonyl, $C_1$-$C_8$ alkoxycarbonyl, substituted or unsubstituted aryl, substituted or unsubstituted heteroaryl. More preferably $R^6$ is hydrogen, $C_1$-$C_3$ alkyl, acetyl, t-butyloxycarbonyl (Boc) or phenyl. Even more preferably, $R^6$ is hydrogen, methyl, ethyl, t-butyloxycarbonyl, phenyl or acetyl. Even further more preferably, $R^6$ is hydrogen or t-butyloxycarbonyl. Most preferably, $R^6$ is hydrogen.

Preferably, $X_3$ and $X_4$ are each independently selected from hydrogen, $C_1$-$C_6$ alkyl, $C_2$-$C_3$ alkynyl, $C_1$-$C_6$ haloalkyl, halogen, and $C_1$-$C_6$ alkoxy. More preferably $X_3$ and $X_4$ are each independently selected from hydrogen, $C_1$-$C_3$alkyl, $C_1$-$C_3$alkoxy and halogen. Even more preferably, $X_3$ and $X_4$ are each independently selected from hydrogen, methyl, methoxy and chloro. Most preferably, $X_3$ is hydrogen or methyl, and $X_4$ is methyl.

Where $R^3$ and $R^4$, or $R^3$ and $R^2$, do not join to form a ring system with the carbon atoms to which they are joined, $R^3$ and $R^4$ are preferably independently selected from hydrogen, halogen, $C_1$-$C_3$ alkyl, $C_1$-$C_3$ haloalkyl, $C_1$-$C_3$ alkoxy, aryl, heteroaryl, more preferably H, Cl, F, methyl, ethyl, propyl, methoxy or $C_1$-$C_3$haloalkyl, phenyl. More preferably still, $R^3$ and $R^4$ are each independently hydrogen, methyl, ethyl, Cl, F, and most preferably $R^3$ and $R^4$ are independently hydrogen.

$R^7$ and $R^8$ are preferably independently selected from hydrogen, halogen, $C_1$-$C_3$alkyl, $C_1$-$C_3$ haloalkyl, $C_1$-$C_3$alkoxy, $C_1$-$C_3$ haloalkoxy, more preferably H, Cl, F, methyl, ethyl, propyl, methoxy or $C_1$-$C_3$haloalkyl. More preferably still, $R^7$ and $R^8$ are each independently hydrogen, methyl, ethyl, Cl, F, and most preferably $R^7$ and $R^8$ are independently hydrogen.

As stated herein, $Y_1$ is S or $NR^5$. Preferably, $Y_1$ is $NR^5$.

$R^5$ is hydrogen, $C_1$-$C_6$ alkoxy, hydroxyl, amine, $N-C_1$-$C_6$alkylamine, N,N-di-$C_1$-$C_6$ alkylamine, substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_2$-$C_6$ alkynyl, substituted or unsubstituted $C_1$-$C_8$ alkylcarbonyl, substituted or unsubstituted $C_1$-$C_8$ alkoxycarbonyl, substituted or unsubstituted aryl, substituted or unsubstituted heteroaryl, substituted or unsubstituted heterocyclyl, or substituted or unsubstituted benzyl.

Preferably $R^5$ is hydrogen, $C_1$-$C_6$ alkoxy, hydroxyl, substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_2$-$C_6$ alkynyl, substituted or unsubstituted $C_1$-$C_8$ alkylcarbonyl, substituted or unsubstituted $C_1$-$C_8$ alkoxycarbonyl, substituted or unsubstituted aryl, substituted or unsubstituted heteroaryl, substituted or unsubstituted heterocyclyl, or substituted or unsubstituted benzyl.

More preferably, $R^5$ is hydrogen, substituted or unsubstituted $C_1$-$C_3$alkyl (including $C_1$-$C_3$ haloalkyl), $C_3$-$C_6$ cycloalkyl, $C_1$-$C_3$ alkoxy, allyl, propargyl, acetyl, substituted or unsubstituted phenyl, pyridyl, thiazoyl, or substituted or unsubstituted benzyl.

Even more preferably, $R^5$ is hydrogen, methyl, methoxy, methoxymethyl, cyclopropyl, allyl, propargyl, acetyl, phenyl, benzyl, pyridyl, thiazolyl, trifluoroethyl, 3-fluorophenyl, 4-fluorophenyl or (3,5-trifluoromethyl)phenyl.

Most preferably, $R^5$ is phenyl, methoxy, 2-trifluoroethyl, cyclopropyl, 3-fluorophenyl, 4-fluorophenyl or 3,5-(trifluoromethyl)phenyl.

Preferably, the compound according to Formula (I) is the compound of Formula (IA); wherein $Y_1$ is $NR^5$;

$R_5$ is $C_1$-$C_3$ alkoxy, substituted or unsubstituted $C_1$-$C_3$alkyl, substituted or unsubstituted $C_3$-$C_6$ cycloalkyl, or substituted or unsubstituted phenyl, $Y_2$ is $-N(R^6)-$;

$R_6$ is hydrogen, methyl or t-butyloxycarbonyl;

$X_3$ is hydrogen or methyl; and $X_4$ is hydrogen or methyl.

More preferably, the compound according to Formula (I) is the compound of Formula (IA); wherein $Y_1$ is $NR^5$;

$R_5$ is $C_1$-$C_3$ alkoxy, $C_1$-$C_3$haloalkyl, $C_3$-$C_6$ cycloalkyl, phenyl or halo-substituted phenyl;

$Y_2$ is $-N(R^6)-$;

$R_6$ is hydrogen or t-butyloxycarbonyl;

$X_3$ is hydrogen or methyl; and $X_4$ is hydrogen or methyl.

Even more preferably, the compound according to Formula (I) is the compound of Formula (IA); wherein $Y_1$ is $NR^5$;

$R_5$ is $C_1$-$C_3$ alkoxy, $C_1$-$C_3$fluoroalkyl, $C_3$-$C_6$ cycloalkyl, phenyl or fluoro-substituted phenyl;

$Y_2$ is $-N(R^6)-$;

$R_6$ is hydrogen;

$X_3$ is hydrogen or methyl; and $X_4$ is methyl.

Still more preferably, the compound according to Formula (I) is the compound of Formula (IA); wherein $Y_1$ is $NR^5$;

$R_5$ is $C_1$-$C_3$ alkoxy, $C_1$-$C_3$fluoroalkyl, $C_3$-$C_6$ cycloalkyl, phenyl or fluoro-substituted phenyl;

$Y_2$ is $-N(R^6)-$;

$R_6$ is hydrogen;

$X_3$ is hydrogen or methyl; and $X_4$ is methyl.

Most preferably, the compound according to Formula (I) is the compound of Formula (IA); wherein $Y_1$ is $NR^5$;

$R_5$ is phenyl, methoxy, 2-trifluoroethyl, cyclopropyl, 3-fluorophenyl, 4-fluorophenyl or (3,5-trifluoromethyl)phenyl;

$Y_2$ is $-N(R^6)-$;

$R_6$ is hydrogen;

$X_3$ is hydrogen or methyl; and $X_4$ is methyl.

TABLE 1

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

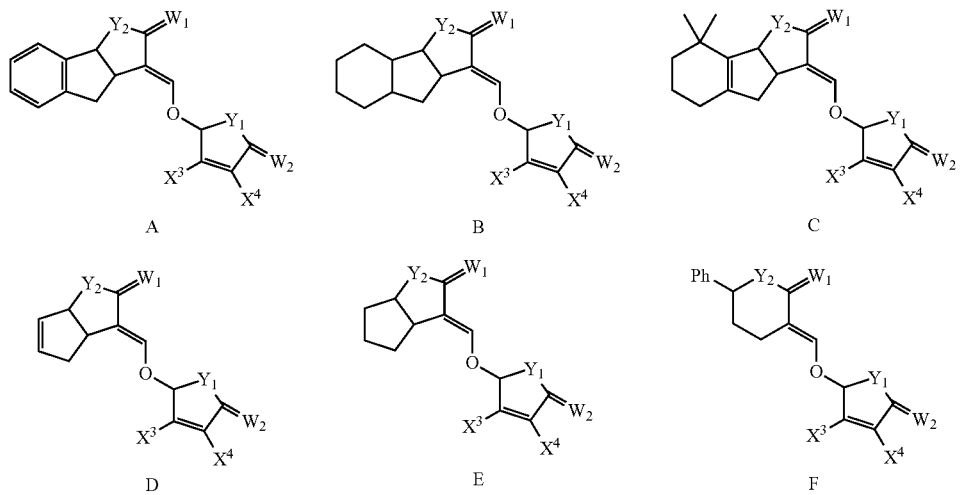

A    B    C

D    E    F

| Compound No. | Ring system | $R^5$ | $Y_2$ | $X^3$ | $X^4$ |
|---|---|---|---|---|---|
| 1.00 | A | —Me | O | H | Me |
| 1.01 | A | —OMe | O | H | Me |
| 1.02 | A | —CH$_2$OMe | O | H | Me |
| 1.03 | A | —CH$_2$CCH | O | H | Me |
| 1.04 | A | —Ph | O | H | Me |
| 1.05 | A | —2-Py | O | H | Me |
| 1.06 | A | —CH$_2$CF$_3$ | O | H | Me |
| 1.07 | A | —cyclopropyl | O | H | Me |
| 1.08 | A | —Ac | O | H | Me |
| 1.09 | A | —(2-thiazoyl) | O | H | Me |
| 1.10 | A | —(3-thienyl) | O | H | Me |
| 1.11 | A | —(4-F)Ph | O | H | Me |
| 1.12 | A | —(3-F)Ph | O | H | Me |
| 1.13 | A | —(2-F)Ph | O | H | Me |
| 1.14 | A | —(3,5-F)Ph | O | H | Me |
| 1.15 | A | —(2,6-F)Ph | O | H | Me |
| 1.16 | A | —(3,5-CF3)Ph | O | H | Me |
| 1.17 | A | —Me | NH | H | Me |
| 1.18 | A | —OMe | NH | H | Me |
| 1.19 | A | —CH$_2$OMe | NH | H | Me |
| 1.20 | A | —CH$_2$CCH | NH | H | Me |
| 1.21 | A | —Ph | NH | H | Me |
| 1.22 | A | —2-Py | NH | H | Me |
| 1.23 | A | —CH$_2$CF$_3$ | NH | H | Me |
| 1.24 | A | —cyclopropyl | NH | H | Me |
| 1.25 | A | —Ac | NH | H | Me |
| 1.26 | A | —(2-thiazoyl) | NH | H | Me |
| 1.27 | A | —(3-thienyl) | NH | H | Me |
| 1.28 | A | —(4-F)Ph | NH | H | Me |
| 1.29 | A | —(3-F)Ph | NH | H | Me |
| 1.30 | A | —(2-F)Ph | NH | H | Me |
| 1.31 | A | —(3,5-F)Ph | NH | H | Me |
| 1.32 | A | —(2,6-F)Ph | NH | H | Me |
| 1.33 | A | —(3,5-CF3)Ph | NH | H | Me |
| 1.34 | A | —Me | NMe | H | Me |
| 1.35 | A | —OMe | NMe | H | Me |
| 1.36 | A | —CH$_2$OMe | NMe | H | Me |
| 1.37 | A | —CH$_2$CCH | NMe | H | Me |
| 1.38 | A | —Ph | NMe | H | Me |
| 1.39 | A | —2-Py | NMe | H | Me |
| 1.40 | A | —CH$_2$CF$_3$ | NMe | H | Me |
| 1.41 | A | —cyclopropyl | NMe | H | Me |
| 1.42 | A | —Ac | NMe | H | Me |
| 1.43 | A | —(2-thiazoyl) | NMe | H | Me |
| 1.44 | A | —(3-thienyl) | NMe | H | Me |
| 1.45 | A | —(4-F)Ph | NMe | H | Me |
| 1.46 | A | —(3-F)Ph | NMe | H | Me |
| 1.47 | A | —(2-F)Ph | NMe | H | Me |
| 1.48 | A | —(3,5-F)Ph | NMe | H | Me |
| 1.49 | A | —(2,6-F)Ph | NMe | H | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

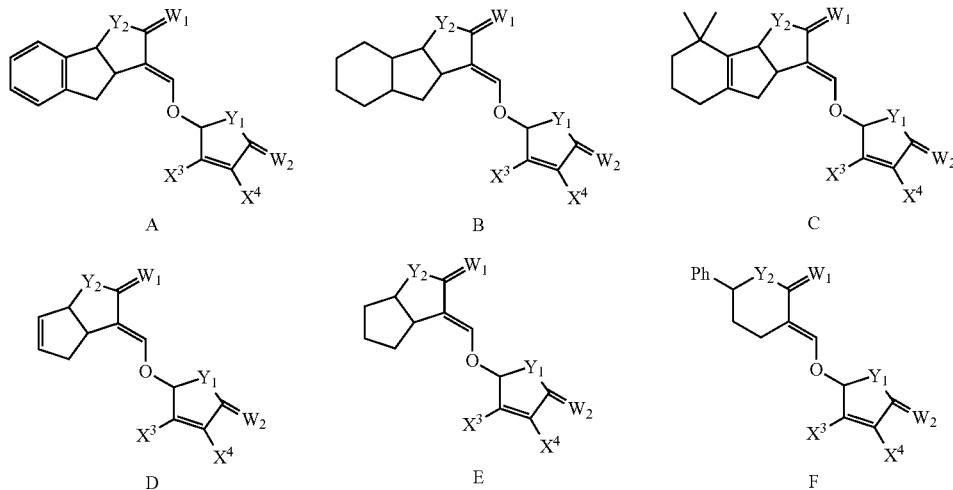

A  B  C  D  E  F

| Compound No. | Ring system | $R^5$ | $Y_2$ | $X^3$ | $X^4$ |
|---|---|---|---|---|---|
| 1.50 | A | —(3,5-CF3)Ph | NMe | H | Me |
| 1.51 | D | —Me | O | H | Me |
| 1.52 | D | —OMe | O | H | Me |
| 1.53 | D | —CH$_2$OMe | O | H | Me |
| 1.54 | D | —CH$_2$CCH | O | H | Me |
| 1.55 | D | —Ph | O | H | Me |
| 1.56 | D | —2-Py | O | H | Me |
| 1.57 | D | —CH$_2$CF$_3$ | O | H | Me |
| 1.58 | D | —cyclopropyl | O | H | Me |
| 1.59 | D | —Ac | O | H | Me |
| 1.60 | D | —(2-thiazoyl) | O | H | Me |
| 1.61 | D | —iPr | O | H | Me |
| 1.62 | D | —(3-thienyl) | O | H | Me |
| 1.63 | D | —(4-F)Ph | O | H | Me |
| 1.64 | D | —(3-F)Ph | O | H | Me |
| 1.65 | D | —(2-F)Ph | O | H | Me |
| 1.66 | D | —(3,5-F)Ph | O | H | Me |
| 1.67 | D | —(2,6-F)Ph | O | H | Me |
| 1.68 | D | —(3,5-CF3)Ph | O | H | Me |
| 1.69 | D | —Me | NH | H | Me |
| 1.70 | D | —OMe | NH | H | Me |
| 1.71 | D | —CH$_2$OMe | NH | H | Me |
| 1.72 | D | —CH$_2$CCH | NH | H | Me |
| 1.73 | D | —Ph | NH | H | Me |
| 1.74 | D | —2-Py | NH | H | Me |
| 1.75 | D | —CH$_2$CF$_3$ | NH | H | Me |
| 1.76 | D | —cyclopropyl | NH | H | Me |
| 1.77 | D | —Ac | NH | H | Me |
| 1.78 | D | —(2-thiazoyl) | NH | H | Me |
| 1.79 | D | —(3-thienyl) | NH | H | Me |
| 1.80 | D | —(4-F)Ph | NH | H | Me |
| 1.81 | D | —(3-F)Ph | NH | H | Me |
| 1.82 | D | —(2-F)Ph | NH | H | Me |
| 1.83 | D | —(3,5-F)Ph | NH | H | Me |
| 1.84 | D | —(2,6-F)Ph | NH | H | Me |
| 1.85 | D | —(3,5-CF3)Ph | NH | H | Me |
| 1.86 | D | —Me | NMe | H | Me |
| 1.87 | D | —OMe | NMe | H | Me |
| 1.88 | D | —CH$_2$OMe | NMe | H | Me |
| 1.89 | D | —CH$_2$CCH | NMe | H | Me |
| 1.90 | D | —Ph | NMe | H | Me |
| 1.91 | D | —2-Py | NMe | H | Me |
| 1.92 | D | —CH$_2$CF$_3$ | NMe | H | Me |
| 1.93 | D | —cyclopropyl | NMe | H | Me |
| 1.94 | D | —Ac | NMe | H | Me |
| 1.95 | D | —(2-thiazoyl) | NMe | H | Me |
| 1.96 | D | —(3-thienyl) | NMe | H | Me |
| 1.97 | D | —(4-F)Ph | NMe | H | Me |
| 1.98 | D | —(3-F)Ph | NMe | H | Me |
| 1.99 | D | —(2-F)Ph | NMe | H | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.
Ring system:

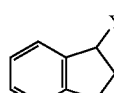

A

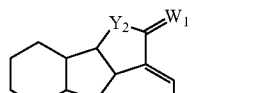

B

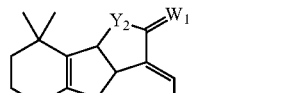

C

D

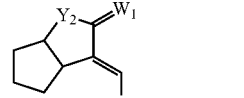

E

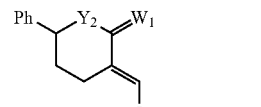

F

| Compound No. | Ring system | $R^5$ | $Y_2$ | $X^3$ | $X^4$ |
| --- | --- | --- | --- | --- | --- |
| 2.00 | D | —(3,5-F)Ph | NMe | H | Me |
| 2.01 | D | —(2,6-F)Ph | NMe | H | Me |
| 2.02 | D | —(3,5-CF3)Ph | NMe | H | Me |
| 2.03 | E | —Me | O | H | Me |
| 2.04 | E | —OMe | O | H | Me |
| 2.05 | E | —CH$_2$OMe | O | H | Me |
| 2.06 | E | —CH$_2$CCH | O | H | Me |
| 2.07 | E | —Ph | O | H | Me |
| 2.08 | E | —2-Py | O | H | Me |
| 2.09 | E | —CH$_2$CF$_3$ | O | H | Me |
| 2.10 | E | —cyclopropyl | O | H | Me |
| 2.11 | E | —Ac | O | H | Me |
| 2.12 | E | —(2-thiazoyl) | O | H | Me |
| 2.13 | E | —iPr | O | H | Me |
| 2.14 | E | —(3-thienyl) | O | H | Me |
| 2.15 | E | —(4-F)Ph | O | H | Me |
| 2.16 | E | —(3-F)Ph | O | H | Me |
| 2.17 | E | —(2-F)Ph | O | H | Me |
| 2.18 | E | —(3,5-F)Ph | O | H | Me |
| 2.19 | E | —(2,6-F)Ph | O | H | Me |
| 2.20 | E | —(3,5-CF3)Ph | O | H | Me |
| 2.21 | E | —Me | NH | H | Me |
| 2.22 | E | —OMe | NH | H | Me |
| 2.23 | E | —CH$_2$OMe | NH | H | Me |
| 2.24 | E | —CH$_2$CCH | NH | H | Me |
| 2.25 | E | —Ph | NH | H | Me |
| 2.26 | E | —2-Py | NH | H | Me |
| 2.27 | E | —CH$_2$CF$_3$ | NH | H | Me |
| 2.28 | E | —cyclopropyl | NH | H | Me |
| 2.29 | E | —Ac | NH | H | Me |
| 2.30 | E | —(2-thiazoyl) | NH | H | Me |
| 2.31 | E | —(3-thienyl) | NH | H | Me |
| 2.32 | E | —(4-F)Ph | NH | H | Me |
| 2.33 | E | —(3-F)Ph | NH | H | Me |
| 2.34 | E | —(2-F)Ph | NH | H | Me |
| 2.35 | E | —(3,5-F)Ph | NH | H | Me |
| 2.36 | E | —(2,6-F)Ph | NH | H | Me |
| 2.37 | E | —(3,5-CF3)Ph | NH | H | Me |
| 2.38 | E | —Me | NMe | H | Me |
| 2.39 | E | —OMe | NMe | H | Me |
| 2.40 | E | —CH$_2$OMe | NMe | H | Me |
| 2.41 | E | —CH$_2$CCH | NMe | H | Me |
| 2.42 | E | —Ph | NMe | H | Me |
| 2.43 | E | 2-Py | NMe | H | Me |
| 2.44 | E | —CH$_2$CF$_3$ | NMe | H | Me |
| 2.45 | E | —cyclopropyl | NMe | H | Me |
| 2.46 | E | —Ac | NMe | H | Me |
| 2.47 | E | —(2-thiazoyl) | NMe | H | Me |
| 2.48 | E | —(3-thienyl) | NMe | H | Me |
| 2.49 | E | —(4-F)Ph | NMe | H | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

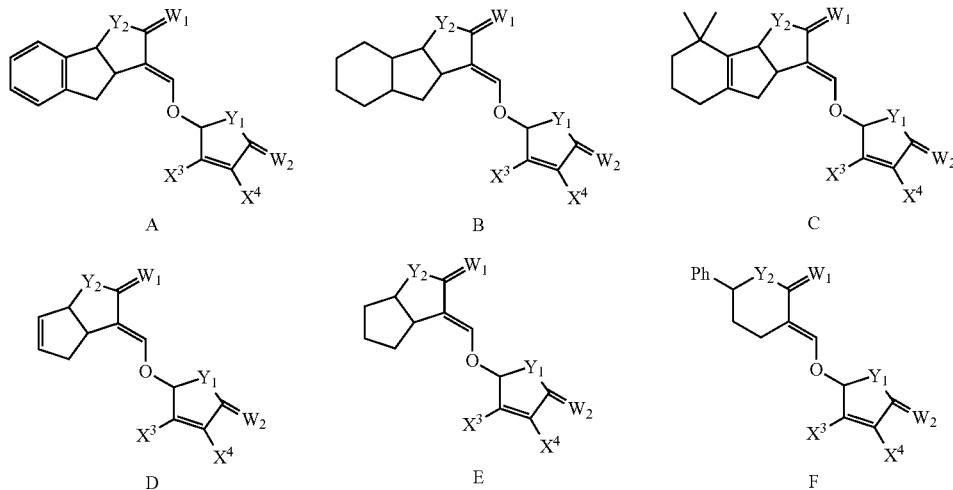

| Compound No. | Ring system | $R^5$ | $Y_2$ | $X^3$ | $X^4$ |
|---|---|---|---|---|---|
| 2.50 | E | —(3-F)Ph | NMe | H | Me |
| 2.51 | E | —(2-F)Ph | NMe | H | Me |
| 2.52 | E | —(3,5-F)Ph | NMe | H | Me |
| 2.53 | E | —(2,6-F)Ph | NMe | H | Me |
| 2.54 | E | —(3,5-CF3)Ph | NMe | H | Me |
| 2.55 | B | —Me | O | H | Me |
| 2.56 | B | —OMe | O | H | Me |
| 2.57 | B | —CH$_2$OMe | O | H | Me |
| 2.58 | B | —CH$_2$CCH | O | H | Me |
| 2.59 | B | —Ph | O | H | Me |
| 2.60 | B | —2-Py | O | H | Me |
| 2.61 | B | —CH$_2$CF$_3$ | O | H | Me |
| 2.62 | B | —cyclopropyl | O | H | Me |
| 2.63 | B | —Ac | O | H | Me |
| 2.64 | B | —(2-thiazoyl) | O | H | Me |
| 2.65 | B | —iPr | O | H | Me |
| 2.66 | B | —(3-thienyl) | O | H | Me |
| 2.67 | B | —(4-F)Ph | O | H | Me |
| 2.68 | B | —(3-F)Ph | O | H | Me |
| 2.69 | B | —(2-F)Ph | O | H | Me |
| 2.70 | B | —(3,5-F)Ph | O | H | Me |
| 2.71 | B | —(2,6-F)Ph | O | H | Me |
| 2.72 | B | —(3,5-CF3)Ph | O | H | Me |
| 2.73 | B | —Me | NH | H | Me |
| 2.74 | B | —OMe | NH | H | Me |
| 2.75 | B | —CH$_2$OMe | NH | H | Me |
| 2.76 | B | —CH$_2$CCH | NH | H | Me |
| 2.77 | B | —Ph | NH | H | Me |
| 2.78 | B | —2-Py | NH | H | Me |
| 2.79 | B | —CH$_2$CF$_3$ | NH | H | Me |
| 2.80 | B | —cyclopropyl | NH | H | Me |
| 2.81 | B | —Ac | NH | H | Me |
| 2.82 | B | —(2-thiazoyl) | NH | H | Me |
| 2.83 | B | —(3-thienyl) | NH | H | Me |
| 2.84 | B | —(4-F)Ph | NH | H | Me |
| 2.85 | B | —(3-F)Ph | NH | H | Me |
| 2.86 | B | —(2-F)Ph | NH | H | Me |
| 2.87 | B | —(3,5-F)Ph | NH | H | Me |
| 2.88 | B | —(2,6-F)Ph | NH | H | Me |
| 2.89 | B | —(3,5-CF3)Ph | NH | H | Me |
| 2.90 | B | —Me | NMe | H | Me |
| 2.91 | B | —OMe | NMe | H | Me |
| 2.92 | B | —CH$_2$OMe | NMe | H | Me |
| 2.93 | B | —CH$_2$CCH | NMe | H | Me |
| 2.94 | B | —Ph | NMe | H | Me |
| 2.95 | B | —2-Py | NMe | H | Me |
| 2.96 | B | —CH$_2$CF$_3$ | NMe | H | Me |
| 2.97 | B | —cyclopropyl | NMe | H | Me |
| 2.98 | B | —Ac | NMe | H | Me |
| 2.99 | B | —(2-thiazoyl) | NMe | H | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

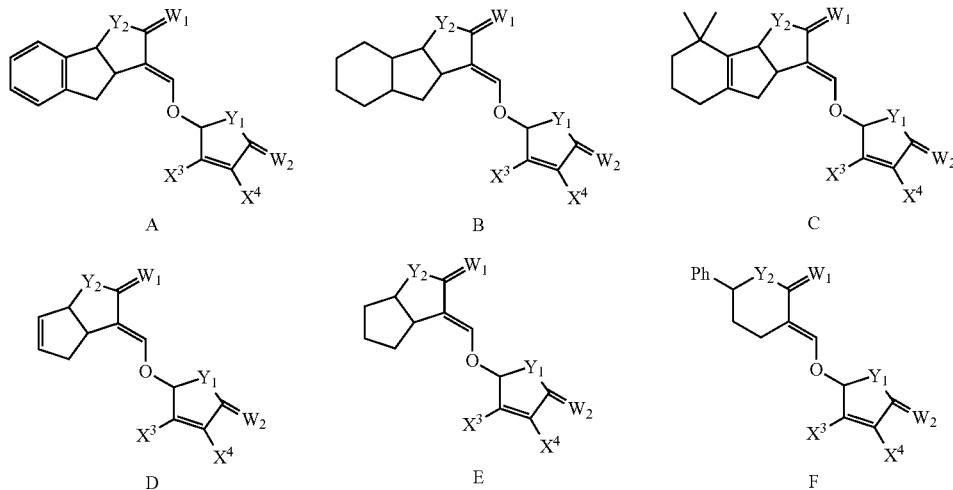

| Compound No. | Ring system | $R^5$ | $Y_2$ | $X^3$ | $X^4$ |
|---|---|---|---|---|---|
| 3.00 | B | —(3-thienyl) | NMe | H | Me |
| 3.01 | B | —(4-F)Ph | NMe | H | Me |
| 3.02 | B | —(3-F)Ph | NMe | H | Me |
| 3.03 | B | —(2-F)Ph | NMe | H | Me |
| 3.04 | B | —(3,5-F)Ph | NMe | H | Me |
| 3.05 | B | —(2,6-F)Ph | NMe | H | Me |
| 3.06 | B | —(3,5-CF3)Ph | NMe | H | Me |
| 3.07 | C | —Me | O | H | Me |
| 3.08 | C | —OMe | O | H | Me |
| 3.09 | C | —CH$_2$OMe | O | H | Me |
| 3.10 | C | —CH$_2$CCH | O | H | Me |
| 3.11 | C | —Ph | O | H | Me |
| 3.12 | C | —2-Py | O | H | Me |
| 3.13 | C | —CH$_2$CF$_3$ | O | H | Me |
| 3.14 | C | —cyclopropyl | O | H | Me |
| 3.15 | C | —Ac | O | H | Me |
| 3.16 | C | —(2-thiazoyl) | O | H | Me |
| 3.17 | C | —iPr | O | H | Me |
| 3.18 | C | —(3-thienyl) | O | H | Me |
| 3.19 | C | —(4-F)Ph | O | H | Me |
| 3.20 | C | —(3-F)Ph | O | H | Me |
| 3.21 | C | —(2-F)Ph | O | H | Me |
| 3.22 | C | —(3,5-F)Ph | O | H | Me |
| 3.23 | C | —(2,6-F)Ph | O | H | Me |
| 3.24 | C | —(3,5-CF3)Ph | O | H | Me |
| 3.25 | C | —Me | NH | H | Me |
| 3.26 | C | —OMe | NH | H | Me |
| 3.27 | C | —CH$_2$OMe | NH | H | Me |
| 3.28 | C | —CH$_2$CCH | NH | H | Me |
| 3.29 | C | —Ph | NH | H | Me |
| 3.30 | C | —2-Py | NH | H | Me |
| 3.31 | C | —CH$_2$CF$_3$ | NH | H | Me |
| 3.32 | C | —cyclopropyl | NH | H | Me |
| 3.33 | C | —Ac | NH | H | Me |
| 3.34 | C | —(2-thiazoyl) | NH | H | Me |
| 3.35 | C | —(3-thienyl) | NH | H | Me |
| 3.36 | C | —(4-F)Ph | NH | H | Me |
| 3.37 | C | —(3-F)Ph | NH | H | Me |
| 3.38 | C | —(2-F)Ph | NH | H | Me |
| 3.39 | C | —(3,5-F)Ph | NH | H | Me |
| 3.40 | C | —(2,6-F)Ph | NH | H | Me |
| 3.41 | C | —(3,5-CF3)Ph | NH | H | Me |
| 3.42 | C | —Me | NMe | H | Me |
| 3.43 | C | —OMe | NMe | H | Me |
| 3.44 | C | —CH$_2$OMe | NMe | H | Me |
| 3.45 | C | —CH$_2$CCH | NMe | H | Me |
| 3.46 | C | —Ph | NMe | H | Me |
| 3.47 | C | —2-Py | NMe | H | Me |
| 3.48 | C | —CH$_2$CF$_3$ | NMe | H | Me |
| 3.49 | C | —cyclopropyl | NMe | H | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.
Ring system:

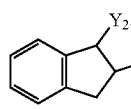

A

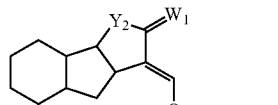

B

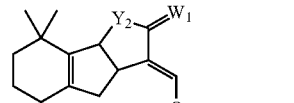

C

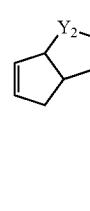

D

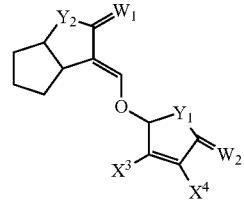

E

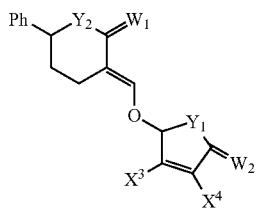

F

| Compound No. | Ring system | $R^5$ | $Y_2$ | $X^3$ | $X^4$ |
|---|---|---|---|---|---|
| 3.50 | C | —Ac | NMe | H | Me |
| 3.51 | C | —(2-thiazoyl) | NMe | H | Me |
| 3.52 | C | —(3-thienyl) | NMe | H | Me |
| 3.53 | C | —(4-F)Ph | NMe | H | Me |
| 3.54 | C | —(3-F)Ph | NMe | H | Me |
| 3.55 | C | —(2-F)Ph | NMe | H | Me |
| 3.56 | C | —(3,5-F)Ph | NMe | H | Me |
| 3.57 | C | —(2,6-F)Ph | NMe | H | Me |
| 3.58 | C | —(3,5-CF3)Ph | NMe | H | Me |
| 3.59 | A | —Me | O | Me | H |
| 3.60 | A | —OMe | O | Me | H |
| 3.61 | A | —CH$_2$OMe | O | Me | H |
| 3.62 | A | —CH$_2$CCH | O | Me | H |
| 3.63 | A | —Ph | O | Me | H |
| 3.64 | A | —2-Py | O | Me | H |
| 3.65 | A | —CH$_2$CF$_3$ | O | Me | H |
| 3.66 | A | —cyclopropyl | O | Me | H |
| 3.67 | A | —Ac | O | Me | H |
| 3.68 | A | —(2-thiazoyl) | O | Me | H |
| 3.69 | A | —iPr | O | Me | H |
| 3.70 | A | —(3-thienyl) | O | Me | H |
| 3.71 | A | —(4-F)Ph | O | Me | H |
| 3.72 | A | —(3-F)Ph | O | Me | H |
| 3.73 | A | —(2-F)Ph | O | Me | H |
| 3.74 | A | —(3,5-F)Ph | O | Me | H |
| 3.75 | A | —(2,6-F)Ph | O | Me | H |
| 3.76 | A | —(3,5-CF3)Ph | O | Me | H |
| 3.77 | A | —Me | NH | Me | H |
| 3.78 | A | —OMe | NH | Me | H |
| 3.79 | A | —CH$_2$OMe | NH | Me | H |
| 3.80 | A | —CH$_2$CCH | NH | Me | H |
| 3.81 | A | —Ph | NH | Me | H |
| 3.82 | A | —2-Py | NH | Me | H |
| 3.83 | A | —CH$_2$CF$_3$ | NH | Me | H |
| 3.84 | A | —cyclopropyl | NH | Me | H |
| 3.85 | A | —Ac | NH | Me | H |
| 3.86 | A | —(2-thiazoyl) | NH | Me | H |
| 3.87 | A | —(3-thienyl) | NH | Me | H |
| 3.88 | A | —(4-F)Ph | NH | Me | H |
| 3.89 | A | —(3-F)Ph | NH | Me | H |
| 3.90 | A | —(2-F)Ph | NH | Me | H |
| 3.91 | A | —(3,5-F)Ph | NH | Me | H |
| 3.92 | A | —(2,6-F)Ph | NH | Me | H |
| 3.93 | A | —(3,5-CF3)Ph | NH | Me | H |
| 3.94 | A | —Me | NMe | Me | H |
| 3.95 | A | —OMe | NMe | Me | H |
| 3.96 | A | —CH$_2$OMe | NMe | Me | H |
| 3.97 | A | —CH$_2$CCH | NMe | Me | H |
| 3.98 | A | —Ph | NMe | Me | H |
| 3.99 | A | —2-Py | NMe | Me | H |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

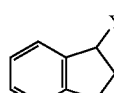
A

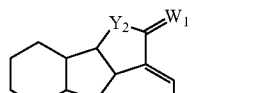
B

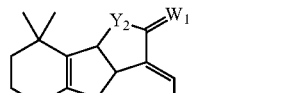
C

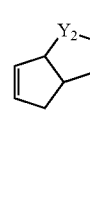
D

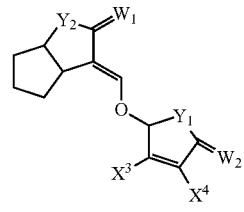
E

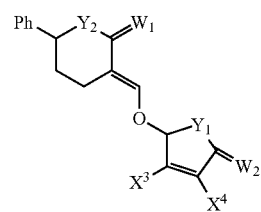
F

| Compound No. | Ring system | $R^5$ | $Y_2$ | $X^3$ | $X^4$ |
|---|---|---|---|---|---|
| 4.00 | A | —CH$_2$CF$_3$ | NMe | Me | H |
| 4.01 | A | —cyclopropyl | NMe | Me | H |
| 4.02 | A | —Ac | NMe | Me | H |
| 4.03 | A | —(2-thiazoyl) | NMe | Me | H |
| 4.04 | A | —(3-thienyl) | NMe | Me | H |
| 4.05 | A | —(4-F)Ph | NMe | Me | H |
| 4.06 | A | —(3-F)Ph | NMe | Me | H |
| 4.07 | A | —(2-F)Ph | NMe | Me | H |
| 4.08 | A | —(3,5-F)Ph | NMe | Me | H |
| 4.09 | A | —(2,6-F)Ph | NMe | Me | H |
| 4.10 | A | —(3,5-CF3)Ph | NMe | Me | H |
| 4.11 | D | —Me | O | Me | H |
| 4.12 | D | —OMe | O | Me | H |
| 4.13 | D | —CH$_2$OMe | O | Me | H |
| 4.14 | D | —CH$_2$CCH | O | Me | H |
| 4.15 | D | —Ph | O | Me | H |
| 4.16 | D | —2-Py | O | Me | H |
| 4.17 | D | —CH$_2$CF$_3$ | O | Me | H |
| 4.18 | D | —cyclopropyl | O | Me | H |
| 4.19 | D | —Ac | O | Me | H |
| 4.20 | D | —(2-thiazoyl) | O | Me | H |
| 4.21 | D | —iPr | O | Me | H |
| 4.22 | D | —(3-thienyl) | O | Me | H |
| 4.23 | D | —(4-F)Ph | O | Me | H |
| 4.24 | D | —(3-F)Ph | O | Me | H |
| 4.25 | D | —(2-F)Ph | O | Me | H |
| 4.26 | D | —(3,5-F)Ph | O | Me | H |
| 4.27 | D | —(2,6-F)Ph | O | Me | H |
| 4.28 | D | —(3,5-CF3)Ph | O | Me | H |
| 4.29 | D | —Me | NH | Me | H |
| 4.30 | D | —OMe | NH | Me | H |
| 4.31 | D | —CH$_2$OMe | NH | Me | H |
| 4.32 | D | —CH$_2$CCH | NH | Me | H |
| 4.33 | D | —Ph | NH | Me | H |
| 4.34 | D | —2-Py | NH | Me | H |
| 4.35 | D | —CH$_2$CF$_3$ | NH | Me | H |
| 4.36 | D | —cyclopropyl | NH | Me | H |
| 4.37 | D | —Ac | NH | Me | H |
| 4.38 | D | —(2-thiazoyl) | NH | Me | H |
| 4.39 | D | —(3-thienyl) | NH | Me | H |
| 4.40 | D | —(4-F)Ph | NH | Me | H |
| 4.41 | D | —(3-F)Ph | NH | Me | H |
| 4.42 | D | —(2-F)Ph | NH | Me | H |
| 4.43 | D | —(3,5-F)Ph | NH | Me | H |
| 4.44 | D | —(2,6-F)Ph | NH | Me | H |
| 4.45 | D | —(3,5-CF3)Ph | NH | Me | H |
| 4.46 | D | —Me | NMe | Me | H |
| 4.47 | D | —OMe | NMe | Me | H |
| 4.48 | D | —NCH$_2$OMe | NMe | Me | H |
| 4.49 | D | —CH$_2$CCH | NMe | Me | H |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

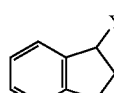
A

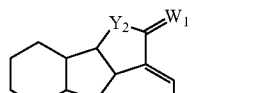
B

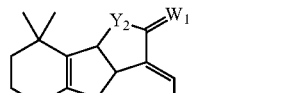
C

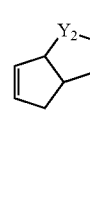
D

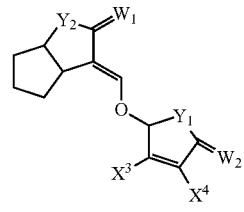
E

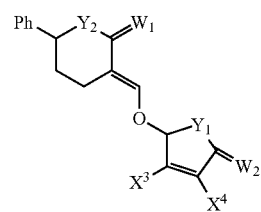
F

| Compound No. | Ring system | $R^5$ | $Y_2$ | $X^3$ | $X^4$ |
| --- | --- | --- | --- | --- | --- |
| 4.50 | D | —Ph | NMe | Me | H |
| 4.51 | D | —2-Py | NMe | Me | H |
| 4.52 | D | —CH$_2$CF$_3$ | NMe | Me | H |
| 4.53 | D | —cyclopropyl | NMe | Me | H |
| 4.54 | D | —Ac | NMe | Me | H |
| 4.55 | D | —(2-thiazoyl) | NMe | Me | H |
| 4.56 | D | —(3-thienyl) | NMe | Me | H |
| 4.57 | D | —(4-F)Ph | NMe | Me | H |
| 4.58 | D | —(3-F)Ph | NMe | Me | H |
| 4.59 | D | —(2-F)Ph | NMe | Me | H |
| 4.60 | D | —(3,5-F)Ph | NMe | Me | H |
| 4.61 | D | —(2,6-F)Ph | NMe | Me | H |
| 4.62 | D | —(3,5-CF3)Ph | NMe | Me | H |
| 4.63 | E | —Me | O | Me | H |
| 4.64 | E | —OMe | O | Me | H |
| 4.65 | E | —CH$_2$OMe | O | Me | H |
| 4.66 | E | —CH$_2$CCH | O | Me | H |
| 4.67 | E | —Ph | O | Me | H |
| 4.68 | E | —2-Py | O | Me | H |
| 4.69 | E | —CH$_2$CF$_3$ | O | Me | H |
| 4.70 | E | —cyclopropyl | O | Me | H |
| 4.71 | E | —Ac | O | Me | H |
| 4.72 | E | —(2-thiazoyl) | O | Me | H |
| 4.73 | E | —iPr | O | Me | H |
| 4.74 | E | —(3-thienyl) | O | Me | H |
| 4.75 | E | —(4-F)Ph | O | Me | H |
| 4.76 | E | —(3-F)Ph | O | Me | H |
| 4.77 | E | —(2-F)Ph | O | Me | H |
| 4.78 | E | —(3,5-F)Ph | O | Me | H |
| 4.79 | E | —(2,6-F)Ph | O | Me | H |
| 4.80 | E | —(3,5-CF3)Ph | O | Me | H |
| 4.81 | E | —Me | NH | Me | H |
| 4.82 | E | —OMe | NH | Me | H |
| 4.83 | E | —CH$_2$OMe | NH | Me | H |
| 4.84 | E | —CH$_2$CCH | NH | Me | H |
| 4.85 | E | —Ph | NH | Me | H |
| 4.86 | E | —2-Py | NH | Me | H |
| 4.87 | E | —CH$_2$CF$_3$ | NH | Me | H |
| 4.88 | E | —cyclopropyl | NH | Me | H |
| 4.89 | E | —Ac | NH | Me | H |
| 4.90 | E | —(2-thiazoyl) | NH | Me | H |
| 4.91 | E | —(3-thienyl) | NH | Me | H |
| 4.92 | E | —(4-F)Ph | NH | Me | H |
| 4.93 | E | —(3-F)Ph | NH | Me | H |
| 4.94 | E | —(2-F)Ph | NH | Me | H |
| 4.95 | E | —(3,5-F)Ph | NH | Me | H |
| 4.96 | E | —(2,6-F)Ph | NH | Me | H |
| 4.97 | E | —(3,5-CF3)Ph | NH | Me | H |
| 4.98 | E | —Me | NMe | Me | H |
| 4.99 | E | —OMe | NMe | Me | H |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.
Ring system:

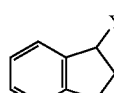
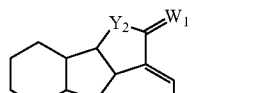
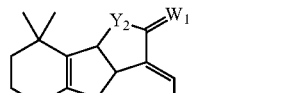

A        B        C

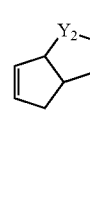
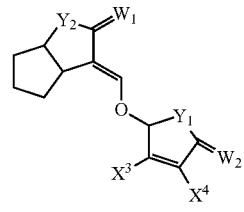
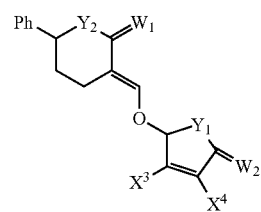

D        E        F

| Compound No. | Ring system | $R^5$ | $Y_2$ | $X^3$ | $X^4$ |
|---|---|---|---|---|---|
| 5.00 | E | —CH$_2$OMe | NMe | Me | H |
| 5.01 | E | —CH$_2$CCH | NMe | Me | H |
| 5.02 | E | —Ph | NMe | Me | H |
| 5.03 | E | —2-Py | NMe | Me | H |
| 5.04 | E | —CH$_2$CF$_3$ | NMe | Me | H |
| 5.05 | E | —CH(CH$_2$-CH$_2$) | NMe | Me | H |
| 5.06 | E | —Ac | NMe | Me | H |
| 5.07 | E | —(2-thiazoyl) | NMe | Me | H |
| 5.08 | E | —(3-thienyl) | NMe | Me | H |
| 5.09 | E | —(4-F)Ph | NMe | Me | H |
| 5.10 | E | —(3-F)Ph | NMe | Me | H |
| 5.11 | E | —(2-F)Ph | NMe | Me | H |
| 5.12 | E | —(3,5-F)Ph | NMe | Me | H |
| 5.13 | E | —(2,6-F)Ph | NMe | Me | H |
| 5.14 | E | —(3,5-CF3)Ph | NMe | Me | H |
| 5.15 | F | —Me | O | Me | H |
| 5.16 | F | —OMe | O | Me | H |
| 5.17 | F | —CH$_2$OMe | O | Me | H |
| 5.18 | F | —CH$_2$CCH | O | Me | H |
| 5.19 | F | —Ph | O | Me | H |
| 5.20 | F | —2-Py | O | Me | H |
| 5.21 | F | —CH$_2$CF$_3$ | O | Me | H |
| 5.22 | F | —cyclopropyl | O | Me | H |
| 5.23 | F | —Ac | O | Me | H |
| 5.24 | F | —(2-thiazoyl) | O | Me | H |
| 5.25 | F | —iPr | O | Me | H |
| 5.26 | F | —(3-thienyl) | O | Me | H |
| 5.27 | F | —(4-F)Ph | O | Me | H |
| 5.28 | F | —(3-F)Ph | O | Me | H |
| 5.29 | F | —(2-F)Ph | O | Me | H |
| 5.30 | F | —(3,5-F)Ph | O | Me | H |
| 5.31 | F | —(2,6-F)Ph | O | Me | H |
| 5.32 | F | —(3,5-CF3)Ph | O | Me | H |
| 5.33 | F | —Me | NH | Me | H |
| 5.34 | F | —OMe | NH | Me | H |
| 5.35 | F | —CH$_2$OMe | NH | Me | H |
| 5.36 | F | —CH$_2$CCH | NH | Me | H |
| 5.37 | F | —Ph | NH | Me | H |
| 5.38 | F | —2-Py | NH | Me | H |
| 5.39 | F | —CH$_2$CF$_3$ | NH | Me | H |
| 5.40 | F | —cyclopropyl | NH | Me | H |
| 5.41 | F | —Ac | NH | Me | H |
| 5.42 | F | —(2-thiazoyl) | NH | Me | H |
| 5.43 | F | —(3-thienyl) | NH | Me | H |
| 5.44 | F | —(4-F)Ph | NH | Me | H |
| 5.45 | F | —(3-F)Ph | NH | Me | H |
| 5.46 | F | —(2-F)Ph | NH | Me | H |
| 5.47 | F | —(3,5-F)Ph | NH | Me | H |
| 5.48 | F | —(2,6-F)Ph | NH | Me | H |
| 5.49 | F | —(3,5-CF3)Ph | NH | Me | H |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.
Ring system:

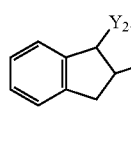
A

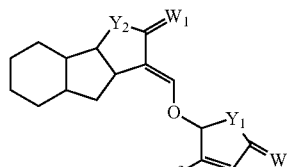
B

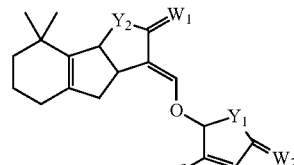
C

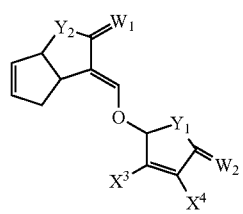
D

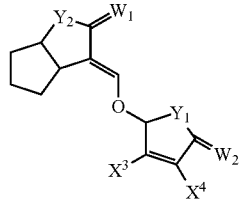
E

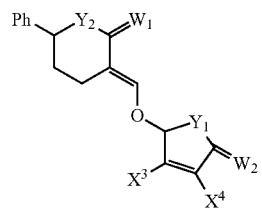
F

| Compound No. | Ring system | $R^5$ | $Y_2$ | $X^3$ | $X^4$ |
|---|---|---|---|---|---|
| 5.50 | F | —Me | NMe | Me | H |
| 5.51 | F | —OMe | NMe | Me | H |
| 5.52 | F | —CH$_2$OMe | NMe | Me | H |
| 5.53 | F | —CH$_2$CCH | NMe | Me | H |
| 5.54 | F | —Ph | NMe | Me | H |
| 5.55 | F | —2-Py | NMe | Me | H |
| 5.56 | F | —CH$_2$CF$_3$ | NMe | Me | H |
| 5.57 | F | —CH(CH$_2$—CH$_2$) | NMe | Me | H |
| 5.58 | F | —Ac | NMe | Me | H |
| 5.59 | F | —(2-thiazoyl) | NMe | Me | H |
| 5.60 | F | —(3-thienyl) | NMe | Me | H |
| 5.61 | F | —(4-F)Ph | NMe | Me | H |
| 5.62 | F | —(3-F)Ph | NMe | Me | H |
| 5.63 | F | —(2-F)Ph | NMe | Me | H |
| 5.64 | F | —(3,5-F)Ph | NMe | Me | H |
| 5.65 | F | —(2,6-F)Ph | NMe | Me | H |
| 5.66 | F | —(3,5-CF3)Ph | NMe | Me | H |
| 5.67 | A | —Me | O | Me | Me |
| 5.68 | A | —OMe | O | Me | Me |
| 5.69 | A | —CH$_2$OMe | O | Me | Me |
| 5.70 | A | —CH$_2$CCH | O | Me | Me |
| 5.71 | A | —Ph | O | Me | Me |
| 5.72 | A | —2-Py | O | Me | Me |
| 5.73 | A | —CH$_2$CF$_3$ | O | Me | Me |
| 5.74 | A | —cyclopropyl | O | Me | Me |
| 5.75 | A | —Ac | O | Me | Me |
| 5.76 | A | —(2-thiazoyl) | O | Me | Me |
| 5.77 | A | —iPr | O | Me | Me |
| 5.78 | A | —(3-thienyl) | O | Me | Me |
| 5.79 | A | —(4-F)Ph | O | Me | Me |
| 5.80 | A | —(3-F)Ph | O | Me | Me |
| 5.81 | A | —(2-F)Ph | O | Me | Me |
| 5.82 | A | —(3,5-F)Ph | O | Me | Me |
| 5.83 | A | —(2,6-F)Ph | O | Me | Me |
| 5.84 | A | —(3,5-CF3)Ph | O | Me | Me |
| 5.85 | A | —Me | NH | Me | Me |
| 5.86 | A | —OMe | NH | Me | Me |
| 5.87 | A | —CH$_2$OMe | NH | Me | Me |
| 5.88 | A | —CH$_2$CCH | NH | Me | Me |
| 5.89 | A | —Ph | NH | Me | Me |
| 5.90 | A | —2-Py | NH | Me | Me |
| 5.91 | A | —CH$_2$CF$_3$ | NH | Me | Me |
| 5.92 | A | —cyclopropyl | NH | Me | Me |
| 5.93 | A | —Ac | NH | Me | Me |
| 5.94 | A | —(2-thiazoyl) | NH | Me | Me |
| 5.95 | A | —(3-thienyl) | NH | Me | Me |
| 5.96 | A | —(4-F)Ph | NH | Me | Me |
| 5.97 | A | —(3-F)Ph | NH | Me | Me |
| 5.98 | A | —(2-F)Ph | NH | Me | Me |
| 5.99 | A | —(3,5-F)Ph | NH | Me | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

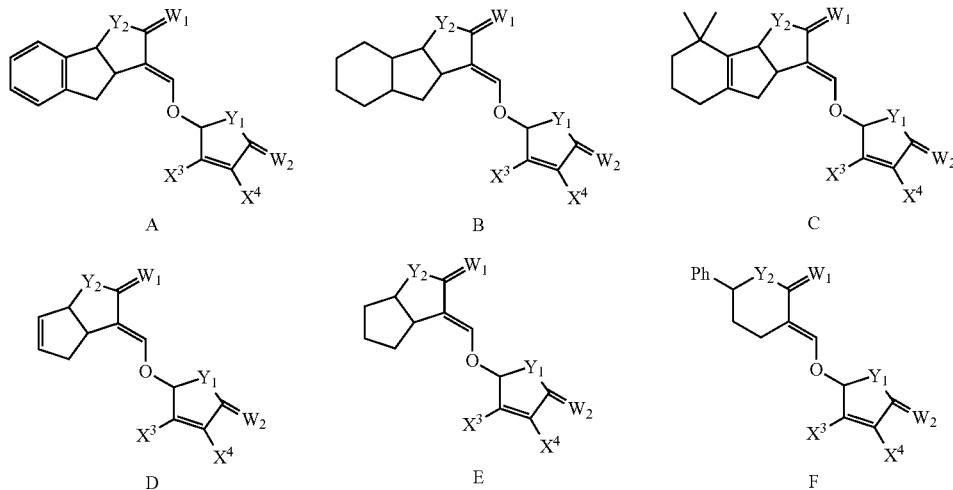

| Compound No. | Ring system | $R^5$ | $Y_2$ | $X^3$ | $X^4$ |
|---|---|---|---|---|---|
| 6.00 | A | —(2,6-F)Ph | NH | Me | Me |
| 6.01 | A | —(3,5-CF3)Ph | NH | Me | Me |
| 6.02 | A | —Me | NMe | Me | Me |
| 6.03 | A | —OMe | NMe | Me | Me |
| 6.04 | A | —CH$_2$OMe | NMe | Me | Me |
| 6.05 | A | —CH$_2$CCH | NMe | Me | Me |
| 6.06 | A | —Ph | NMe | Me | Me |
| 6.07 | A | —2-Py | NMe | Me | Me |
| 6.08 | A | —CH$_2$CF$_3$ | NMe | Me | Me |
| 6.09 | A | —cyclopropyl | NMe | Me | Me |
| 6.10 | A | —Ac | NMe | Me | Me |
| 6.11 | A | —(2-thiazoyl) | NMe | Me | Me |
| 6.12 | A | —(3-thienyl) | NMe | Me | Me |
| 6.13 | A | —(4-F)Ph | NMe | Me | Me |
| 6.14 | A | —(3-F)Ph | NMe | Me | Me |
| 6.15 | A | —(2-F)Ph | NMe | Me | Me |
| 6.16 | A | —(3,5-F)Ph | NMe | Me | Me |
| 6.17 | A | —(2,6-F)Ph | NMe | Me | Me |
| 6.18 | A | —(3,5-CF3)Ph | NMe | Me | Me |
| 6.19 | D | —Me | O | Me | Me |
| 6.20 | D | —OMe | O | Me | Me |
| 6.21 | D | —CH$_2$OMe | O | Me | Me |
| 6.22 | D | —CH$_2$CCH | O | Me | Me |
| 6.23 | D | —Ph | O | Me | Me |
| 6.24 | D | —2-Py | O | Me | Me |
| 6.25 | D | —CH$_2$CF$_3$ | O | Me | Me |
| 6.26 | D | —cyclopropyl | O | Me | Me |
| 6.27 | D | —Ac | O | Me | Me |
| 6.28 | D | —(2-thiazoyl) | O | Me | Me |
| 6.29 | D | —iPr | O | Me | Me |
| 6.30 | D | —(3-thienyl) | O | Me | Me |
| 6.31 | D | —(4-F)Ph | O | Me | Me |
| 6.32 | D | —(3-F)Ph | O | Me | Me |
| 6.33 | D | —(2-F)Ph | O | Me | Me |
| 6.34 | D | —(3,5-F)Ph | O | Me | Me |
| 6.35 | D | —(2,6-F)Ph | O | Me | Me |
| 6.36 | D | —(3,5-CF3)Ph | O | Me | Me |
| 6.37 | D | —Me | NH | Me | Me |
| 6.38 | D | —OMe | NH | Me | Me |
| 6.39 | D | —CH$_2$OMe | NH | Me | Me |
| 6.40 | D | —CH$_2$CCH | NH | Me | Me |
| 6.41 | D | —Ph | NH | Me | Me |
| 6.42 | D | —2-Py | NH | Me | Me |
| 6.43 | D | —CH$_2$CF$_3$ | NH | Me | Me |
| 6.44 | D | —cyclopropyl | NH | Me | Me |
| 6.45 | D | —Ac | NH | Me | Me |
| 6.46 | D | —(2-thiazoyl) | NH | Me | Me |
| 6.47 | D | —(3-thienyl) | NH | Me | Me |
| 6.48 | D | —(4-F)Ph | NH | Me | Me |
| 6.49 | D | —(3-F)Ph | NH | Me | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.

Ring system:

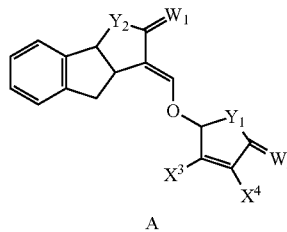

A

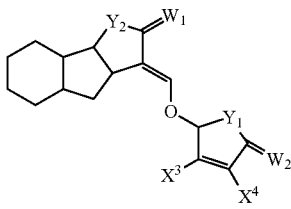

B

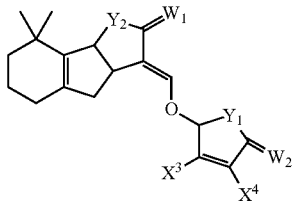

C

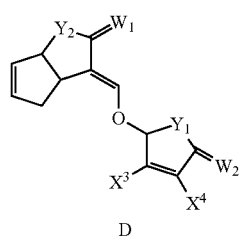

D

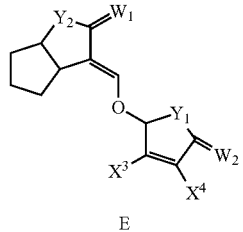

E

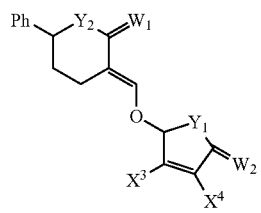

F

| Compound No. | Ring system | $R^5$ | $Y_2$ | $X^3$ | $X^4$ |
|---|---|---|---|---|---|
| 6.50 | D | —(2-F)Ph | NH | Me | Me |
| 6.51 | D | —(3,5-F)Ph | NH | Me | Me |
| 6.52 | D | —(2,6-F)Ph | NH | Me | Me |
| 6.53 | D | —(3,5-CF3)Ph | NH | Me | Me |
| 6.54 | D | —Me | NMe | Me | Me |
| 6.55 | D | —OMe | NMe | Me | Me |
| 6.56 | D | —NCH$_2$OMe | NMe | Me | Me |
| 6.57 | D | —CH$_2$CCH | NMe | Me | Me |
| 6.58 | D | —Ph | NMe | Me | Me |
| 6.59 | D | —2-Py | NMe | Me | Me |
| 6.60 | D | —CH$_2$CF$_3$ | NMe | Me | Me |
| 6.61 | D | —cyclopropyl | NMe | Me | Me |
| 6.62 | D | —Ac | NMe | Me | Me |
| 6.63 | D | —(2-thiazoyl) | NMe | Me | Me |
| 6.64 | D | —(3-thienyl) | NMe | Me | Me |
| 6.65 | D | —(4-F)Ph | NMe | Me | Me |
| 6.66 | D | —(3-F)Ph | NMe | Me | Me |
| 6.67 | D | —(2-F)Ph | NMe | Me | Me |
| 6.68 | D | —(3,5-F)Ph | NMe | Me | Me |
| 6.69 | D | —(2,6-F)Ph | NMe | Me | Me |
| 6.70 | D | —(3,5-CF3)Ph | NMe | Me | Me |
| 6.71 | E | —Me | O | Me | Me |
| 6.72 | E | —OMe | O | Me | Me |
| 6.73 | E | —CH$_2$OMe | O | Me | Me |
| 6.74 | E | —CH$_2$CCH | O | Me | Me |
| 6.75 | E | —Ph | O | Me | Me |
| 6.76 | E | —2-Py | O | Me | Me |
| 6.77 | E | —CH$_2$CF$_3$ | O | Me | Me |
| 6.78 | E | —cyclopropyl | O | Me | Me |
| 6.79 | E | —Ac | O | Me | Me |
| 6.80 | E | —(2-thiazoyl) | O | Me | Me |
| 6.81 | E | —iPr | O | Me | Me |
| 6.82 | E | —(3-thienyl) | O | Me | Me |
| 6.83 | E | —(4-F)Ph | O | Me | Me |
| 6.84 | E | —(3-F)Ph | O | Me | Me |
| 6.85 | E | —(2-F)Ph | O | Me | Me |
| 6.86 | E | —(3,5-F)Ph | O | Me | Me |
| 6.87 | E | —(2,6-F)Ph | O | Me | Me |
| 6.88 | E | —(3,5-CF3)Ph | O | Me | Me |
| 6.89 | E | —Me | NH | Me | Me |
| 6.90 | E | —OMe | NH | Me | Me |
| 6.91 | E | —CH2OMe | NH | Me | Me |
| 6.92 | E | —CH2CCH | NH | Me | Me |
| 6.93 | E | —Ph | NH | Me | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.
Ring system:

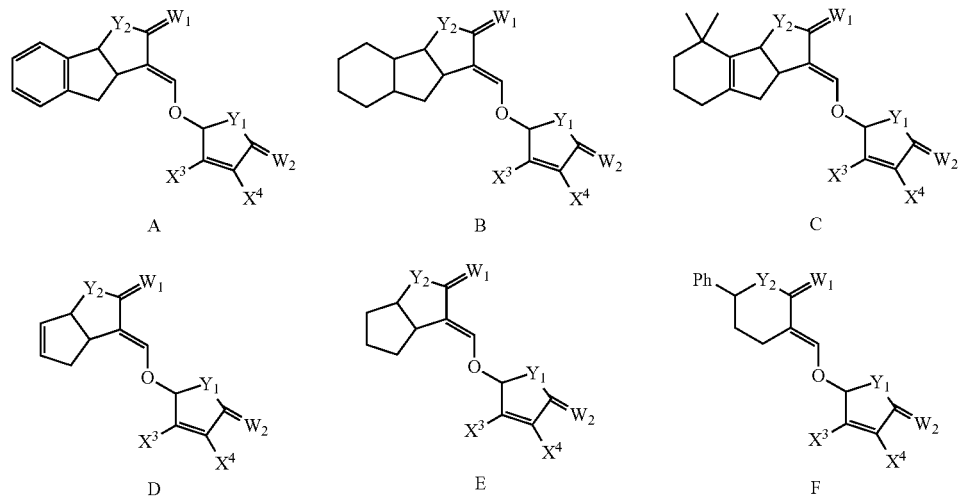

| Compound No. | Ring system | $R^5$ | $Y_2$ | $X^3$ | $X^4$ |
|---|---|---|---|---|---|
| 6.94 | E | —2-Py | NH | Me | Me |
| 6.95 | E | —CH2CF3 | NH | Me | Me |
| 6.96 | E | —cyclopropyl | NH | Me | Me |
| 6.97 | E | —Ac | NH | Me | Me |
| 6.98 | E | —(2-thiazoyl) | NH | Me | Me |
| 6.99 | E | —(3-thienyl) | NH | Me | Me |
| 7.00 | E | —(4-F)Ph | NH | Me | Me |
| 7.01 | E | —(3-F)Ph | NH | Me | Me |
| 7.02 | E | —(2-F)Ph | NH | Me | Me |
| 7.03 | E | —(3,5-F)Ph | NH | Me | Me |
| 7.04 | E | —(2,6-F)Ph | NH | Me | Me |
| 7.05 | E | —(3,5-CF3)Ph | NH | Me | Me |
| 7.06 | E | —Me | NMe | Me | Me |
| 7.07 | E | —OMe | NMe | Me | Me |
| 7.08 | E | —CH$_2$OMe | NMe | Me | Me |
| 7.09 | E | —CH$_2$CCH | NMe | Me | Me |
| 7.10 | E | —Ph | NMe | Me | Me |
| 7.11 | E | —2-Py | NMe | Me | Me |
| 7.12 | E | —CH$_2$CF$_3$ | NMe | Me | Me |
| 7.13 | E | —CH(CH$_2$-CH$_2$) | NMe | Me | Me |
| 7.14 | E | —Ac | NMe | Me | Me |
| 7.15 | E | —(2-thiazoyl) | NMe | Me | Me |
| 7.16 | E | —(3-thienyl) | NMe | Me | Me |
| 7.17 | E | —(4-F)Ph | NMe | Me | Me |
| 7.18 | E | —(3-F)Ph | NMe | Me | Me |
| 7.19 | E | —(2-F)Ph | NMe | Me | Me |
| 7.20 | E | —(3,5-F)Ph | NMe | Me | Me |
| 7.21 | E | —(2,6-F)Ph | NMe | Me | Me |
| 7.22 | E | —(3,5-CF3)Ph | NMe | Me | Me |
| 7.23 | F | —Me | O | Me | Me |
| 7.24 | F | —OMe | O | Me | Me |
| 7.25 | F | —CH$_2$OMe | O | Me | Me |
| 7.26 | F | —CH$_2$CCH | O | Me | Me |
| 7.27 | F | —Ph | O | Me | Me |
| 7.28 | F | —2-Py | O | Me | Me |
| 7.29 | F | —CH$_2$CF$_3$ | O | Me | Me |
| 7.30 | F | —cyclopropyl | O | Me | Me |
| 7.31 | F | —Ac | O | Me | Me |
| 7.32 | F | —(2-thiazoyl) | O | Me | Me |
| 7.33 | F | —iPr | O | Me | Me |
| 7.34 | F | —(3-thienyl) | O | Me | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.
Ring system:

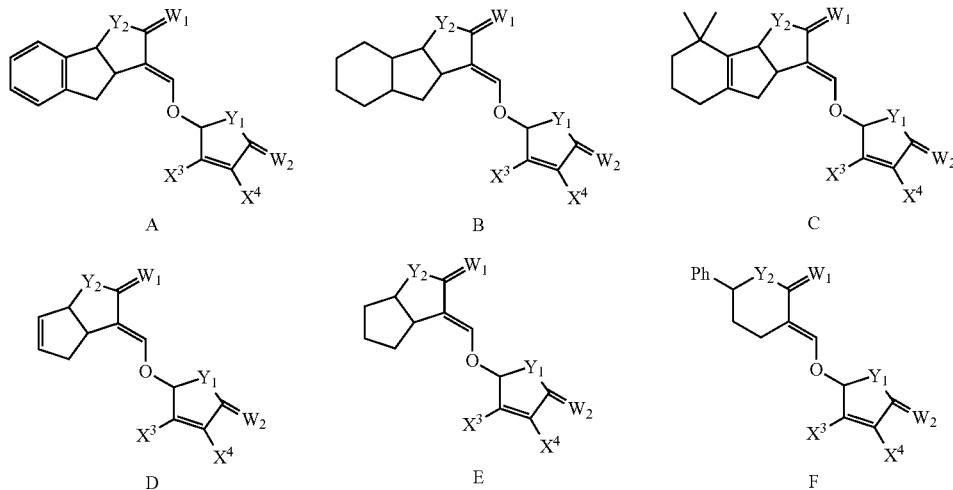

| Compound No. | Ring system | $R^5$ | $Y_2$ | $X^3$ | $X^4$ |
|---|---|---|---|---|---|
| 7.35 | F | —(4-F)Ph | O | Me | Me |
| 7.36 | F | —(3-F)Ph | O | Me | Me |
| 7.37 | F | —(2-F)Ph | O | Me | Me |
| 7.38 | F | —(3,5-F)Ph | O | Me | Me |
| 7.39 | F | —(2,6-F)Ph | O | Me | Me |
| 7.40 | F | —(3,5-CF3)Ph | O | Me | Me |
| 7.41 | F | —Me | NH | Me | Me |
| 7.42 | F | —OMe | NH | Me | Me |
| 7.43 | F | —CH$_2$OMe | NH | Me | Me |
| 7.44 | F | —CH$_2$CCH | NH | Me | Me |
| 7.45 | F | —Ph | NH | Me | Me |
| 7.46 | F | —2-Py | NH | Me | Me |
| 7.47 | F | —CH$_2$CF$_3$ | NH | Me | Me |
| 7.48 | F | —cyclopropyl | NH | Me | Me |
| 7.49 | F | —Ac | NH | Me | Me |
| 7.50 | F | —(2-thiazoyl) | NH | Me | Me |
| 7.51 | F | —(3-thienyl) | NH | Me | Me |
| 7.52 | F | —(4-F)Ph | NH | Me | Me |
| 7.53 | F | —(3-F)Ph | NH | Me | Me |
| 7.54 | F | —(2-F)Ph | NH | Me | Me |
| 7.55 | F | —(3,5-F)Ph | NH | Me | Me |
| 7.56 | F | —(2,6-F)Ph | NH | Me | Me |
| 7.57 | F | —(3,5-CF3)Ph | NH | Me | Me |
| 7.58 | F | —Me | NMe | Me | Me |
| 7.59 | F | —OMe | NMe | Me | Me |
| 7.60 | F | —CH$_2$OMe | NMe | Me | Me |
| 7.61 | F | —CH$_2$CCH | NMe | Me | Me |
| 7.62 | F | —Ph | NMe | Me | Me |
| 7.63 | F | —2-Py | NMe | Me | Me |
| 7.64 | F | —CH$_2$CF$_3$ | NMe | Me | Me |
| 7.65 | F | —CH(CH$_2$—CH$_2$) | NMe | Me | Me |
| 7.66 | F | —Ac | NMe | Me | Me |
| 7.67 | F | —(2-thiazoyl) | NMe | Me | Me |
| 7.68 | F | —(3-thienyl) | NMe | Me | Me |
| 7.69 | F | —(4-F)Ph | NMe | Me | Me |
| 7.70 | F | —(3-F)Ph | NMe | Me | Me |
| 7.71 | F | —(2-F)Ph | NMe | Me | Me |
| 7.72 | F | —(3,5-F)Ph | NMe | Me | Me |
| 7.73 | F | —(2,6-F)Ph | NMe | Me | Me |
| 7.74 | F | —(3,5-CF3)Ph | NMe | Me | Me |
| 7.75 | F | —Me | O | H | Me |
| 7.76 | F | —OMe | O | H | Me |
| 7.77 | F | —CH$_2$OMe | O | H | Me |
| 7.78 | F | —CH$_2$CCH | O | H | Me |
| 7.79 | F | —Ph | O | H | Me |
| 7.80 | F | —2-Py | O | H | Me |
| 7.81 | F | —CH$_2$CF$_3$ | O | H | Me |
| 7.82 | F | —cyclopropyl | O | H | Me |
| 7.83 | F | —Ac | O | H | Me |
| 7.84 | F | —(2-thiazoyl) | O | H | Me |

TABLE 1-continued

Compounds of Formula (I) wherein $W_1$ is O, $W_2$ is O, $Y_1$ is $NR^5$ and the ring system is as shown in Formulae A to F below. $R^5$, $Y_2$, $X_3$ and $X_4$ are as defined in the following table.
Ring system:

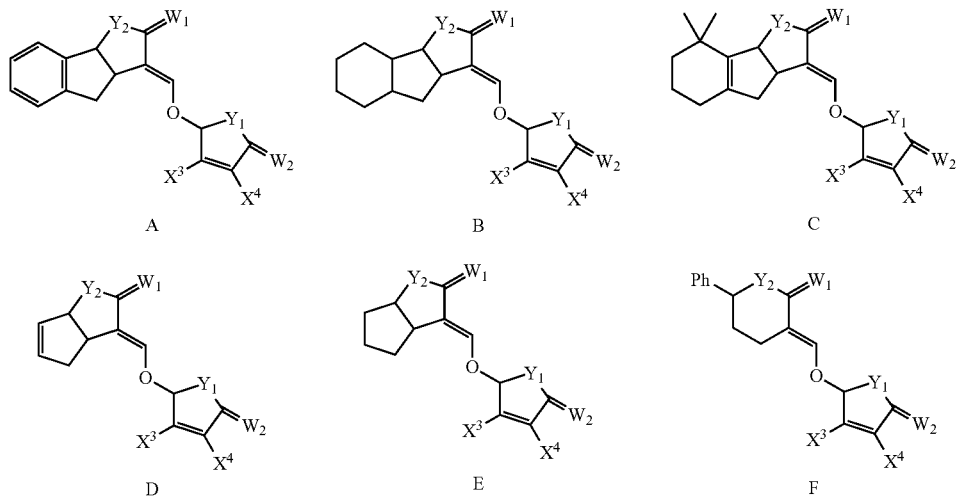

A    B    C

D    E    F

| Compound No. | Ring system | $R^5$ | $Y_2$ | $X^3$ | $X^4$ |
|---|---|---|---|---|---|
| 7.85 | F | —iPr | O | H | Me |
| 7.86 | F | —(3-thienyl) | O | H | Me |
| 7.87 | F | —(4-F)Ph | O | H | Me |
| 7.88 | F | —(3-F)Ph | O | H | Me |
| 7.89 | F | —(2-F)Ph | O | H | Me |
| 7.90 | F | —(3,5-F)Ph | O | H | Me |
| 7.91 | F | —(2,6-F)Ph | O | H | Me |
| 7.92 | F | —(3,5-CF3)Ph | O | H | Me |
| 7.93 | F | —Me | NH | H | Me |
| 7.94 | F | —OMe | NH | H | Me |
| 7.95 | F | —CH$_2$OMe | NH | H | Me |
| 7.96 | F | —CH$_2$CCH | NH | H | Me |
| 7.97 | F | —Ph | NH | H | Me |
| 7.98 | F | —2-Py | NH | H | Me |
| 7.99 | F | —CH$_2$CF$_3$ | NH | H | Me |
| 8.00 | F | —cyclopropyl | NH | H | Me |
| 8.01 | F | —Ac | NH | H | Me |
| 8.02 | F | —(2-thiazoyl) | NH | H | Me |
| 8.03 | F | —(3-thienyl) | NH | H | Me |
| 8.04 | F | —(4-F)Ph | NH | H | Me |
| 8.05 | F | —(3-F)Ph | NH | H | Me |
| 8.06 | F | —(2-F)Ph | NH | H | Me |
| 8.07 | F | —(3,5-F)Ph | NH | H | Me |
| 8.08 | F | —(2,6-F)Ph | NH | H | Me |
| 8.09 | F | —(3,5-CF3)Ph | NH | H | Me |
| 8.10 | F | —Me | NMe | H | Me |
| 8.11 | F | —OMe | NMe | H | Me |
| 8.12 | F | —CH$_2$OMe | NMe | H | Me |
| 8.13 | F | —CH$_2$CCH | NMe | H | Me |
| 8.14 | F | —Ph | NMe | H | Me |
| 8.15 | F | —2-Py | NMe | H | Me |
| 8.16 | F | —CH$_2$CF$_3$ | NMe | H | Me |
| 8.17 | F | —CH(CH$_2$—CH$_2$) | NMe | H | Me |
| 8.18 | F | —Ac | NMe | H | Me |
| 8.19 | F | —(2-thiazoyl) | NMe | H | Me |
| 8.20 | F | —(3-thienyl) | NMe | H | Me |
| 8.21 | F | —(4-F)Ph | NMe | H | Me |
| 8.22 | F | —(3-F)Ph | NMe | H | Me |
| 8.23 | F | —(2-F)Ph | NMe | H | Me |
| 8.24 | F | —(3,5-F)Ph | NMe | H | Me |
| 8.25 | F | —(2,6-F)Ph | NMe | H | Me |
| 8.26 | F | —(3,5-CF3)Ph | NMe | H | Me |

Compounds of formula (I) may be prepared according to the following general reaction schemes, in which the substituents $W_1$, $W_2$, $Y_1$, $Y_2$, $X_1$, $X_2$, $X_3$, $X_4$, $R^1$, $R^2$, and $R^5$, have (unless explicitly stated otherwise) the definitions described hereinbefore.

Reaction Scheme 1

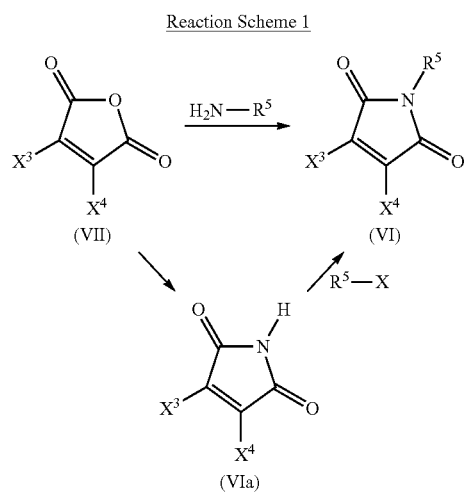

A compound of formula (VI) may be prepared from a compound of formula (VII) by reaction with an amine of formula $R^5NH_2$ or its corresponding salt by heating in an alcoholic solvent.

Alternatively, compound of formula (VI) can be prepared from compound of formula (VIa) by reaction with an alkylating agent of formula $R^5X$ wherein X is a leaving group such as halogen or tosyl, in the presence of a base such as potassium carbonate, eventually in the presence of a catalyst, such as potassium iodide.

Alternatively, compound of formula (VI) can be prepared from compound of formula (VIa) by reaction with a compound of formula $R^5X$ wherein X is an alkoxy group in the presence of a Lewis acid such as tin tetrachloride or boron trifluoride.

A compound of formula (VIa) may be prepared from a compound of formula (VII) by reaction with ammonia or its corresponding ammonium salt. Compounds of formula (VII) are readily available from a variety of commercial sources.

Reaction Scheme 2

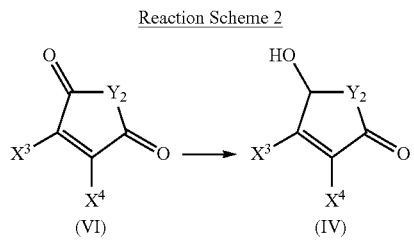

A compound of Formula (IV) may be prepared from compound of Formula (VI) by reaction with a reducing agent such as diisopropylaluminium hydride, sodium cyanoborohydride or sodium borohydride, optionally in the presence of a Lewis acid such as cerium trichloride. Similar reactions have been reported, for example, in *J Chem Soc, Perkin Trans* 1, (2002), 707-709.

Reaction Scheme 3

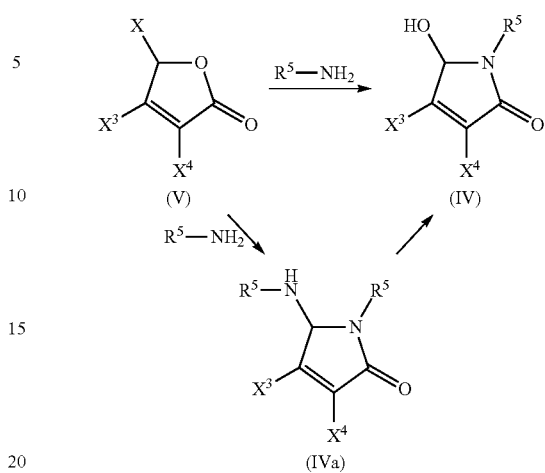

A compound of formula (IV) may also be prepared from compound of formula (V) (wherein X is as a leaving group such as an halogen or tosyl or a mesyl group) by reaction with an amine of formula $R^5NH_2$ or its corresponding hydrochloric salt, in the presence or not of a base and in an alcoholic solvent, such as methanol or ethanol. Similar reactions have been described in *Synthesis* (1973), 167-168 and *Heterocycles* (1983), 1761-1767.

Alternatively, a compound of formula (IV) can be prepared from a compound of formula (IVa) by hydrolysis in the presence or not of an acid such a hydrochloric acid. Compound of formula (IVa) can be accessed from compound of formula (V) by reaction with an excess of amine of formula $R^5NH_2$ or its corresponding hydrochloric salt, in the presence or not of a base and in an alcoholic solvent such as methanol or ethanol.

Compounds of formula (V) can be prepared by a person skilled in the art by methods reported in the literature as in *J Chem Soc Perkin* 1(1981), 1734-1743.

Reaction Scheme 4

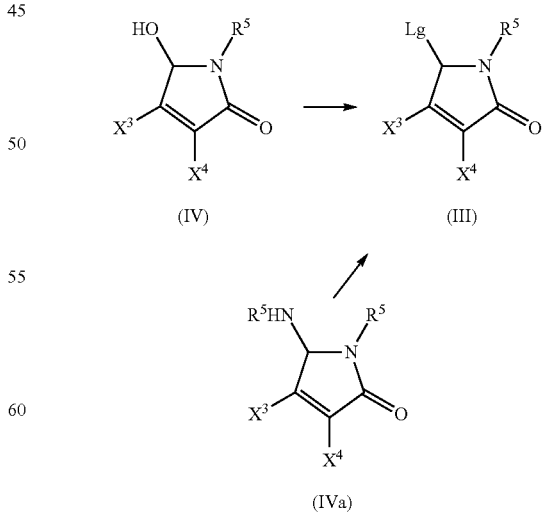

Compounds of formula (III) wherein Lg is a leaving group, such as halogen, may be prepared from compound of formula (IV) or (IVa) by reaction with a chlorinating agent such as thionyl chloride, phosgene or 1-chloro-N,N,2-trimethyl-1-propenylamine or a brominating agent such as PBr₃ or thionyl bromide, in the presence or not of a base such as pyridine.

Compounds of formula (III) wherein Lg is a leaving group such alkylsulfonyl or aryl sulfonyl may be prepared from compound of formula (IV) by reaction with the corresponding alkylsulfonyl chloride or aryl sulfonyl chloride in the presence of a base such as triethyl amine or pyridine.

Reaction Scheme 6

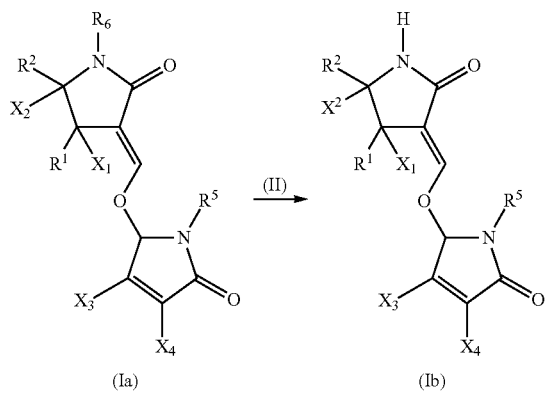

Compounds of formula (Ib) may be prepared from a compound of formula (Ia) wherein $R^6$ is an alkoxycarbonyl group such as tert-butoxycarbonyl, by reaction with an organic or inorganic acid such as trifluoroacetic acid or HCl, or in the presence of a Lewis acid such as a magnesium salt.

Compounds of formula (IV) as described above are particularly useful intermediates for use in the invention, and some of such compounds are novel.

Accordingly, in a further aspect the invention provides the use of a compound of formula (IV)

Reaction Scheme 5

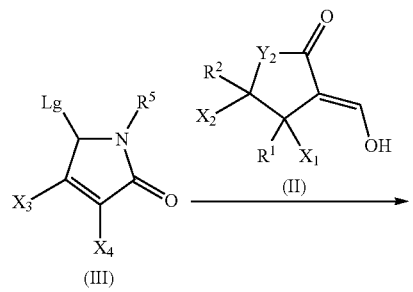

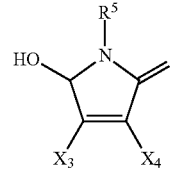

Compounds of formula (Ia) may be prepared from compounds of formula (III) by reaction with a compound of formula (II) in the presence of a base such potassium tert-butylate or sodium tert-butylate, in the presence or not of a crown ether to activate the base. The reaction can also be carried out in the presence of a catalytic or stoichiometric amount of iodine salt, such as potassium iodide or tetrabutyl ammonium iodide.

Compounds of formula (II) can be prepared by a method similar to what is described in WO 12/080115 ($Y_2$=—$(CR^4R^7)_p(CR^3R^8)_nNR^6$—) and GB 1 591 374 ($Y_2$=O).

wherein $R^5$ is hydrogen, $C_1$-$C_6$ alkoxy, hydroxyl, amine, N—$C_1$-$C_6$alkylamine, N,N-di-$C_1$-$C_6$ alkylamine, substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_2$-$C_6$ alkynyl, substituted or unsubstituted $C_1$-$C_8$ alkylcarbonyl, substituted or unsubstituted $C_1$-$C_8$ alkoxycarbonyl, substituted or unsubstituted aryl, substituted or unsubstituted heteroaryl, substituted or unsubstituted heterocyclyl, or substituted or unsubstituted benzyl; and, $X^3$ and $X^4$ are each independently selected from H, $C_1$-$C_6$ alkyl, $C_2$-$C_3$alkynyl, $C_1$-$C_6$ haloalkyl, halogen, hydroxyl, $C_1$-$C_6$ alkoxy, $C_1$-$C_6$ alkylsulfinyl, $C_1$-$C_6$ alkylsulfonyl, $C_1$-$C_6$ alkylthio; or $X^3$ and $X^4$ together with the carbon atoms to which they are attached form a $C_5$- or $C_6$-cycloalkyl, as an intermediate in the production of a compound of formula (I) as defined herein.

In yet a further aspect there is provided a compound of formula (IV-i) (i.e. compound of formula (IV) wherein $X_3$ is H),

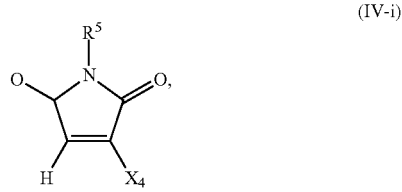

(IV-i)

wherein $R^5$ is $C_1$-$C_6$ alkoxy, hydroxyl, amine, N—$C_1$-$C_6$ alkylamine, N,N-di-$C_1$-$C_6$ alkylamine, substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_2$-$C_6$ alkynyl, substituted or unsubstituted $C_1$-$C_8$ alkylcarbonyl, substituted or unsubstituted $C_1$-$C_8$ alkoxycarbonyl, substituted or unsubstituted aryl, substituted or unsubstituted heteroaryl, substituted or unsubstituted heterocyclyl, or substituted or unsubstituted benzyl; and, $X^4$ is selected from $C_1$-$C_6$ alkyl, $C_2$-$C_3$alkynyl, $C_1$-$C_6$ haloalkyl, halogen, hydroxyl, $C_1$-$C_6$ alkoxy, $C_1$-$C_6$ alkylsulfinyl, $C_1$-$C_6$ alkylsulfonyl, $C_1$-$C_6$ alkylthio;

with the proviso that the compound of formula (IV-i) is not one of the following compounds:

2,5-dihydro-5-hydroxy-3-methyl-2-oxo-1H-pyrrole-1-carboxaldehyde;
1,5-dihydro-5-hydroxy-3-methyl-1-(2-propen-1-yl)-2H-pyrrol-2-one;
1,5-dihydro-5-hydroxy-3-methyl-1-(phenylmethyl)-2H-pyrrol-2-one;
1,5-dihydro-5-hydroxy-3-methyl-1-phenyl-2H-pyrrol-2-one;
1,5-dihydro-5-hydroxy-3-methyl-1-(4-methoxyphenyl)-2H-pyrrol-2-one;
1,5-dihydro-5-hydroxy-3-methyl-1-(4-methoxybenzyl)-2H-pyrrol-2-one;
2,5-dihydro-5-hydroxy-3-methyl-2-oxo-1H-pyrrole-1-carboxylic acid, −1,1-dimethylethyl ester;
3-bromo-1,5-dihydro-5-hydroxy-1-methyl-2H-pyrrol-2-one;
3-chloro-1,5-dihydro-5-hydroxy-1-(phenylmethyl)-2H-pyrrol-2-one, or
1,5-dihydro-5-hydroxy-3-methyl-1-((4-methoxyphenyl)ethyl)-2H-pyrrol-2-one.

The skilled person will appreciate that the preferred options for substituents $R^5$, $X_3$ and $X_4$ in a compound of formula (IV) are as described above with respect to a compound of formula (I). In one particular set of embodiments of compounds of formula (IV), $R^5$ is selected from phenyl, methoxy, cyclopropyl, 2-trifluoroethyl, 3-fluorophenyl, 4-fluorophenyl or 3,5-(trifluoromethyl)phenyl and $X_4$ is methyl.

The compounds of Formula (I) according to the invention can be used as plant growth regulators or seed germination promoters by themselves, but they are generally formulated into plant growth regulation or seed germination promotion compositions using formulation adjuvants, such as carriers, solvents and surface-active agents (SFAs). Thus, the present invention further provides a plant growth regulator composition comprising a plant growth regulation compound of Formula (I) and an agriculturally acceptable formulation adjuvant.

The present invention further provides a plant growth regulator composition consisting essentially of a plant growth regulation compound of Formula (I) and an agriculturally acceptable formulation adjuvant.

The present invention further provides a plant growth regulator composition consisting of a plant growth regulation compound of Formula (I) and an agriculturally acceptable formulation adjuvant. The present invention further provides a seed germination promoter composition comprising a seed germination promoter compound of Formula (I) and an agriculturally acceptable formulation adjuvant.

The present invention further provides a seed germination promoter composition consisting essentially of a seed germination promoter compound of Formula (I) and an agriculturally acceptable formulation adjuvant. The present invention further provides a seed germination promoter composition consisting of a seed germination promoter compound of Formula (I) and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of Formula (I) and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention still further provides a method for regulating the growth of plants in a locus, wherein the method comprises application to the locus of a plant growth regulating amount of a composition according to the present invention.

The present invention also provides a method for promoting the germination of seeds, comprising applying to the seeds, or to a locus containing seeds, a seed germination promoting amount of a composition according to the present invention.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound of Formula (I) or composition of the present invention may be applied to a plant, part of the plant, plant organ, plant propagation material or a surrounding area thereof.

In one embodiment, the invention relates to a method of treating a plant propagation material comprising applying to the plant propagation material a composition of the present invention in an amount effective to promote germination and/or regulate plant growth. The invention also relates to a plant propagation material treated with a compound of Formula (I) or a composition of the present invention. Preferably, the plant propagation material is a seed.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of formula (I) may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence.

The rates of application of compounds of Formula (I) may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of Formula (I) according to the invention are generally applied at a rate of from 1 to 2000 g/ha, especially from 5 to 1000 g/ha. For seed treatment the rate of application is generally between 0.0005 and 150 g per 100 kg of seed.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

The invention may also be used to regulate the growth, or promote the germination of seeds of non-crop plants, for example to facilitate weed control by synchronizing germination. Thus, the invention also covers a method for controlling weeds comprising applying to a locus containing weed seeds a seed germination promoting amount of a composition or a compound according to the invention, allowing the seeds to germinate, and then applying to the locus a post-emergence herbicide.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rending crop plants tolerant to HPPD-inhibitors are known, for example from WO0246387; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colweffiana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle).

Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Further according to the invention, there is provided the use of a compound of Formula (I), or a salt or N-oxide thereof, or of a composition thereof, for promoting the germination of seeds and/or for regulating plant growth. Preferably, when the use is for the germination of seeds, it is for maize (corn) seeds. Preferably, this use is for the germination of seeds (eg, maize seeds) at temperatures of between 10 and 20° C., and more preferably, at temperatures between 13 and 17° C., and most preferably at a temperature of about 15° C.

Compounds and compositions of the present invention may be applied in combination with other active ingredients or products for use in agriculture, including insecticides, fungicides, herbicides, plant growth regulators, crop enhancing compounds, nutrients, and biologicals. Examples of such mixing partners may be found in the Pesticide manual, 16th edition (published by the British Crop Protection Council). Such mixtures may be applied to a plant, plant propagation material or plant growing locus, either simultaneously (e.g. as a pre-formulated mixture, or a tank mix), or sequentially in a suitable timescale. Co-application of pesticides with the present invention has the added benefit of minimising farmer time spent applying products to crops.

Various aspects and embodiments of the present invention will now be illustrated in more detail by way of example. It will be appreciated that modification of detail may be made without departing from the scope of the invention.

PREPARATION EXAMPLES

The following abbreviations are used throughout this section: s=singlet; bs=broad singlet; d=doublet; dd=double doublet; dt=double triplet; t=triplet; tt=triple triplet, q=quartet, m=multiplet; Me=methyl; Et=ethyl; Pr=propyl; Bu=butyl; mp=melting point; DMF=N,N-dimethylformamide, THF=tetrahydrofuran.

The following HPLC-MS methods was used for the analysis of the compounds:

Method A: Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 μm, 30×2.1 mm, Temp: 60° C., flow rate 0.85 mL/min; DAD Wavelength range (nm): 210 to 500) Solvent Gradient: A=H$_2$O+5% MeOH+0.05% HCOOH, B=Acetonitrile+0.05% HCOOH) gradient: 0 min 10% B; 0-1.2 min 100% B; 1.2-1.50 min 100% B.

Method B: Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 μm, 30×2.1 mm, Temp: 60° C., flow rate 0.85 mL/min; DAD Wavelength range (nm): 210 to 500) Solvent Gradient: A=H$_2$O+5% MeOH+0.05% HCOOH, B=Acetonitrile+0.05% HCOOH) gradient: 0 min 10% B; 0-2.7 min 100% B; 2.7-3.0 min 100% B.

Part I: Preparation of Hydroxypyrrol-5-One (Formula IV)

Example P1-1: Preparation of 2-hydroxy-1-(methoxymethyl)-4-methyl-2H-pyrrol-5-one (compound IV-1)

Step 1: Preparation of 1-(methoxymethyl)-3-methyl-pyrrole-2,5-dione (compound VI-1)

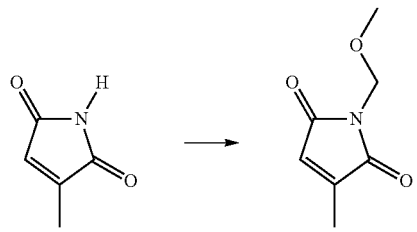

To a solution of 3-methylpyrrole-2,5-dione (4.50 mmol, 0.500 g, as prepared in *European Journal of Organic Chemistry* (2008), 9, 1511-1516) in dimethoxymethane (20 mL) under nitrogen was added slowly tin(IV) chloride (5.40 mmol, 0.632 mL). The reaction mixture was heated to 40° C. for 5 hours (h) and then cooled down to room temperature. The reaction mixture was then carefully neutralized with a saturated solution of potassium carbonate and extracted with ethyl acetate (3×20 mL). The organic phase was dried and evaporated giving 1-(methoxymethyl)-3-methyl-pyrrole-2,5-dione (compound VI-1) as a white solid (657 mg, 94%). $^1$H NMR (400 MHz, CDCl$_3$): δ (ppm) 6.44 (1H, s), 4.89 (2H, s), 3.35 (3H, s), 2.13 (3H, s).

Step 2: Preparation of 2-hydroxy-1-(methoxymethyl)-4-methyl-2H-pyrrol-5-one (compound IV-1)

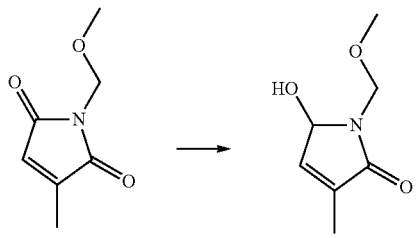

To a solution of 1-(methoxymethyl)-3-methyl-pyrrole-2,5-dione (compound VI-1; 200 mg, 1.28 mmol) in THF (10 mL), was added at −78° C. and under nitrogen diiso-propyl aluminium hydride (1 M in dichloromethane, 1.54 mmol, 1.54 mL). The solution was stirred at −78° C. for 2 h and the reaction was then quenched a saturated solution of Rochelle's salt. The solution was then extracted with ethyl acetate (3×30 mL) and washed with a saturated solution of Rochelle's salt and brine. The organic phase was dried and evaporated to give a brown oil, which was further purified by flash chromatography (20% to 100% ethyl acetate in cyclohexane). The desired product was obtained as a colourless oil, 2-hydroxy-1-(methoxymethyl)-4-methyl-2H-pyrrol-5-one (compound IV-1, 28%, 57 mg). $^1$H NMR (400 MHz, CDCl$_3$): δ (ppm) 6.65 (1H, s), 5.50 (1H, d), 4.90 (1H, d), 4.73 (1H, d), 3.97 (1H, d), 3.33 (3H, s), 1.90 (3H, s).

Example P1-2: Preparation of 2-hydroxy-1-methoxy-4-methyl-2H-pyrrol-5-one (compound IV-3)

Step 1

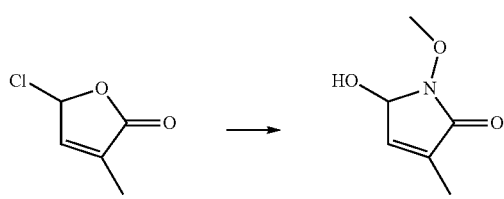

To a solution of 2-chloro-4-methyl-2H-furan-5-one (prepared according to Johnson & all, *J Chem Soc Perkin I* (1981), 1734-1743, 200 mg, 1.50 mmol) in methanol (8 mL) was added methoxyamine hydrochloride (25 mass % in water, 1.88 mmol, 0.57 mL) and sodium acetate (125 mg, 1.50 mmol). The reaction mixture was stirred for 4 h and another equivalent of methoxyamine hydrochloride and sodium acetate were added and then the same again after 7 h. The reaction mixture was stirred for another 12 h. Brine was added and the reaction mixture was extracted with ethyl acetate. The organic phase was dried, evaporated and purified by flash chromatography (20% to 100% ethyl acetate in cyclohexane) to give 2-hydroxy-1-methoxy-4-methyl-2H-pyrrol-5-one (compound IV-3, 103 mg, 47%). $^1$H NMR (400 MHz, CDCl$_3$): δ (ppm) 6.47 (1H, s), 5.47 (1H, s), 3.93 (3H, s), 1.91 (3H, s).

A similar procedure was used to prepare compounds:
1-cyclopropyl-2-(cyclopropylamino)-4-methyl-2H-pyrrol-5-one (compound IV-5; $^1$H NMR (400 MHz, CDCl$_3$): δ (ppm) 6.49 (1H, s), 5.22 (1H, brs), 3.61 (1H, brs), 2.61 (1H, m), 1.83 (3H, s), 1.01-0.66 (4H, m).
2-hydroxy-4-methyl-1-prop-2-ynyl-2H-pyrrol-5-one (compound IV-6; $^1$H NMR (400 MHz, CDCl$_3$): δ (ppm) 6.65 (1H, s), 5.52 (1H, d), 4.53 (1H, d), 4.02 (1H, d), 2.27 (1H, s), 2.20 (1H, d), 1.94 (3H, s).

Example P1-3: Preparation of 2-hydroxy-4-methyl-1-(2,2,2-trifluoroethyl)-2H-pyrrol-5-one (compound IV-7)

Step 1: Preparation of 4-methyl-1-(2,2,2-trifluoroethyl)-2-(2,2,2-trifluoroethylamino)-2H-pyrrol-5-one (compound IVa-7)

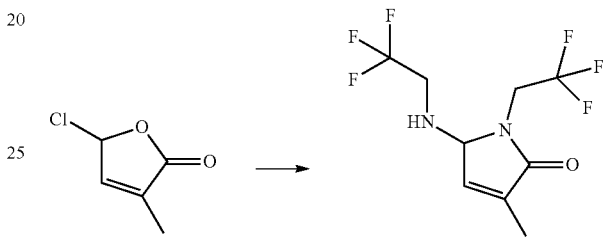

To a solution of 2-chloro-4-methyl-2H-furan-5-one (1.0 g, 7.54 mmol, prepared according to Johnson & all, *J Chem Soc Perkin I* (1981), 1734-1743) in methanol (8 mL) was added sodium acetate (4.38 g, 52.8 mmol) and 2,2,2-trifluoroethylamine hydrochloride salt (7.30 g) were added. The reaction mixture was stirred over 2 days at room temperature. The reaction mixture was then filtered and concentrated until a precipitation was observed again. The mixture was diluted with brine and extracted twice with ethyl acetate. The combined organic layers were dried over Na$_2$SO$_4$ and concentrated to give the intermediate the title compound (2.25 g, quant) which was used without purification in the next step. $^1$H NMR (400 MHz, CDCl3) δ (ppm) 1.92-1.98 (m, 3H) 2.93-3.13 (m, 2H) 3.69-3.82 (m, 1H) 4.21-4.35 (m, 1H) 5.01 (s, 1H) 6.63 (t, 1H).

Step 2: 2-hydroxy-4-methyl-1-(2,2,2-trifluoroethyl)-2H-pyrrol-5-one (compound IV-7)

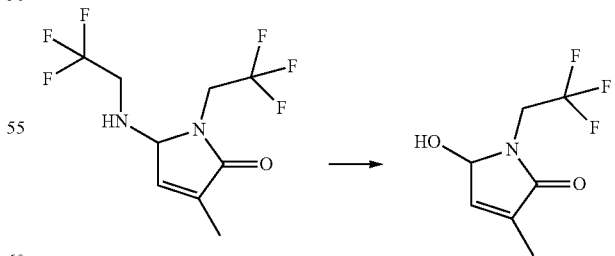

4-Methyl-1-(2,2,2-trifluoroethyl)-2-(2,2,2-trifluoroethylamino)-2H-pyrrol-5-one (1.00 g, 3.43 mmol) was dissolved in 1,4-dioxane (30 mL, 3.43 mmol) and hydrogen chloride (0.688 mL, 6.88 mmol) was added. The reaction mixture was heated to 60° C. overnight and was diluted with ethyl acetate and washed with water and brine. The organic layers were combined, dried over Na$_2$SO$_4$ and the solvent was evaporated to give the crude product (665 mg) as a yellow oil which was purified by column chromatography to give 2-hydroxy-4-methyl-1-(2,2,2-trifluoroethyl)-2H-pyrrol-5-one (compound IV-7, 0.128 g, 19%) as a white solid. M.p.: 98-101° C.; $^1$H NMR (400 MHz, CDCl$_3$): δ ppm 1.83-2.00 (m, 3H), 3.05-3.21 (d, 1H), 3.79 (dq, 1H) 4.22 (dq, 1H), 5.39-5.56 (d, 1H), 6.68 (t, 1H).

Example P1-4: 2-hydroxy-3,4-dimethyl-1-(2,2,2-trifluoroethyl)-2H-pyrrol-5-one (compound IV-8)

Step 1: Preparation of 3,4-dimethyl-1-(2,2,2-trifluoroethyl)pyrrole-2,5-dione (compound VI-8)

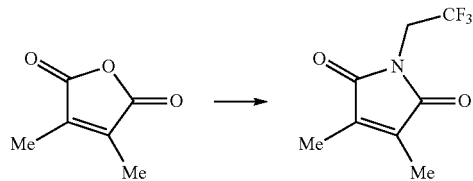 [SMILES: CC1=C(C)C(=O)OC1=O ; CC1=C(C)C(=O)N(CC(F)(F)F)C1=O]

2,3-Dimethylmaleic anhydride (2 g, 15.5 mmol) was dissolved in toluene (30 mL). 2,2,2-Trifluoroethylamine (2.524 mL, 31.0 mmol) was added followed by p-toluenesulfonic acid (0.267 g, 1.55 mmol) was added and the reaction mixture was heated to reflux overnight. A spatula tip of p-toluenesulfonic acid and 0.5 mL of 2,2,2-trifluoroethylamine was added and the reaction mixture was further for 6 h. The reaction mixture was diluted with ethyl acetate and washed twice with saturated NaHCO$_3$ solution and then with brine. The organic layer was dried over Na$_2$SO$_4$ and the solvent was evaporated to give a clear oil (2.90 g, quant.), which was used without further purification; $^1$H NMR (CDCl$_3$, 400 MHz): δ ppm 4.10 (q, 2H), 2.02 (s, 6H);

Step 2: Preparation of 2-hydroxy-3,4-dimethyl-1-(2,2,2-trifluoroethyl)-2H-pyrrol-5-one (compound IV-8)

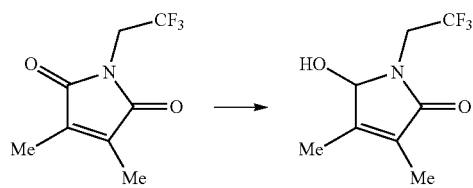 [SMILES: CC1=C(C)C(=O)N(CC(F)(F)F)C1=O ; CC1=C(C)C(O)N(CC(F)(F)F)C1=O]

3,4-Dimethyl-1-(2,2,2-trifluoroethyl)pyrrole-2,5-dione (2.609 g, 12.6 mmol) was dissolved in methanol (13 mL) and cooled to 0° C. Sodium borohydride (0.486 g, 12.6 mmol) was added portion wise and the mixture was stirred for 20 minutes. Water was then added slowly followed by ethyl acetate. The aqueous layer was extracted with ethyl acetate, the organic layers were combined, dried over Na$_2$SO$_4$ and the solvent evaporated to give the crude product (2.42 g, 92%) as a white solid. The product was used as such without further purification. $^1$H NMR (CDCl$_3$, 400 MHz): δ ppm 5.25 (d, 1H), 4.18 (dd, 1H), 3.71-3.83 (m, 1H), 3.47 (d, 1H), 2.00 (s, 3H), 1.78 (t, 3H).

A similar procedure was used to prepare the compound: 2-hydroxy-3,4-dimethyl-3-thienyl-5-yl-2H-pyrrol-5-one (compound IV-15); $^1$H NMR (400 MHz, CDCl$_3$): δ ppm 7.52 (dd, 1H), 7.48 (dd, 1H), 7.27 (dd, 1H), 5.46 (d, 1H), 3.11 (d, 1H), 2.01 (s, 3H), 1.60 (s, 3H).

2-hydroxy-3,4-dimethyl-1-pyrimidin-5-yl-2H-pyrrol-5-one (compound IV-16); 1H NMR (400 MHz, CDCl$_3$): δ ppm 1.92 (m, 3H), 2.11 (s, 3H), 5.70 (s, 1H), 8.97 (s, 1H), 9.24 (s, 2H).

Part II: Preparation of Strigolactone Derivatives from Hydroxypyrrol-5-One (Compound IV)

Example P2-1: Step 1: 2-chloro-1-(methoxymethyl)-4-methyl-2H-pyrrol-5-one (compound III-1)

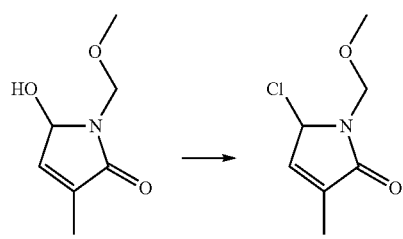

To a solution of 2-hydroxy-1-(methoxymethyl)-4-methyl-2H-pyrrol-5-one (compound IV-1, 0.147 g, 0.93 mmol) in dichloromethane (5 mL) under argon was added 1-chloro-N,N,2-trimethyl-1-propenylamine (0.168 mL, 1.21 mmol). The reaction mixture was stirred at room temperature for 2 h and was concentrated in vacuo to give an oil containing the desired product in mixture with N,N-2-trimethylpropanamide. 2-chloro-1-(methoxymethyl)-4-methyl-2H-pyrrol-5-one (compound III-1, 0.274 g, 91%, 55% purity) was used as such for the next step. $^1$H NMR (400 MHz, CDCl$_3$): δ ppm 6.80 (1H, s), 6.02 (1H, s), 5.08 (1H, d), 4.70 (1H, d), 3.30 (3H, s), 1.98 (3H, s).

A similar procedure was used to prepare compounds:

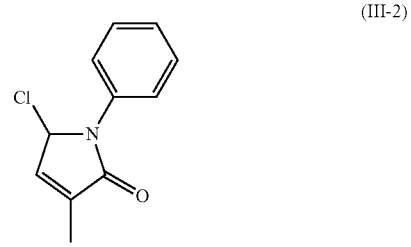

(III-2)

2-chloro-4-methyl-1-phenyl-2H-pyrrol-5-one (compound III-2) from known 2-hydroxy-4-methyl-1-phenyl-2H-pyrrol-5-one (*Bioorganic & Medicinal Chemistry* (2011), 19(9), 2823-2834); $^1$H NMR (400 MHz, CDCl$_3$): δ ppm 2.03 (t, 3H), 6.35 (s, 1H), 6.85 (s, 1H), 7.25 (t, 1H), 7.44 (t, 2H) 7.60 (d, 2H)).

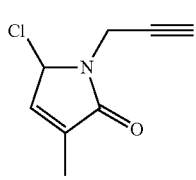

(III-6)

2-chloro-4-methyl-1-prop-2-ynyl-2H-pyrrol-5-one (compound III-6); 1H NMR (400 MHz, CDCl₃): δ ppm 1.96 (t, 3H), 2.26 (t, 1H), 3.88 (dd, 1H), 4.68 (dd, 1H), 6.04 (s, 1H), 6.77 (s, 1H))

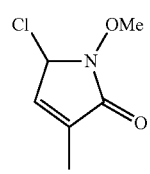

(III-3)

2-chloro-4-methyl-1-methoxy-2H-pyrrol-5-one (compound III-3); 1H NMR (400 MHz, CDCl₃): δ ppm 1.92 (s, 3H), 3.99 (s, 3H), 5.95 (s, 1H), 6.55 (s, 1H)).

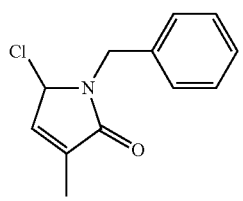

(III-4)

2-chloro-4-methyl-1-benzyl-2H-pyrrol-5-one (compound III-4) from known 2-hydroxy-4-methyl-1-benzyl-2H-pyrrol-5-one (*Bioorganic & Medicinal Chemistry* 2011, 19(9), 2823-2834); ¹H NMR (400 MHz, CDCl₃): δ ppm 1.98 (s, 3H), 4.16 (d, 1H), 5.16 (1H, d), 5.62 (s, 1H), 6.70 (s, 1H), 7.30-7.36 (m, 5H)

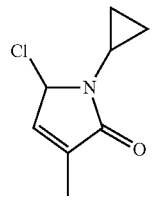

(III-5)

2-chloro-4-methyl-1-cyclopropyl-2H-pyrrol-5-one (compound III-5); ¹H NMR (400 MHz, CDCl₃): δ ppm 0.56-1.07 (m, 4H), 1.90 (s, 3H), 2.54-2.71 (m, 1H), 5.77 (s, 1H), 6.65 (s, 1H)).

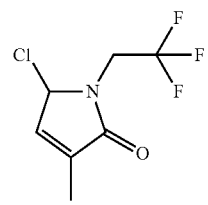

(III-7)

2-chloro-4-methyl-1-(2,2,2-trifluoroethyl)-2H-pyrrol-5-one (compound III-7) from 2-hydroxy-4-methyl-1-(2,2,2-trifluoroethyl)-2H-pyrrol-5-one (compound IV-7) or from 4-methyl-1-(2,2,2-trifluoroethyl)-2-(2,2,2-trifluoroethylamino)-2H-pyrrol-5-one (compound IVa-7): ¹H NMR (400 MHz, CDCl₃): δ ppm 1.97-2.00 (m, 3H), 3.58-3.79 (m, 1H), 4.37-4.61 (m, 1H), 6.00 (s, 1H), 6.85 (m, 1H).

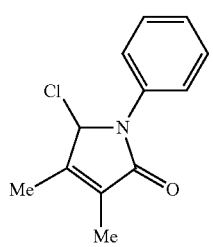

(III-8)

2-chloro-3,4-dimethyl-1-phenyl-2H-pyrrol-5-one (compound III-8) from known 2-hydroxy-3,4-dimethyl-1-phenyl-2H-pyrrol-5-one (Takabe et al, *J Chem Soc, Perkin Trans* 1, 2002, 707-709); ¹H NMR (400 MHz, CDCl₃): δ ppm 1.95 (s, 3H), 2.15 (s, 3H), 6.18 (s, 1H), 7.15-7.26 (t, 1H), 7.35-7.48 (t, 2H), 7.56-7.68 (d, 2H).

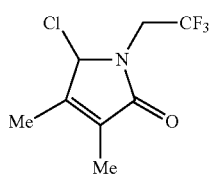

(III-9)

2-chloro-3,4-dimethyl-1-(2,2,2-trifluoroethyl)-2H-pyrrol-5-one (compound III-9) from 2-hydroxy-3,4-dimethyl-1-(2,2,2-trifluoroethyl)-2H-pyrrol-5-one (compound IV-8); ¹H NMR (400 MHz, CDCl₃): δ ppm 1.89-1.93 (m, 3H), 2.09 (s, 3H), 3.61-3.77 (m, 1H), 4.51 (m, 1H), 5.84 (s, 1H).

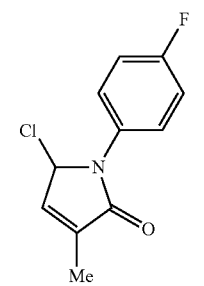

(III-10)

2-chloro-4-methyl-1-(4-fluoro-phenyl)-2H-pyrrol-5-one (compound III-10) from 2-hydroxy-4-methyl-1-(4-fluoro-phenyl)-2H-pyrrol-5-one (compound IV-9) (as described in *Bioorganic & Medicinal Chemistry* (2011), 19(9), 2823-2834); $^1$H NMR (400 MHz, CDCl$_3$): δ ppm 2.01 (m, 3H), 6.28 (m, 1H), 6.83 (m, 1H), 7.08-7.14 (m, 2H), 7.50-7.55 (m, 2H).

19(9), 2823-2834); $^1$H NMR (400 MHz, CDCl$_3$): δ ppm 2.02 (m, 3H), 6.24 (m, 1H), 6.66 (dt, 1H), 6.86 (m, 1H), 7.29-7.36 (m, 2H).

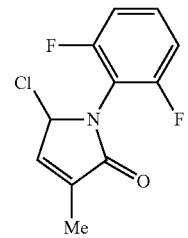

(III-14)

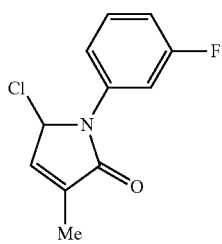

(III-11)

2-chloro-4-methyl-1-(2,6-difluoro-phenyl)-2H-pyrrol-5-one (compound III-14) from 2-hydroxy-4-methyl-1-(2,6-difluoro-phenyl)-2H-pyrrol-5-one (compound IV-13) (as described in *Bioorganic & Medicinal Chemistry* (2011), 19(9), 2823-2834); $^1$H NMR (400 MHz, CDCl$_3$): δ ppm 2.04 (m, 3H), 6.28 (m, 1H), 6.93 (m, 1H), 6.98-7.09 (m, 2H), 7.36 (m, 1H).

2-chloro-4-methyl-1-(3-fluoro-phenyl)-2H-pyrrol-5-one (compound III-11) from 2-hydroxy-4-methyl-1-(3-fluoro-phenyl)-2H-pyrrol-5-one (compound IV-10) (as described in *Bioorganic & Medicinal Chemistry* (2011), 19(9), 2823-2834); $^1$H NMR (400 MHz, CDCl$_3$): δ ppm 2.01 (m, 3H), 6.30 (m, 1H), 6.85 (m, 1H), 6.88-6.96 (m, 1H), 7.33-7.39 (m, 2H), 7.53 (m, 1H).

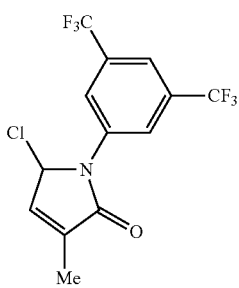

(III-15)

(III-12)

2-chloro-4-methyl-1-(3,5-bistrifluoromethyl-phenyl)-2H-pyrrol-5-one (compound III-15) from 2-hydroxy-4-methyl-1-(3,5-bistrifluoromethyl-phenyl)-2H-pyrrol-5-one (compound IV-14) (as described in *Bioorganic & Medicinal Chemistry* (2011), 19(9), 2823-2834); $^1$H NMR (400 MHz, CDCl$_3$): δ ppm 2.04 (s, 3H), 6.39 (s, 1H), 6.93 (s, 1H), 7.71 (s, 1H), 8.21 (s, 2H).

2-chloro-4-methyl-1-(2-fluoro-phenyl)-2H-pyrrol-5-one (compound III-12) from 2-hydroxy-4-methyl-1-(2-fluoro-phenyl)-2H-pyrrol-5-one (compound IV-11) (as described in *Bioorganic & Medicinal Chemistry* (2011), 19(9), 2823-2834); $^1$H NMR (400 MHz, CDCl$_3$): δ ppm 2.07 (m, 3H), 6.42 (m, 1H), 6.92 (m, 1H), 7.18-7.30 (m, 2H), 7.34-7.41 (m, 1H), 7.51 (m, 1H).

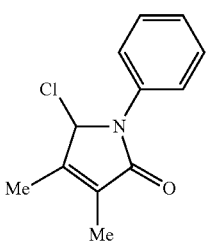

(III-16)

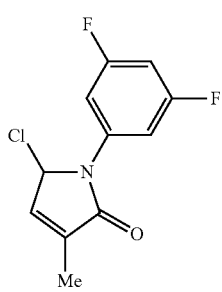

(III-13)

2-chloro-3,4-dimethyl-1-phenyl-2H-pyrrol-5-one (compound III-16) from known 2-hydroxy-3,4-dimethyl-1-phenyl-2H-pyrrol-5-one (*J Med Chem* (2009), 52, 7410-7420); $^1$H NMR (400 MHz, CDCl$_3$): δ ppm 1.91 (s, 3H), 2.11 (s, 3H), 6.17 (s, 1H), 7.21 (t, 1H), 7.40 (t, 2H), 7.56-7.61 (m, 2H).

2-chloro-4-methyl-1-(3,5-difluoro-phenyl)-2H-pyrrol-5-one (compound III-13) from 2-hydroxy-4-methyl-1-(3,5-difluoro-phenyl)-2H-pyrrol-5-one (compound IV-12) (as described in *Bioorganic & Medicinal Chemistry* (2011),

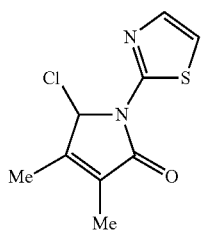

2-chloro-3,4-dimethyl-1-(1,3-thiazol-2-yl)-2H-pyrrol-2-one (compound III-17) from known 3,4-dimethyl-1-thiazol-2-yl-pyrrole-2,5-dione (CH 633 678 A5 (Swiss patent application no. 9001/77)) ¹H NMR (400 MHz, CDCl₃): δ ppm 1.96 (bs, 3H), 2.18 (bs, 3H), 6.79 (bs, 1H), 7.11 (bs, 1H), 7.60 (bs, 1H).

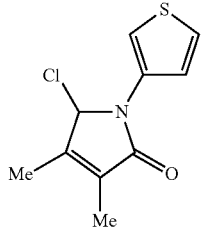

2-chloro-3,4-dimethyl-1-(3-thienyl)-2H-pyrrol-5-one (compound III-18) from 3,4-dimethyl-1-(3-thienyl)pyrrole-2,5-dione (compound IV-16); ¹H NMR (400 MHz, CDCl₃): δ ppm 1.94 (s, 3H), 2.05 (s, 3H), 5.97 (s, 1H), 7.26 (dd, 1H), 7.39-7.44 (m, 1H), 7.47 (m, 1H).

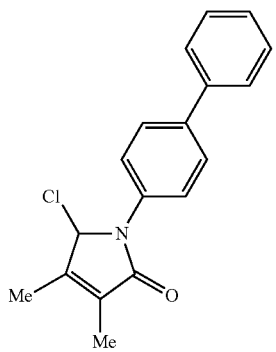

2-chloro-3,4-dimethyl-1-(4-phenylphenyl)-2H-pyrrol-5-one (compound III-19) from known 2-hydroxy-3,4-dimethyl-1-(4-phenylphenyl)-2H-pyrrol-5-one (CH 633 678 A5) ¹H NMR (400 MHz, CDCl₃): δ ppm 1.94 (s, 3H), 2.14 (s, 3H), 6.21 (bs, 1H), 7.34 (t, 1H), 7.44 (t, 2H), 7.56-7.72 (m, 6H).

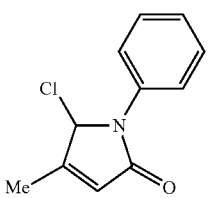

2-chloro-3-methyl-1-phenyl-2H-pyrrol-5-one (compound III-20) from known 2-hydroxy-3-methyl-1-phenyl-2H-pyrrol-5-one (Bioorganic & Medicinal Chemistry (2011), 19(9), 2823-2834); ¹H NMR (400 MHz, CDCl₃): δ ppm 2.15 (s, 3H), 6.05 (bs, 1H), 6.23 (bs, 1H), 7.23 (t, 1H), 7.42 (t, 2H), 7.56 (d, 2H).

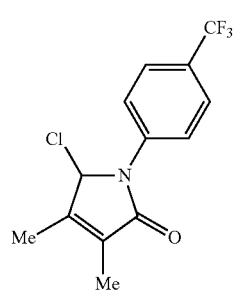

2-chloro-3,4-dimethyl-1[4-(trifluoromethyl)phenyl]-2H-pyrrol-5-one (compound (III-21) from known 3,4-dimethyl-[4-(trifluoromethyl)phenyl]-pyrrole-2,5-dione (CH 633678 A5 19821231); ¹H NMR (400 MHz, CDCl₃): δ ppm 7.83 (d, 2H), 7.67 (d, 2H), 6.20 (s, 1H), 2.15 (s, 3H), 1.94 (s, 3H).

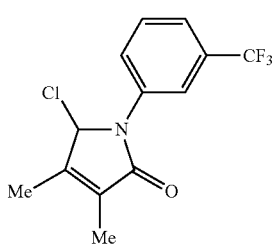

2-chloro-3,4-dimethyl-1[3-(trifluoromethyl)phenyl]-2H-pyrrol-5-one (compound (111-22) from known 3,4-dimethyl-[3-(trifluoromethyl)phenyl]-pyrrole-2,5-dione (CH 633 678); ¹H NMR (400 MHz, CDCl₃): δ ppm 7.96 (s, 1H), 7.86 (d, 1H), 7.51-7.60 (m, 1H), 7.43-7.49 (m, 1H), 6.19 (s, 1H), 2.15 (s, 3H), 1.95 (s, 3H).

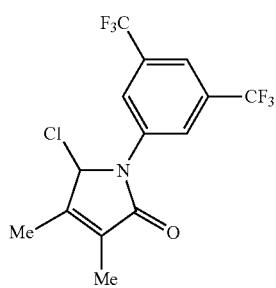

2-chloro-3,4-dimethyl-1-[3,5-bis(trifluoromethyl)phenyl]-2H-pyrrol-5-one (compound (III-23) from known 3,4-dimethyl-[3,5-bis(trifluoromethyl)phenyl]-pyrrole-2,5-dione (CH 633 678 A5) ¹H NMR (400 MHz, CDCl₃): δ ppm 8.22 (s, 2H), 7.69 (s, 1H), 6.21 (s, 1H), 2.17 (s, 3H), 1.95 (s, 3H).

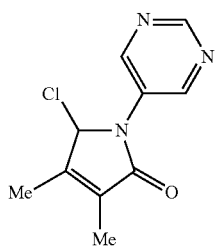

2-chloro-3,4-dimethyl-1-pyrimidin-5-yl-2H-pyrrol-5-one (compound (III-24) from known 3,4-dimethyl[3,5-bis(trifluoromethyl)phenyl]-pyrrole-2,5-dione (IV-16)) (CH 633 678 A5). ¹H NMR (400 MHz, CDCl₃): δ ppm 9.35 (s, 2H) 8.86 (m, 1H), 5.79-5.93 (s, 1H), 2.09 (s, 3H). 1.85 (m, 3H).

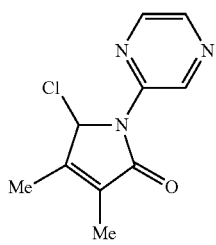

2-chloro-3,4-dimethyl-1-pyrazin-2-yl-2H-pyrrol-5-one (compound (III-25) from known 3,4-dimethyl[3,5-bis(trifluoromethyl)phenyl]-pyrrole-2,5-dione (CH 633 678 A5). ¹H NMR (400 MHz, CDCl₃): δ ppm 8.22 (s, 2H), 7.69 (s, 1H), 6.21 (s, 1H), 2.17 (s, 3H), 1.95 (s, 3H).

Step 2 tert-butyl (3E,3aR,8bS)-3-[[1-(methoxymethyl)-4-methyl-5-oxo-2H-pyrrol-2-yl]oxymethylene]-2-oxo-4,8b-dihydro-3aH-indeno[1,2-b]pyrrole-1-carboxylate (compound Ia-1)

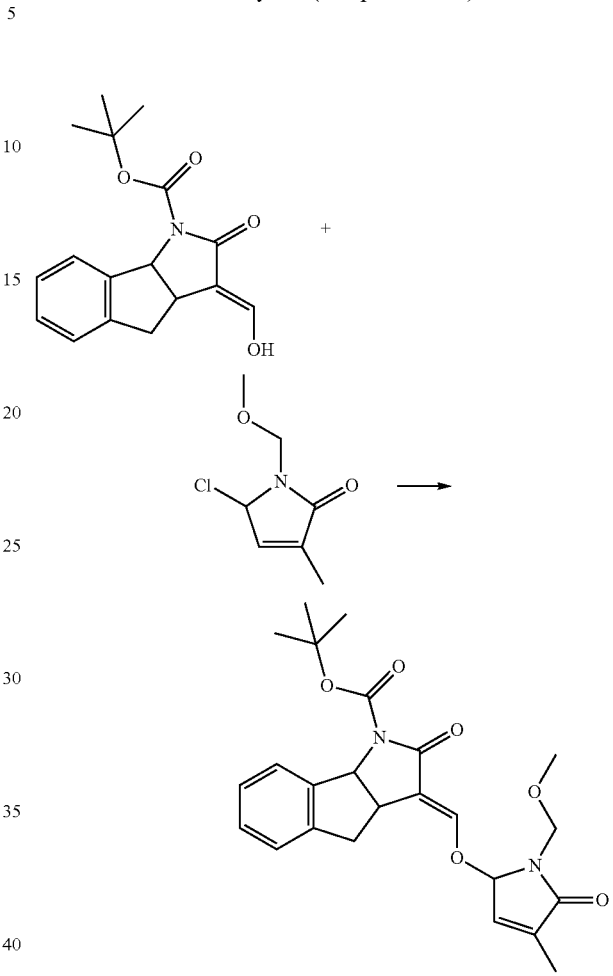

A solution of tert-butyl 3-(hydroxymethylene)-2-oxo-4,8b-dihydro-3aH-indeno[1,2-b]pyrrole-1-carboxylate (0.22 g, 0.73 mmol in 1,2-dimethoxyethane (7 mL)) under argon was cooled to 0° C. and potassium tert-butylate (0.101 g, 0.87 mmol) was added. After stirring for 5 minutes a 0° C., 2-chloro-1-(methoxymethyl)-4-methyl-2H-pyrrol-5-one (compound III-1) (0.279 g, 0.87 mmol, 55%) was added and the reaction mixture was stirred at room temperature for 1 h. Water and ethyl acetate were added and the aqueous layer was extracted with ethyl acetate. The combined organic layers were washed with brine, dried over Na₂SO₄ and the solvent was evaporated. The residue was purified by flash chromatography over silica to give tert-butyl (3E)-3-[[1-(methoxymethyl)-4-methyl-5-oxo-2H-pyrrol-2-yl]oxymethylene]-2-oxo-4,8b-dihydro-3aH-indeno[1,2-b]pyrrole-1-carboxylate Ia-1 as a gum and a 1/1 mixture of diastereoisomers (0.259 g, 72%); LCMS: RT 1.07 min; ES+ 441 (M+H+); ¹H NMR (400 MHz, CDCl₃): δ ppm 1.60 (s, 9H), 1.98 (s, 3H), 3.16-3.38 (m, 5H), 3.74 (m 1H), 4.56 (d, 1H) 4.96 (d, 1H), 5.70 (d, 1H), 5.83 (s, 1H), 6.63 (s, 1H), 7.17-7.29 (m, 4H), 7.65 (d, 1H).

A similar procedure was used to prepare the following compounds:

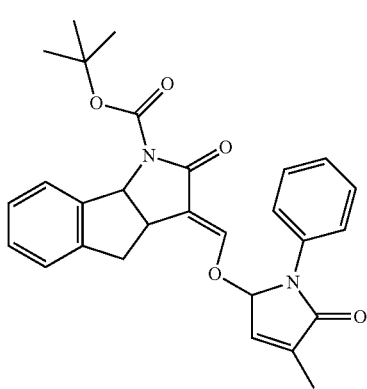

(Ia-2)

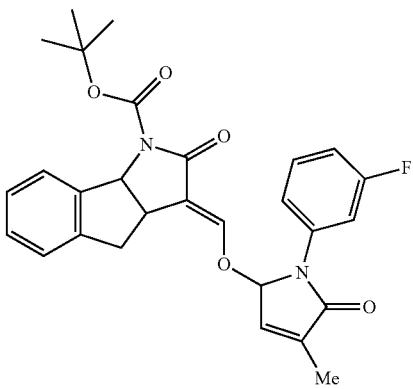

(Ia-9)

tert-butyl (3E)-3-[(4-methyl-5-oxo-1-phenyl-2H-pyrrol-2-yl)oxymethylene]-2-oxo-4,8b-dihydro-3aH-indeno[1,2-b]pyrrole-1-carboxylate (compound Ia-2) from 2-chloro-4-methyl-1-phenyl-2H-pyrrol-5-one (compound III-2); LCMS: RT 1.14 min; ES+472 (M+H+); $^1$H NMR (400 MHz, CDCl$_3$): δ ppm 1.59 (s, 9H), 2.05 (s, 3H), 2.72 (dd, 0.5H), 3.04 (dd, 0.5H), 3.15 (dd, 0.5H), 3.20-3.31 (m, 1H), 3.58-3.70 (m, 1H), 5.61-5.69 (m, 1H), 6.19 (s, J=1.47 Hz, 0.5H), 6.21-6.28 (s, 0.5H), 6.68 (m, 1H), 6.98 (d, 0.5H), 7.12 (d, 0.5H), 7.17-7.29 (m, 4H) 7.34-7.46 (m, 2H) 7.48-7.58 (m, 2H) 7.62 (t, J=7.70 Hz, 1H).

tert-butyl (3E)-3-[(4-methyl-5-oxo-1-(3-fluoro-phenyl)-2H-pyrrol-2-yl)oxymethylene]-2-oxo-4,8b-dihydro-3aH-indeno[1,2-b]pyrrole-1-carboxylate (compound Ia-9) from 2-chloro-4-methyl-1-(3-fluoro-phenyl)-2H-pyrrol-5-one (compound III-11); LCMS (Method A): RT 1.15 min; ES– 490 (M–H+).

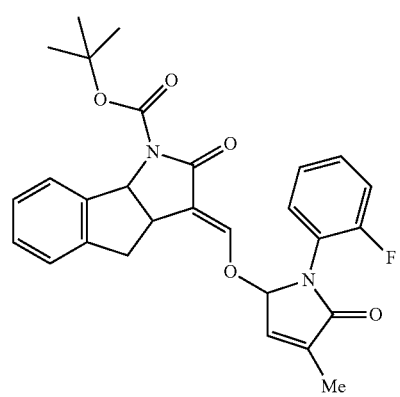

(Ia-10)

tert-butyl (3E)-3-[(4-methyl-5-oxo-1-(2-fluoro-phenyl)-2H-pyrrol-2-yl)oxymethylene]-2-oxo-4,8b-dihydro-3aH-indeno[1,2-b]pyrrole-1-carboxylate (compound Ia-10) from 2-chloro-4-methyl-1-(2-fluoro-phenyl)-2H-pyrrol-5-one (compound III-12); LCMS (Method A): RT 1.12 min; ES+ 491 (M+H+).

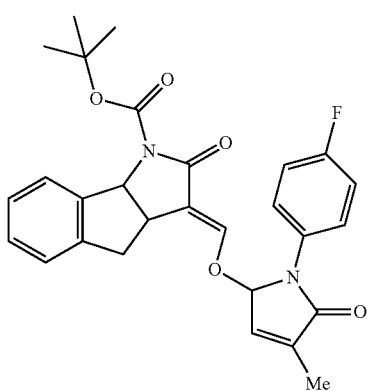

(Ia-8)

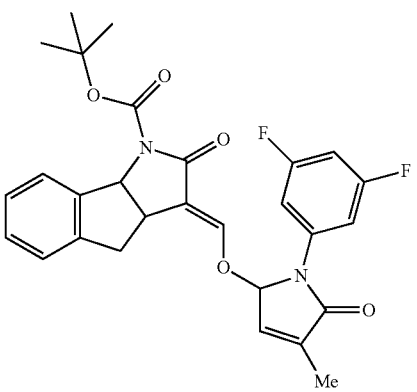

(Ia-11)

tert-butyl (3E)-3-[(4-methyl-5-oxo-1-(4-fluoro-phenyl)-2H-pyrrol-2-yl)oxymethylene]-2-oxo-4,8b-dihydro-3aH-indeno[1,2-b]pyrrole-1-carboxylate (compound Ia-8) from 2-chloro-4-methyl-1-(4-fluoro-phenyl)-2H-pyrrol-5-one (compound III-10); LCMS (Method B): RT 1.94 min; ES+ 491 (M+H+).

tert-butyl (3E)-3-[(4-methyl-5-oxo-1-(3,5-difluoro-phenyl)-2H-pyrrol-2-yl)oxymethylene]-2-oxo-4,8b-dihydro-3aH-indeno[1,2-b]pyrrole-1-carboxylate (compound Ia-11) from 2-chloro-4-methyl-1-(3,5-difluoro-phenyl)-2H-pyrrol-5-one (compound III-13); LCMS (Method B): RT 2.00 min, ES+ 509 (M+H+); RT 2.03 min, ES+ 509 (M+H+).

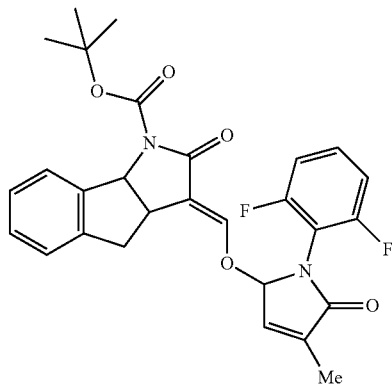

(Ia-12)

tert-butyl (3E)-3-[(4-methyl-5-oxo-1-(2,6-difluoro-phenyl)-2H-pyrrol-2-yl)oxymethylene]-2-oxo-4,8b-dihydro-3aH-indeno[1,2-b]pyrrole-1-carboxylate (compound Ia-12) from 2-chloro-4-methyl-1-(2,6-difluoro-phenyl)-2H-pyrrol-5-one (compound III-14); LCMS (Method A): RT 1.12 min; ES+ 509 (M+H+).

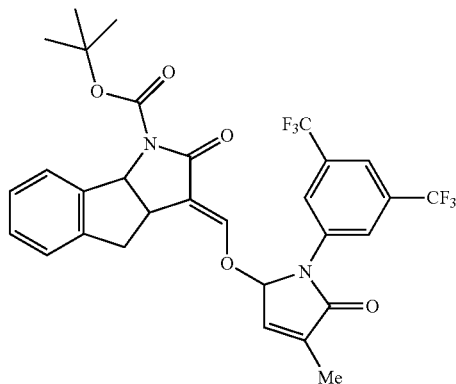

(Ia-13)

tert-butyl (3E)-3-[(4-methyl-5-oxo-1-(3,5-bistrifluoromethyl-phenyl)-2H-pyrrol-2-yl)oxymethylene]-2-oxo-4,8b-dihydro-3aH-indeno[1,2-b]pyrrole-1-carboxylate (compound Ia-13) from 2-chloro-4-methyl-1-(3,5-bistrifluoromethyl-phenyl)-2H-pyrrol-5-one (compound III-15); LCMS (Method A): RT 1.29 min, ES− 607 (M−H+).

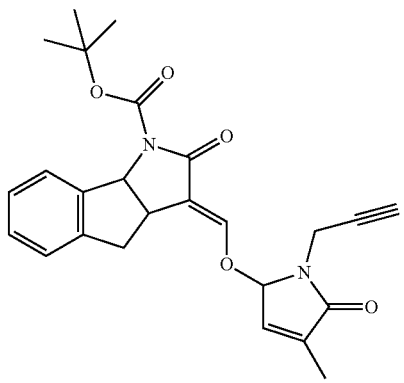

(Ia-6)

tert-butyl (3E)-3-[(4-methyl-5-oxo-1-prop-2-ynyl-2H-pyrrol-2-yl)oxymethylene]-2-oxo-4,8b-dihydro-3aH-indeno[1,2-b]pyrrole-1-carboxylate (compound Ia-6) from 2-chloro-4-methyl-1-phenyl-2H-pyrrol-5-one (compound III-6); LCMS: RT 1.08 min; ES+ 435 (M+H+); $^1$H NMR (400 MHz, CDCl$_3$): δ ppm 1.62 (s, 9H), 1.98 (s, 3H), 2.23-2.28 (m, 1H), 3.17-3.27 (m, 1H), 3.31-3.42 (m, 1H), 3.72-3.88 (m, 2H), 4.51-4.61 (m, 1H), 5.71 (d, 1H), 5.79-5.87 (m, 1H), 6.60 (s, 1H), 7.19-7.33 (m, 4H), 7.63-7.69 (m, 1H).

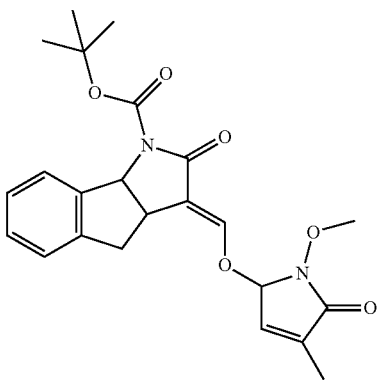

(Ia-3)

tert-butyl (3E)-3-[(4-methyl-5-oxo-1-methoxy-2H-pyrrol-2-yl)oxymethylene]-2-oxo-4,8b-dihydro-3aH-indeno[1,2-b]pyrrole-1-carboxylate (compound Ia-3) from 2-chloro-4-methyl-1-phenyl-2H-pyrrol-5-one (compound III-3); LCMS: RT 1.06 min; ES+ 490 (M+MeCN+Na+); $^1$H NMR (400 MHz, CDCl$_3$): δ ppm 1.59 (s, 9H), 1.96 (s, 3H) 3.25 (dd, 1H) 3.38 (dd, 1H) 3.76-3.90 (m, 1H), 3.83 (s, 1.5H), 3.85 (s, 1.5H), 5.68-5.70 (m, 1H), 5.73 (d, 1H), 6.49-6.52 (m, 1H), 7.18-7.30 (m, 3H), 7.41 (s, 1H), 7.67 (d, 1H).

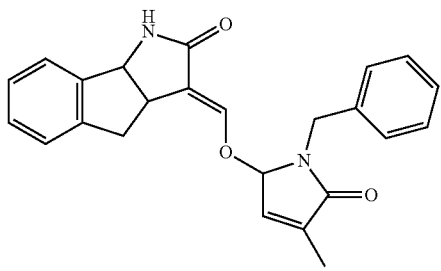

(Ia-4)

tert-butyl (3E)-3-[(4-methyl-5-oxo-1-benzyl-2H-pyrrol-2-yl)oxymethylene]-2-oxo-4,8b-dihydro-3aH-indeno[1,2-b]pyrrole-1-carboxylate (compound Ia-4) from 2-chloro-4-methyl-1-phenyl-2H-pyrrol-5-one (compound III-4); LCMS: RT 0.93 min; ES+ 387 (M+H$^+$).

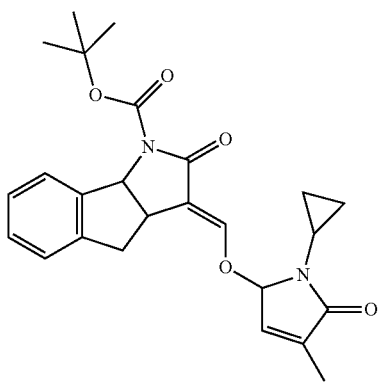

(Ia-5)

tert-butyl (3E)-3-[(4-methyl-5-oxo-1-cyclopropyl-2H-pyrrol-2-yl)oxymethylene]-2-oxo-4,8b-dihydro-3aH-indeno[1,2-b]pyrrole-1-carboxylate (compound Ia-5) from 2-chloro-4-methyl-1-phenyl-2H-pyrrol-5-one (compound III-5); LCMS: RT 1.09 min; ES+ 437 (M+H$^+$); $^1$H NMR (400 MHz, CDCl$_3$): δ ppm 0.66-0.91 (m, 4H), 1.61 (s, 9H), 1.93 (s, 3H), 2.45-2.55 (m, 1H), 3.14-3.24 (m, 1H), 3.29-3.43 (m, 1H), 3.70-3.80 (m, 1H), 5.55 (s, 1H), 5.71 (d, 1H) 6.42-6.53 (m, 1H), 7.14-7.36 (m, 4H), 7.66 (d, 1H).

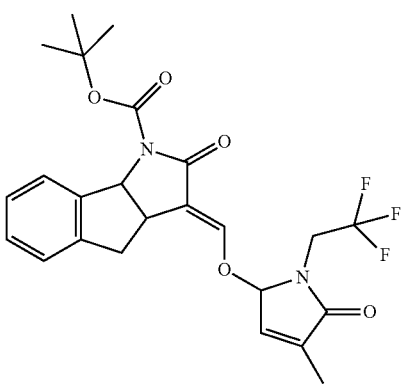

(Ia-7)

tert-butyl (3E)-3-[(4-methyl-5-oxo-1-(2,2,2-trifluoro-ethyl)-2H-pyrrol-2-yl)oxymethylene]-2-oxo-4,8b-dihydro-3aH-indeno[1,2-b]pyrrole-1-carboxylate (compound Ia-7) from 2-chloro-4-methyl-1-phenyl-2H-pyrrol-5-one (compound III-7); LCMS: RT 1.14 min; ES+ 479 (M+H$^+$); $^1$H NMR (400 MHz, CDCl$_3$): δ ppm 7.66 (d, 1H), 7.17-7.29 (m, 4H), 6.65 (s, 1H), 5.80 (m, 1H), 5.71 (d, 1H), 4.25-4.37 (m, 1H), 3.75 (m, 1H), 3.53-3.67 (m, 1H), 3.36 (m, 1H), 3.12-3.20 (m, 1H), 2.00 (s, 3H), 1.59 (m, 9H).

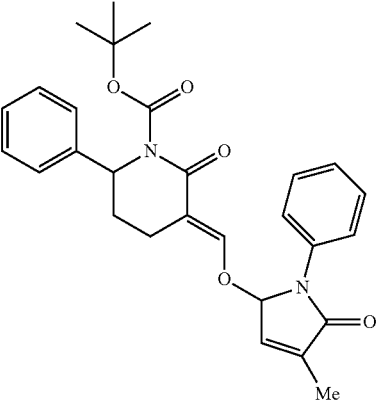

(Ia-14)

tert-butyl (3E)-3-[(4-methyl-5-oxo-1-phenyl-2H-pyrrol-2-yl)oxymethylene]-2-oxo-6-phenyl-piperidine-1-carboxylate (compound Ia-14) from 2-chloro-4-methyl-1-phenyl-2H-pyrrol-5-one (compound III-2) and tert-butyl (3E)-3-(hydroxymethylene)-2-oxo-6-phenyl-piperidine-1-carboxylate (WO2013/171092); LCMS (Method A): RT 1.13 min; ES+ 475 (M+H$^+$).

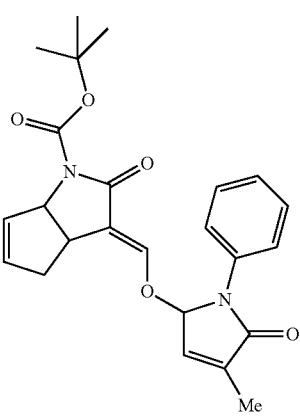

(Ia-15)

tert-butyl (3E)-3-[(4-dimethyl-5-oxo-1-phenyl-2H-pyrrol-2-yl)oxymethylene]-2-oxo-4,6a-dihydro-3aH-cyclopenta[b]pyrrole-1-carboxylate (compound Ia-15) from 2-chloro-4-methyl-1-phenyl-2H-pyrrol-5-one (compound III-2) and tert-butyl (3E,3aR,6aR)-3-(hydroxymethylene)-2-oxo-4,6a-dihydro-3aH-cyclopenta[b]pyrrole-1-carboxylate (WO2013/171092); LCMS (Method A): RT 1.06 min; ES+ 423 (M+H$^+$).

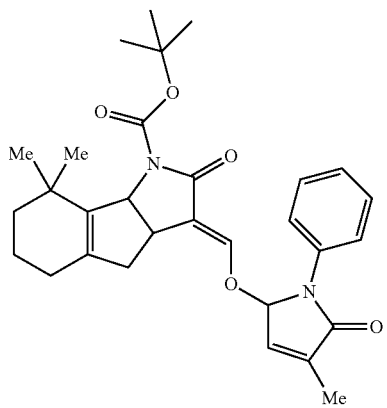

(Ia-16)

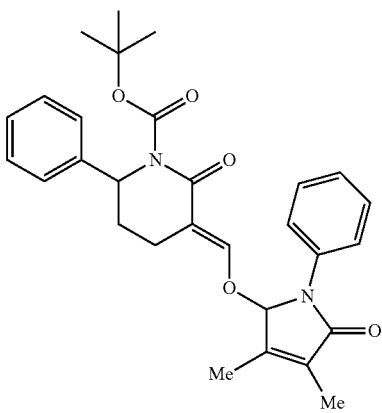

(Ia-18)

tert-butyl (3E)-8,8-dimethyl-3-[(4-methyl-5-oxo-1-phenyl-2H-pyrrol-2 yl)oxymethylene]-2-oxo-3a,4,5,6,7,8b-hexahydroindeno[1,2-b]pyrrole-1-carboxylate (compound Ia-16) from 2-chloro-4-methyl-1-phenyl-2H-pyrrol-5-one (compound III-2) and tert-butyl (3E,3aR,8bS)-3-(hydroxymethylene)-8,8-dimethyl-2-oxo-3a,4,5,6,7,8b-hexahydroindeno[1,2-b]pyrrole-1-carboxylate (WO2013/092430); LCMS (Method A): RT 1.29 min; ES+ 405 (M−Boc+H+).

tert-butyl (3E)-3-[(3,4-dimethyl-5-oxo-1-phenyl-2H-pyrrol-2-yl)oxymethylene]-2-oxo-6-phenyl-piperidine-1-carboxylate (compound Ia-18) from 2-chloro-3,4-dimethyl-1-phenyl-2H-pyrrol-5-one (compound III-8) and tert-butyl (3E)-3-(hydroxymethylene)-2-oxo-6-phenyl-piperidine-1-carboxylate (from WO 2013/171092); LCMS (Method A): RT 1.15 min; ES+ 489 (M+H+);

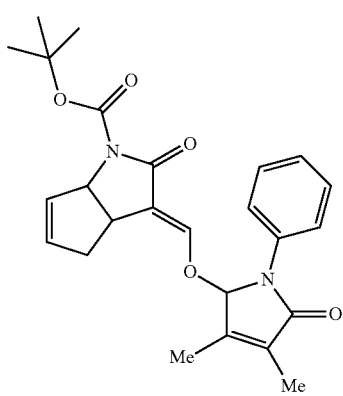

(Ia-17)

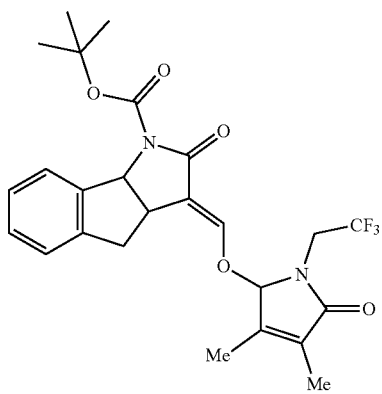

(Ia-19)

tert-butyl (3E)-3-[(3,4-dimethyl-5-oxo-1-phenyl-2H-pyrrol-2-yl)oxymethylene]-2-oxo-4,6a-dihydro-3aH-cyclopenta[b]pyrrole-1-carboxylate (compound Ia-17) from 2-chloro-3,4-dimethyl-1-phenyl-2H-pyrrol-5-one (compound III-8) and tert-butyl (3E)-3-(hydroxymethylene)-2-oxo-4,6a-dihydro-3aH-cyclopenta[b]pyrrole-1-carboxylate (from WO 2013/171092); LCMS (Method A): RT 1.09 min; ES+ 895 (2M+Na+);

tert-butyl (3E)-3-[(3,4-dimethyl-5-oxo-1-(2,2,2-trifluoroethyl)-2H-pyrrol-2-yl)oxymethylene]-2-oxo-4,8b-dihydro-3aH-indeno[1,2-b]pyrrole-1-carboxylate (compound Ia-19) from 2-chloro-4-methyl-1-phenyl-2H-pyrrol-5-one (compound III-9); LCMS (Method A): RT 1.14 min; ES+ 493 (M+H+).

(Ia-20)

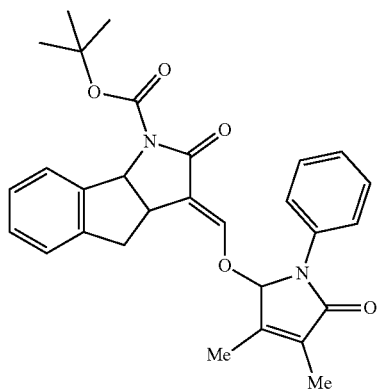

tert-butyl (3E)-3-[(3,4-dimethyl-5-oxo-1-phenyl-2H-pyrrol-2-yl)oxymethylene]-2-oxo-4,8b-dihydro-3aH-indeno[1,2-b]pyrrole-1-carboxylate (compound Ia-20) from 2-chloro-3,4-dimethyl-1-(3,5-bistrifluoromethyl-phenyl)-2H-pyrrol-5-one (compound III-16); LCMS (Method B): RT 1.96 min, ES+ 497 (M+H$^+$).

(Ia-24)

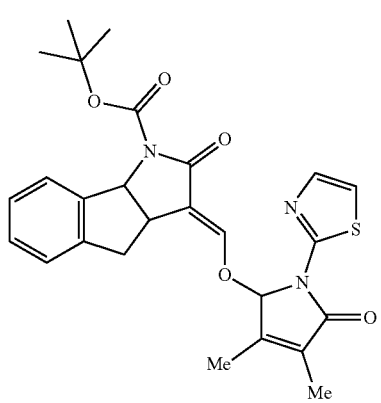

tert-butyl (3E)-3-[(3,4-dimethyl-5-oxo-1-thiazol-2-yl-2H-pyrrol-2-yl)oxymethylene]-2-oxo-4,8b-dihydro-3aH-indeno[1,2-b]pyrrole-1-carboxylate (compound Ia-24) from 5-chloro-3,4-dimethyl-1-(1,3-thiazol-2-yl)-1,5-dihydro-2H-pyrrol-2-one (compound III-17); LCMS (Method B): RT 1.90 min, ES+ 495 (M+H$^+$).

(Ia-25)

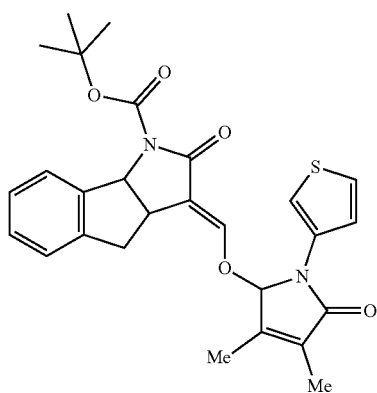

tert-butyl (3E)-3-[[3,4-dimethyl-5-oxo-1-(3-thienyl)-2H-pyrrol-2-yl]oxymethylene]-2-oxo-4,8b-dihydro-3aH-indeno[1,2-b]pyrrole-1-carboxylate (compound Ia-25) from 2-chloro-3,4-dimethyl-1-(3-thienyl)-2H-pyrrol-5-one (compound III-18); LCMS (Method A): RT 1.18 min; ES+ 493 (M+H)$^+$.

(Ia-26)

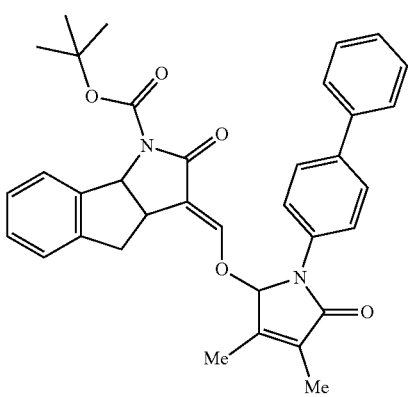

tert-butyl (3E)-3-[[3,4-dimethyl-5-oxo-1-(4-phenylphenyl)-2H-pyrrol-2-yl]oxymethylene]-2-oxo-4,8b-dihydro-3aH-indeno[1,2-b]pyrrole-1-carboxylate (compound Ia-26) from 2-chloro-3,4-dimethyl-1-(4-phenylphenyl)-2H-pyrrol-5-one (compound III-19); LCMS (Method A): RT 1.28 min, ES+ 563 (M+H$^+$).

(Ia-27)

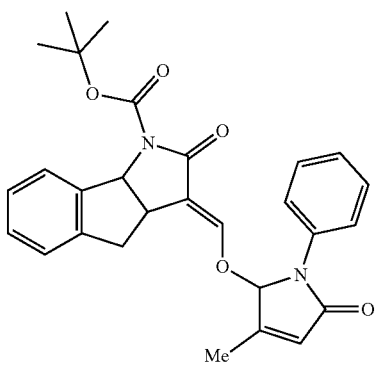

tert-butyl (3E)-3-[(3-methyl-5-oxo-1-phenyl-2H-pyrrol-2-yl)oxymethylene]-2-oxo-4,8b-dihydro-3aH-indeno[1,2-b]pyrrole-1-carboxylate (compound Ia-27) from 2-chloro-3-methyl-1-phenyl-2H-pyrrol-5-one (compound III-20); LCMS (Method A): RT 1.12 min, ES+ 471 (M−H$^+$).

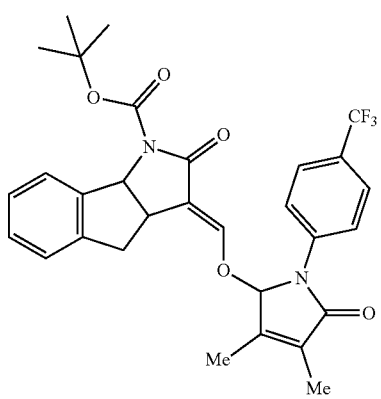

(Ia-28)

tert-butyl (3E)-3-[[3,4-dimethyl-5-oxo-1-[4-(trifluoromethyl)phenyl]-2H-pyrrol-2-yl]oxymethylene]-2-oxo-4,8b-dihydro-3aH-indeno[1,2-b]pyrrole-1-carboxylate (compound Ia-28) from 2-chloro-3,4-dimethyl-1-[4-(trifluoromethyl)phenyl]-2H-pyrrol-5-one (compound III-21); LCMS (Method A): RT 1.26 min, ES+ 554 (M+H$^+$).

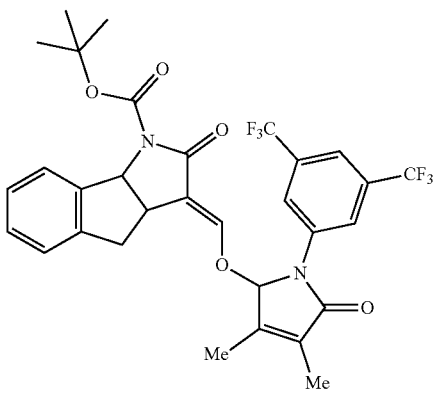

(Ia-30)

tert-butyl (3E)-3-[[3,4-dimethyl-5-oxo-1-[3,5-bis(trifluoromethyl)phenyl]-2H-pyrrol-2-yl]oxymethylene]-2-oxo-4,8b-dihydro-3aH-indeno[1,2-b]pyrrole-1-carboxylate (compound Ia-30) from 2-chloro-3,4-dimethyl-1-[3,5-bis(trifluoromethyl)phenyl]-2H-pyrrol-5-one (compound III-23); LCMS (Method A): RT 1.32 min, ES+ 622 (M+H$^+$).

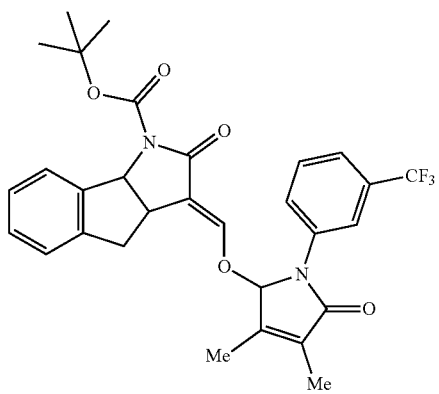

(Ia-29)

tert-butyl (3E)-3-[[3,4-dimethyl-5-oxo-1-[3-(trifluoromethyl)phenyl]-2H-pyrrol-2-yl]oxymethylene]-2-oxo-4,8b-dihydro-3aH-indeno[1,2-b]pyrrole-1-carboxylate (compound Ia-29) from 2-chloro-3,4-dimethyl-1-[3-(trifluoromethyl)phenyl]-2H-pyrrol-5-one (compound III-22); LCMS (Method A): RT 1.31 min, ES+ 554 (M+H$^+$).

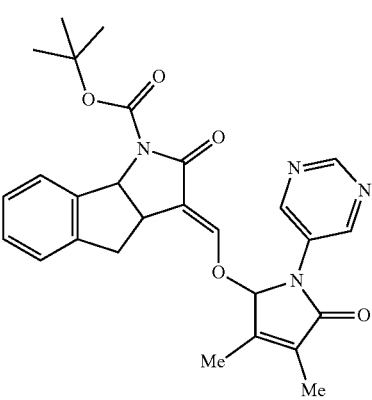

(Ia-31)

tert-butyl (3E)-3-[(3,4-dimethyl-5-oxo-1-pyrimidin-5-yl-2H-pyrrol-2-yl)oxymethylene]-2-oxo-4,8b-dihydro-3aH-indeno[1,2-b]pyrrole-1-carboxylate (compound Ia-31) from 2-chloro-3,4-dimethyl-1-1-pyrimidin-5-yl-2H-pyrrol-5-one (compound III-24); LCMS (Method A): RT 1.09 min, ES+ 489 (M+H$^+$).

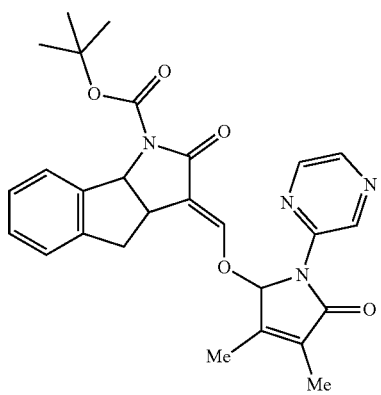

(Ia-32)

tert-butyl (3E)-3-[(3,4-dimethyl-5-oxo-1-pyrazin-2-yl-2H-pyrrol-2-yl)oxymethylene]-2-oxo-4,8b-dihydro-3aH-indeno[1,2-b]pyrrole-1-carboxylate (compound Ia-32) from 2-chloro-3,4-dimethyl-1-pyrazin-2-yl-2H-pyrrol-5-one (compound III-25); LCMS (Method A): RT 1.16 min, ES+ 489 (M+H+).

Step 3: (3E)-3-[[1-(methoxymethyl)-4-methyl-5-oxo-2H-pyrrol-2-yl]oxymethylene]-1,3a,4,8b-tetrahydroindeno[2-b]pyrrol-2-one (compound Ib-1)

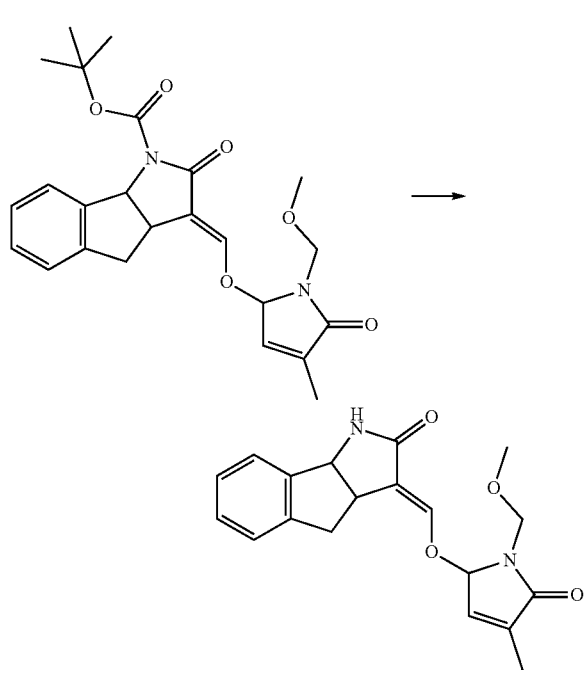

To a solution of tert-butyl (3E)-3-[[1-(methoxymethyl)-4-methyl-5-oxo-2H-pyrrol-2-yl]oxymethylene]-2-oxo-4,8b-dihydro-3aH-indeno[1,2-b]pyrrole-1-carboxylate (compound Ia-1, 0.254 g, 0.51 mmol) in dichloromethane (5 mL) was added HCl in dioxane (4 M, 0.65 mL). After 10 minutes, saturated NaHCO₃ solution was added and the aqueous layer was extracted with dichloromethane. The combined organic layers were dried over Na₂SO₄ and the solvent was evaporated The residue was purified by flash chromatography over silica to give (3E)-3-[[1-(methoxymethyl)-4-methyl-5-oxo-2H-pyrrol-2-yl]oxymethylene]-1,3a,4,8b-tetrahydroindeno[1,2-b]pyrrol-2-one Ib-1 (52 mg, 26%) as a gum; LCMS: RT 0.81 min; ES+ 353 (M+Na+); ¹H NMR (400 MHz, CDCl₃): δ ppm 1.60 (s, 9H), 1.98 (s, 3H), 3.16-3.38 (m, 5H), 3.74 (m 1H), 4.56 (d, 1H) 4.96 (d, 1H), 5.70 (d, 1H), 5.83 (s, 1H), 6.63 (s, 1H), 7.17-7.29 (m, 4H), 7.65 (d, 1H).

A similar procedure was used to prepare the following compounds:

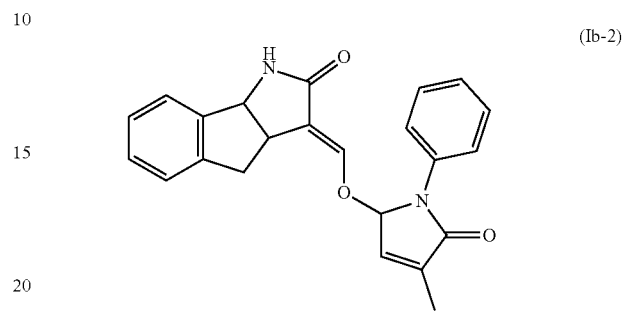

(Ib-2)

(3E)-3-[(4-methyl-5-oxo-1-phenyl-2H-pyrrol-2-yl)oxymethylene]-1,3a,4,8b-tetrahydroindeno[1,2-b]pyrrol-2-one (Ib-2); LCMS: RT 0.92 min; ES+ 373 (M+H+); ¹H NMR (400 MHz, CDCl₃): δ ppm 1.92 (s, 3H), 2.45 (m, 1H), 3.06-3.21 (m, 1H), 3.57-3.73 (m, 1H), 4.86-4.95 (m, 1H), 6.69 (s, 0.5H), 6.75 (s, 0.5H), 6.91 (s, 1H), 6.97-7.32 (m, 6H), 7.39-7.49 (m, 2H), 7.60 (d, 2H), 8.35-8.47 (s, 1H).

(Ib-8)

(3E)-3-[(4-methyl-5-oxo-1-(4-fluoro-phenyl)-2H-pyrrol-2-yl)oxymethylene]-1,3a,4,8b-tetrahydroindeno[1,2-b]pyrrol-2-one (compound Ib-8); LCMS (Method A): RT 0.93 min; ES+ 391 (M+H+). ¹H NMR (400 MHz, CDCl₃): δ ppm 2.04 and 2.05 (m, 3H), 2.56 and 2.95 (dd, 1H), 3.24 and 3.38 (dd, 1H), 3.72-3.79 and 3.80-3.86 (m, 1H), 5.04 (t, 1H), 6.10 and 6.16 (m, 1H), 6.28 (s, 1H), 6.69 (q, 1H), 7.03-7.13 (m, 3H), 7.15-7.29 (m, 3H), 7.47-7.56 (m, 2H).

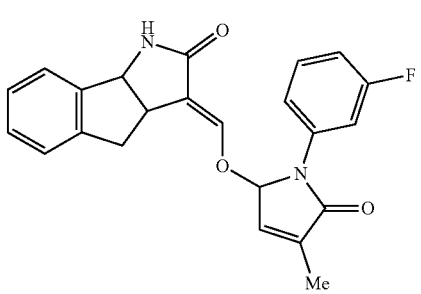

(Ib-9)

(3E)-3-[(4-methyl-5-oxo-1-(3-fluoro-phenyl)-2H-pyrrol-2-yl)oxymethylene]-1,3a,4,8b-tetrahydroindeno[1,2-b]pyrrol-2-one (compound Ib-9); LCMS (Method A): RT 0.93 min, ES+ 782 [2(M+H$^+$)]; 0.94 min, ES+ 782 [2(M+H$^+$)]. $^1$H NMR (400 MHz, CDCl$_3$): δ ppm 2.03 and 2.05 (s, 3H), 2.67 and 2.97 (dd, 1H), 3.25-3.45 (m, 1H), 3.77 and 3.84 (m, 1H), 5.04 (t, 1H), 6.15 and 6.21 (s, 1H), 6.70 (s, 1H), 6.79 (s, 1H), 6.91 (m, 1H), 7.03-7.29 (m, 4H), 7.30-7.57 (m, 3H).

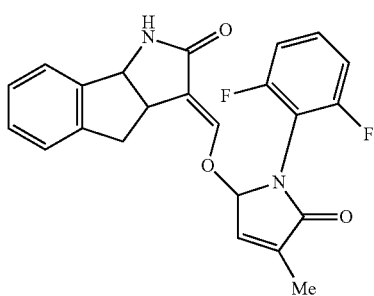
(Ib-12)

(3E)-3-[(4-methyl-5-oxo-1-(2,6-difluoro-phenyl)-2H-pyrrol-2-yl)oxymethylene]-1,3a,4,8b-tetrahydroindeno[1,2-b]pyrrol-2-one (compound Ib-12); LCMS (Method A): RT 0.91 min, ES+ 818 [2(M+H$^+$)]. $^1$H NMR (400 MHz, CDCl$_3$): δ ppm 1.98 and 2.00 (s, 3H), 2.61 and 2.80 (dd, 1H), 3.18 and 3.27 (dd, 1H), 3.63 and 3.76 (m, 1H), 4.94 and 4.96 (s, 1H), 5.93 and 5.96 (s, 1H), 6.49 (s, 1H), 6.71 (s, 1H), 6.88-7.32 (m, 7H).

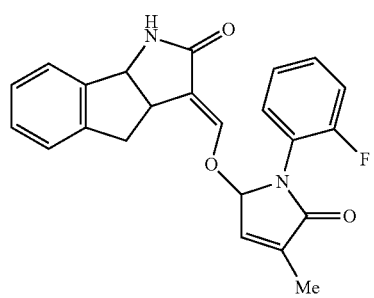
(Ib-10)

(3E)-3-[(4-methyl-5-oxo-1-(2-fluoro-phenyl)-2H-pyrrol-2-yl)oxymethylene]-1,3a,4,8b-tetrahydroindeno[1,2-b]pyrrol-2-one (compound Ib-10); LCMS (Method B): RT 1.35 min, ES+ 782 [2(M+H$^+$)]. $^1$H NMR (400 MHz, CDCl$_3$): δ ppm 2.09 and 2.11 (s, 3H), 2.55 and 2.88 (dd, 1H), 3.21 and 3.34 (dd, 1H), 3.72 and 3.80 (m, 1H), 5.02-5.09 (m, 1H), 6.14 and 6.21 (s, 1H), 6.78 (s, 1H), 7.00-7.50 (m, 9H).

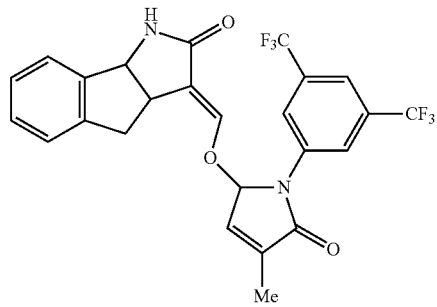
(Ib-13)

(3E)-3-[(4-methyl-5-oxo-1-(3,5-bistrifluoromethyl-phenyl)-2H-pyrrol-2-yl)oxymethylene]-1,3a,4,8b-tetrahydroindeno[1,2-b]pyrrol-2-one (compound Ib-13); LCMS (Method A): RT 1.09 min, ES+ 509 (M+H$^+$); RT 1.10, ES+ 509 (M+H$^+$). $^1$H NMR (400 MHz, CDCl$_3$): δ ppm δ 2.07 and 2.08 (s, 3H), 2.67 and 3.04 (dd, 1H), 3.37-3.51 (m, 1H), 3.71-3.79 and 3.86-3.95 (m, 1H), 5.04 and 5.09 (d, 1H), 6.09-6.18 (m, 1H), 6.26 and 6.33 (s, 1H), 6.76-6.81 (m, 1H), 7.01-7.10 (m, 1H), 7.15-7.33 (m, 3H), 7.70 (s, 1H), 8.30 and 8.31 (s, 2H).

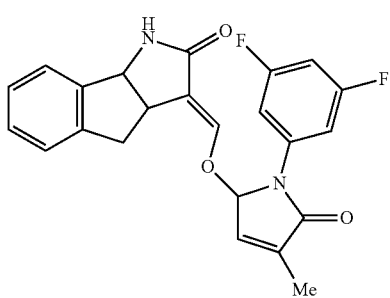
(Ib-11)

(3E)-3-[(4-methyl-5-oxo-1-(3,5-difluoro-phenyl)-2H-pyrrol-2-yl)oxymethylene]-1,3a,4,8b-tetrahydroindeno[1,2-b]pyrrol-2-one (compound Ib-11); LCMS (Method A): RT 0.96 min, ES+ 818 [2(M+H$^+$)]; RT 0.98 min, ES+ 818 [2(M+H$^+$)]. $^1$H NMR (400 MHz, CHLOROFORM-d) δ 2.06 and 2.08 (s, 3H), 2.80 and 3.06 (d, 1H), 3.35-3.58 (m, 1H), 3.77-3.98 (m, 1H), 5.09 (t, 1H), 6.16 and 6.20 (s, 1H), 6.60-6.91 (m, 3H), 7.01-7.46 (m, 6H).

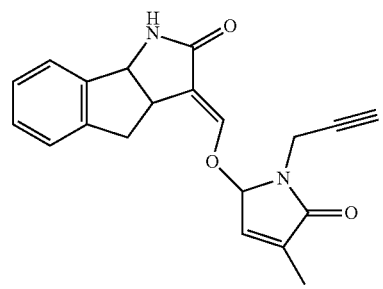
(Ib-6)

(3E)-3-[(4-methyl-5-oxo-1-prop-2-ynyl-2H-pyrrol-2-yl)oxymethylene]-1,3a,4,8b-tetrahydroindeno[1,2-b]pyrrol-2-one (Ib-6); LCMS: RT 0.84 min; ES+ 335 (M+H+); $^1$H NMR (400 MHz, CDCl₃): δ ppm 1.98 (s, 3H) 2.05 (s, 1H), 2.23-2.31 (m, 1H), 3.11 (dd, 1H), 3.49 (dd, 1H), 3.83 (m, 1H), 4.55-4.64 (m, 1H), 5.12 (d, J=8.07 Hz, 1H), 5.78-5.86 (m, 1H), 6.57-6.68 (m, 2H) 7.14 (dd, 1H), 7.21-7.32 (m, 4H)

¹H NMR (400 MHz, CDCl₃): δ ppm 7.21-7.31 (m, 4H), 7.06 (dd, 1H), 6.67 (t, 1H), 6.41 (br. s., 1H), 5.79 (br. s., 1H), 5.11 (d, 1H), 4.35 (m, 1H), 3.88-3.96 (m, 1H), 3.56-3.70 (m, 1H), 3.49 (m, 1H), 3.01-3.11 (m, 1H), 1.97 (s, 3H).

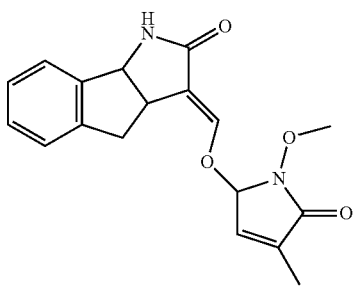

(Ib-3)

(3E)-3-[(4-methyl-5-oxo-1-methoxy-2H-pyrrol-2-yl)oxymethylene]-1,3a,4,8b-tetrahydroindeno[1,2-b]pyrrol-2-one (Ib-3); LCMS: RT 0.82 min; ES+ 327 (M+H+); ¹H NMR (400 MHz, CDCl₃): δ ppm 7.18-7.37 (m, 5H), 6.87 (br. s., 1H), 6.44-6.58 (m, 1H), 5.65-5.71 (m, 1H), 5.13 (d, J=7.7 Hz, 1H), 3.91-4.01 (m, 1H), 3.89 (d, J=2.6 Hz, 3H), 3.50 (dd, J=17.1, 9.7 Hz, 1H), 3.13 (d, J=16.9 Hz, 1H), 1.93-1.99 ppm (m, 3H)

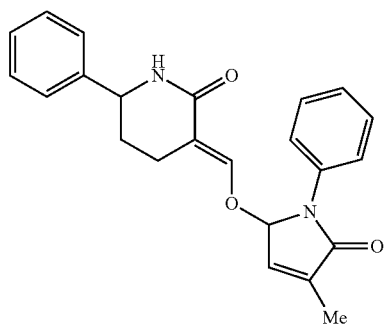

(Ib-14)

(3E)-3-[(4-methyl-5-oxo-1-phenyl-2H-pyrrol-2-yl)oxymethylene]-6-phenyl-piperidin-2-one (compound Ib-14); LCMS (Method A): RT 0.94 min; ES+ 375 (M+H⁺); ¹H NMR (400 MHz, CDCl₃): δ ppm 1.49-1.77 (m, 1H), 1.93-2.08 (m, 4H), 2.17-2.35 (m, 1H), 2.45-2.61 (m, 1H), 4.43-4.57 (m, 1H), 5.83 (br. s., 1H), 6.10-6.17 (m, 1H), 6.69 (t, 1H), 7.14-7.47 (m, 9H), 7.49-7.64 (m, 2H).

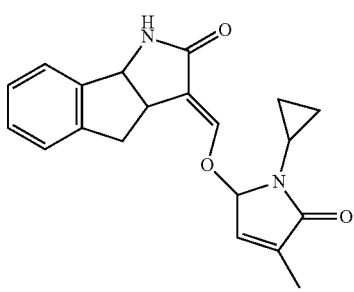

(Ib-5)

(3E)-3-[(4-methyl-5-oxo-1-cyclopropyl-2H-pyrrol-2-yl)oxymethylene]-1,3a,4,8b-tetrahydroindeno[1,2-b]pyrrol-2-one (Ib-5); LCMS: RT 0.83 min; ES+ 337 (M+H+); ¹H NMR (400 MHz, CDCl₃): δ ppm 0.68-0.97 (m, 4H), 1.93 (s, 3H), 2.52-2.65 (m, 1H), 3.10 (dt, 1H), 3.40-3.55 (m, 1H), 3.92 (m, 1H), 5.02-5.20 (d, 1H), 5.54 (s, 1H), 6.43-6.62 (m, 2H), 7.19-7.34 (m, 5H).

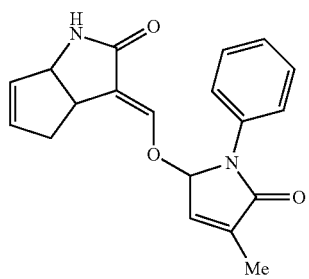

(Ib-15)

(3E)-3-[(4-dimethyl-5-oxo-1-phenyl-2H-pyrrol-2-yl)oxymethylene]-1,3a,4,6a-tetrahydrocyclopenta[b]pyrrol-2-one (compound Ib-15); LCMS (Method A): RT 0.82 min; ES+ 323 (M+H⁺); ¹H NMR (400 MHz, CDCl₃): δ ppm 1.96-2.06 (m, 3H), 2.00-2.32 (m, 1H), 2.60-2.84 (m, 1H), 3.46-3.66 (m, 1H), 4.57 (s, 1H), 5.53-5.83 (m, 2H), 5.90 (br. s., 1H), 6.15 (m, 1H), 6.66 (m, 1H), 7.07 (m, 1H), 7.17-7.25 (t, 1H), 7.35-7.45 (m, 2H), 7.54-7.64 (m, 2H).

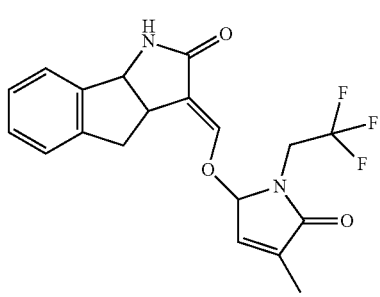

(Ib-7)

(3E)-3-[(4-methyl-5-oxo-1-(2,2,2-trifluoroethyl)-2H-pyrrol-2-yl)oxymethylene]-1,3a,4,8b-tetrahydroindeno[1,2-b]pyrrol-2-one (Ib-7); LCMS: RT 0.90 min; ES+379 (M+H+);

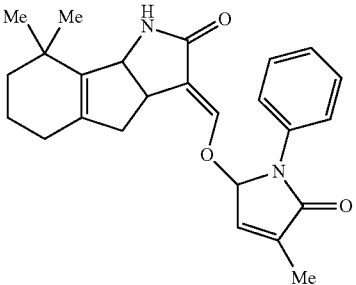

(Ib-16)

(3E)-8,8-dimethyl-3-[(4-methyl-5-oxo-1-phenyl-2H-pyrrol-2-yl)oxymethylene]-3a,4,5,6,7,8b-hexahydro-1H-indeno[1,2-b]pyrrol-2-one (compound Ib-16); LCMS (Method A): RT 1.08 min; ES+ 405 (M+H+); ¹H NMR (400 MHz, CDCl₃): δ ppm 0.95-1.05 (m, 6H), 1.31-1.45 (m, 2H), 1.56-1.68 (m, 2H), 1.71-1.90 (m, 2H), 1.96 (s, 3H), 2.00-2.22 (m, 1H), 2.42-2.70 (m, 1H), 3.36-3.56 (m, 1H), 4.44-4.61 (m, 1H), 5.71 (s, 1H), 6.06-6.22 (m, 1H), 6.59-6.71 (m, 1H), 6.99-7.11 (m, 1H), 7.15-7.23 (m, 1H), 7.33-7.43 (m, 2H), 7.54-7.62 (m, 2H).

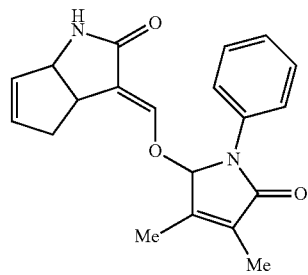
(Ib-17)

(3E)-3-[(3,4-dimethyl-5-oxo-1-phenyl-2H-pyrrol-2-yl)oxymethylene]-1,3a,4,6a-tetrahydrocyclopenta[b]pyrrol-2-one (compound Ib-17); LCMS (Method A): RT 0.85 min; ES+ 337 (M+H⁺); ¹H NMR (400 MHz, CDCl₃): δ ppm 1.92 (s, 3H), 1.97 (s, 3H), 2.05 (d, 0.5H), 2.29-2.39 (m, 0.5H), 2.62-2.91 (m, 1H), 3.47-3.69 (m, 1H), 4.57 (m, 1H), 5.56-5.85 (m, 2H), 5.96 (s, 1H), 6.22 (br. s., 1H), 6.97 (m, 1H), 7.12-7.22 (t, 1H), 7.31-7.42 (d, 2H), 7.51-7.63 (t, 2H).

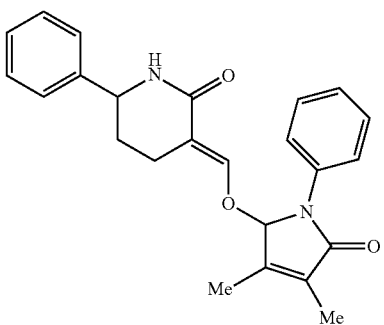
(Ib-18)

(3E)-3-[(3,4-dimethyl-5-oxo-1-phenyl-2H-pyrrol-2-yl)oxymethylene]-6-phenyl-piperidin-2-one (compound Ib-18); LCMS (Method A): RT 0.98 min; ES+ 389 (M+H⁺); ¹H NMR (400 MHz, CDCl₃): δ ppm 1.63-1.77 (m, 1H), 1.93 (s, 3H), 2.00 (s, 3H), 2.00-2.09 (m, 1H), 2.21-2.38 (m, 1H), 2.51-2.65 (m, 1H), 4.50 (dt, 1H), 5.65 (s, 1H), 5.95 (s, 1H), 7.13-7.21 (m, 1H), 7.22-7.41 (m, 8H), 7.52-7.62 (m, 2H).

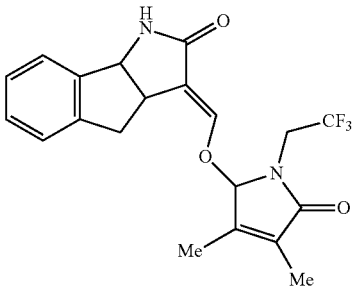
(Ib-19)

(3E)-3-[[3,4-dimethyl-5-oxo-1-(2,2,2-trifluoroethyl)-2H-pyrrol-2-yl]oxymethylene]-1,3a,4,8b-tetrahydroindeno[1,2-b]pyrrol-2-one (compound Ib-19); LCMS (Method A): RT 0.91 min; ES+ 393 (M+H⁺); ¹H NMR (400 MHz, CDCl₃): δ ppm 1.89 (s, 3H), 1.96 (s, 3H), 2.99-3.14 (m, 1H), 3.43-3.69 (m, 2H), 3.88-4.00 (m, 1H), 4.24-4.42 (m, 1H), 5.06-5.19 (m, 1H), 5.60 (br. s., 1H), 6.91 (br. s., 1H), 6.97 (d, 1H) 7.19-7.40 (m, 4H).

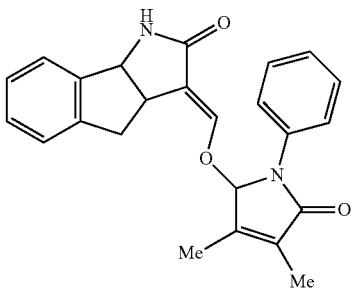
(Ib-20)

(3E)-3-[(4-methyl-5-oxo-1-(3,5-bistrifluoromethyl-phenyl)-2H-pyrrol-2-yl)oxymethylene]-1,3a,4,8b-tetrahydroindeno[1,2-b]pyrrol-2-one (compound Ib-20); LCMS (Method B): RT 1.46 min, ES+ 776 [2(M+H⁺)]. ¹H NMR (400 MHz, CDCl₃): δ ppm 1.93 and 1.95 (s, 3H), 2.01 and 2.02 (s, 3H), 2.58 and 2.95 (dd, 1H), 3.26 and 3.42 (dd, 1H), 3.74-3.81 and 3.82-3.89 (m, 1H), 5.02 and 5.05 (d, 1H), 5.98 and 6.03 (s, 1H), 6.31 (s, 1H), 6.98-7.07 (m, 1H), 7.14-7.29 (m, 4H), 7.35-7.43 (m, 2H), 7.54-7.63 (m, 2H).

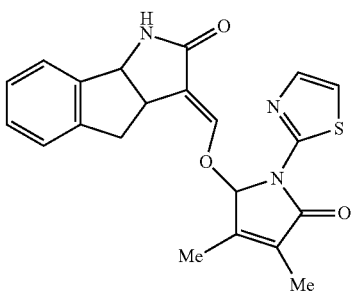
(Ib-24)

(3E)-3-[(3,4-dimethyl-5-oxo-1-thiazol-2-yl-2H-pyrrol-2-yl)oxymethylene]-1,3a,4,8b-tetrahydroindeno[1,2-b]pyrrol-2-one (compound Ib-24); LCMS (Method B): RT 1.42 min, ES+ 394 (M+H⁺). ¹H NMR (400 MHz, CDCl₃): δ ppm 1.95 and 1.97 (s, 3H), 2.06 and 2.07 (s, 3H), 2.94 and 3.03 (dd, 1H), 3.34-3.50 (m, 1H), 3.86-3.96 (m, 1H), 5.05 and 5.07

(bs, 1H), 6.27-6.31 (m, 1H), 6.52-6.59 (m, 1H), 6.99 (dd, 1H), 7.11-7.29 (m, 3H), 7.36-7.54 (m, 2H).

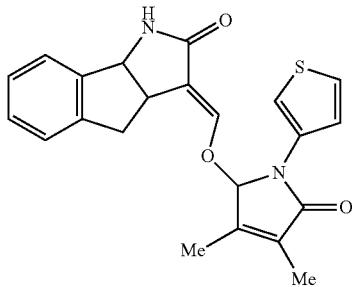

(Ib-25)

(3E)-3-[[3,4-dimethyl-5-oxo-1-(3-thienyl)-2H-pyrrol-2-yl]oxymethylene]-1,3a,4,8b-tetrahydroindeno[1,2-b]pyrrol-2-one (compound Ib-25); LCMS (Method A): RT 0.94 min, ES+ 393 (M+H+); RT 0.95 min, ES+ 393 (M+H+). $^1$H NMR (400 MHz, CDCl$_3$): δ ppm 1.92 and 1.94 (s, 3H), 2.00 (s, 3H), 2.86 and 3.05 (dd, 1H), 3.39-3.54 (m, 1H), 3.85-3.98 (s, 1H), 5.08 (m, 1H), 5.87 (d, 1H), 6.08 (bs, 1H), 7.01 (dd, 1H), 7.13-7.48 (m, 6H).

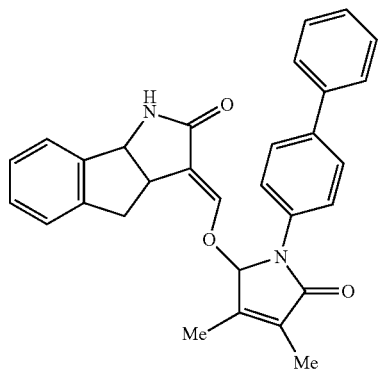

(Ib-26)

(3E)-3-[(3,4-dimethyl-5-oxo-1-(4-phenylphenyl)-2H-pyrrol-2-yl)oxymethylene]-1,3a,4,8b-tetrahydroindeno[1,2-b]pyrrol-2-one (compound Ib-26); LCMS (Method A): RT 1.09 min, ES+ 463 (M+H+). $^1$H NMR (400 MHz, CDCl$_3$): δ ppm 1.94 and 1.96 (bs, 3H), 2.03 and 2.04 (bs, 3H), 2.62 and 2.98 (dd, 1H), 3.27 and 3.43 (dd, 1H), 3.78-3.90 (m, 1H), 5.04 (t, 1H), 6.02 and 6.07 (bs, 1H), 6.42 (bs, 1H), 6.90-7.86 (m, 13H).

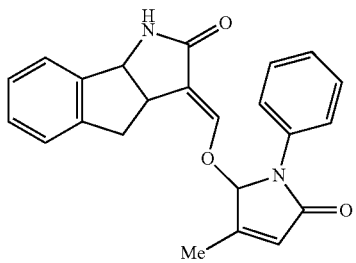

(Ib-27)

(3E)-3-[(3-methyl-5-oxo-1-phenyl-2H-pyrrol-2-yl)oxymethylene]-1,3a,4,8b-tetrahydroindeno[1,2-b]pyrrol-2-one (compound Ib-27); LCMS (Method A): RT 0.89 min, ES+ 373 (M+H+). $^1$H NMR (400 MHz, CDCl$_3$): δ ppm 2.11-2.13 (m, 3H), 2.60 and 2.94 (dd, 1H), 3.28 and 3.42 (dd, 1H), 3.75-3.90 (m, 1H), 5.04 (dd, 1H), 6.04 and 6.09 (s, 1H), 6.12 (bs, 1H), 7.02-7.30 (m, 6H), 7.36-7.44 (m, 2H), 7.51-7.58 (m, 2H).

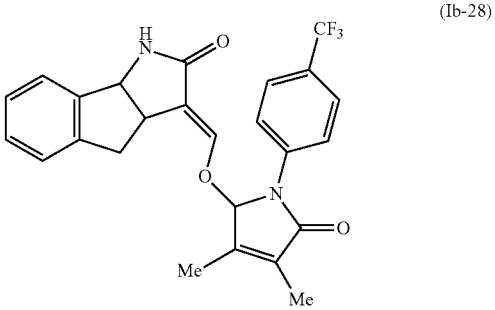 [SMILES: CC1=C(C)C(O/C=C2/C(=O)NC3c4ccccc4CC23)N(c2ccc(C(F)(F)F)cc2)C1=O]

(Ib-28)

(3E)-3-[(3,4-dimethyl-5-oxo-1-(4-trifluoromethyl-phenyl)-2H-pyrrol-2-yl)oxymethylene]-1,3a,4,8b-tetrahydroindeno[1,2-b]pyrrol-2-one (compound Ib-28); LCMS (Method A): RT 1.06 min, ES+ 455 (M+H+). $^1$H NMR (400 MHz, CDCl$_3$): δ ppm 1.94 and 1.99 (s, 3H), 2.03 and 2.04 (s, 3H), 2.56 (dd, 0.5H), 2.98 (dd, 0.5H), 3.26-3.50 (m, 1H), 3.73-3.91 (m, 1H), 5.04 (m, 1H), 6.06 and 6.11 (s, 1H), 6.30 (s, 1H), 6.94 and 7.02 (s, 1H), 7.12-7.31 (m, 4H) 7.53-7.72 (m, 2H) 7.82 (m, 2H).

(Ib-29)

(3E)-3-[(3,4-dimethyl-5-oxo-1-(3-trifluoromethyl-phenyl)-2H-pyrrol-2-yl)oxymethylene]-1,3a,4,8b-tetrahydroindeno[1,2-b]pyrrol-2-one (compound Ib-29); LCMS (Method A): RT 1.04 min, ES+ 455 (M+H+). $^1$H NMR (400 MHz, CDCl$_3$): δ ppm 1.94 and 1.95 (s, 3H), 2.03 and 2.04 (s, 3H), 2.60 (dd, 0.5H), 2.99 (dd, 0.5H), 3.31-3.52 (m, 1H), 3.72-3.93 (m, 1H), 5.02 and 5.06 (d, 1H) 6.03 and 6.09 (s, 1H), 6.69 (s, 1H), 6.92 and 6.99 (s, 1H), 7.12-7.30 (m, 4H), 7.38-7.55 (m, 2H), 7.79 (s, 0.5H), 7.93 (d, 0.5H), 7.95 (s, 1H) 8.12 (d, 0.5H)

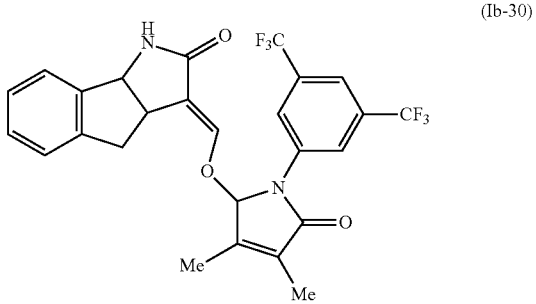 [SMILES: CC1=C(C)C(O/C=C2/C(=O)NC3c4ccccc4CC23)N(c2cc(C(F)(F)F)cc(C(F)(F)F)c2)C1=O]

(Ib-30)

(3E)-3-[(3,4-dimethyl-5-oxo-1-[3,4-bis(trifluoromethyl) phenyl]-2H-pyrrol-2-yl)oxymethylene]-1,3a,4,8b-tetrahydroindeno[1,2-b]pyrrol-2-one (compound Ib-30); LCMS (Method A): RT 1.15 min, ES– 521 (M–H$^+$). $^1$H NMR (400 MHz, CDCl$_3$): δ ppm 1.96 and 1.98 (s, 3H), 2.07 (s, 3H), 2.70 (dd, 0.5H), 3.07 (dd, 0.5H), 3.37-3.59 (m, 1H), 3.70-3.83 (m, 0.5H), 3.86-4.00 (m, 0.5H), 5.04 (d, 0.5H), 5.10 (d, 0.5H), 6.10 and 6.14 (s, 1H), 6.53 (s, 1H), 6.91-6.94 (m, 1H), 7.03-7.32 (m, 4H), 7.67 (s, 1H), 8.31 (s, 1H), 8.33 (s, 1H).

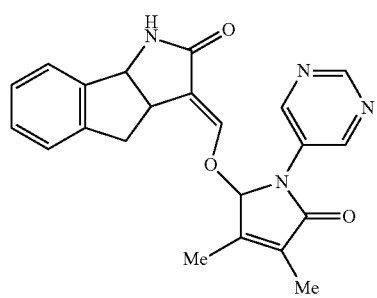

(Ib-31)

((3E)-3-[(3,4-dimethyl-5-oxo-1-pyrimidin-5-yl-2H-pyrrol-2-yl)oxymethylene]-1,3a,4,8b-tetrahydroindeno[1,2-b] pyrrol-2-one (compound Ib-31); LCMS (Method A): RT 0.77 min, ES+ 389 (M–H$^+$).

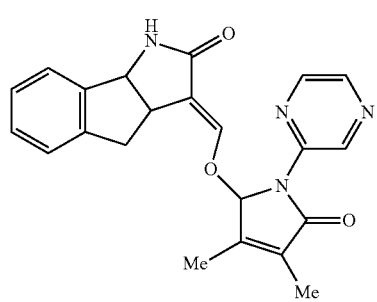

(Ib-32)

(3E)-3-[(3,4-dimethyl-5-oxo-1-pyrazin-2-yl-2H-pyrrol-2-yl)oxymethylene]-1,3a,4,8b-tetrahydroindeno[1,2-b]pyrrol-2-one (compound Ib-32); LCMS (Method A): RT 0.86 min, ES+ 389 (M–H$^+$).

Example P2-2

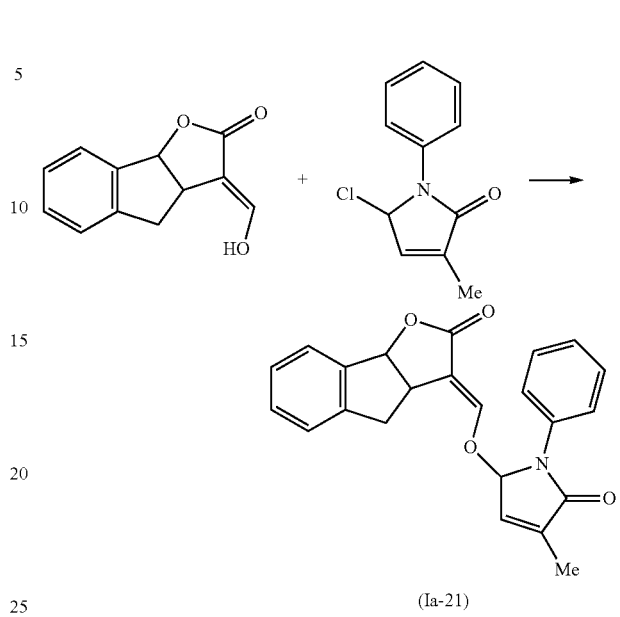

(Ia-21)

A solution of 3-(hydroxymethylidene)-3,3a,4,8b-tetrahydro-2H-indeno[1,2-b]furan-2-one (1.13 g, 5.59 mmol in 1,2-dimethoxyethane (60 mL)) under argon was cooled to 0° C. and potassium tert-butylate (0.63 g, 5.59 mmol) was added. After stirring for 10 minutes at 0° C., a solution of 2-chloro-4-methyl-1-phenyl-2H-pyrrol-5-one (compound III-2) (1.16 g, 5.59 mmol) in 1,2-dimethoxyethane (10 mL) was added and the reaction mixture was stirred at room temperature for 16 h. Water and ethyl acetate were added and the aqueous layer was extracted with ethyl acetate. The combined organic layers were washed with brine, dried over Na$_2$SO$_4$ and the solvent was evaporated. The residue was purified by preparative HPLC to give 3-methyl-5-{[(E)-(2-oxo-4,8b-dihydro-2H-indeno[1,2-b]furan-3(3a H)-ylidene)methyl]oxy}-1-phenyl-1,5-dihydro-2H-pyrrol-2-one Ia-21 as a white solid and a 1.2/1 mixture of diastereoisomers (0.378 g, 18%); LCMS (method A): RT 0.99 min; ES+ 374 (M+H$^+$); $^1$H NMR (400 MHz, CDCl$_3$): δ ppm 2.05 and 2.07 (t, 3H), 2.58 and 2.95 (dd, 1H), 3.22 and 3.35 (dd, 1H), 3.76-3.89 (m, 1H), 5.88 (t, 1H), 6.21 and 6.28 (m, 1H), 6.69 (m, 1H), 7.01-7.35 (m, 5H), 7.38-7.49 (m, 3H), 7.55 (m, 2H).

A similar procedure was used to prepare the following compounds:

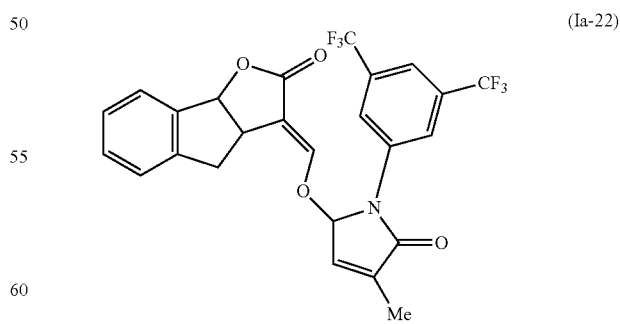

(Ia-22)

1-[3,5-bis(trifluoromethyl)phenyl]-4-methyl-2-[(E)-(2-oxo-4,8b-dihydro-3aH-indeno[1,2-b]furan-3-ylidene) methoxy]-2H-pyrrol-5-one (compound Ia-22); LCMS (Method A): RT 1.16 min, ES+ 510 (M+H$^+$); RT 1.17 min, ES+ 510 (M+H$^+$); $^1$H NMR (400 MHz, CDCl$_3$): δ ppm 2.08 and 2.10 (bs, 3H), 2.70 and 3.05 (dd, 1H), 3.35-3.50 (m, 1H), 3.75-3.83 and 3.88-3.98 (m, 1H), 5.90 and 5.93 (d, 1H), 6.33 and 6.39 (bs, 1H), 6.77-6.81 (m, 1H), 7.04-7.37 (m, 4H), 7.46 (dd, 1H), 7.72 (bs, 1H), 8.27 and 8.30 (bs, 2H).

(Ia-23)

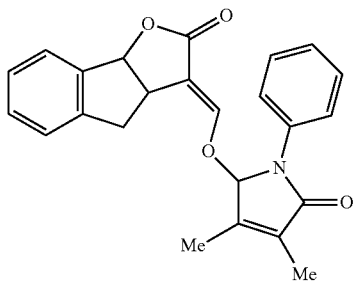

3,4-dimethyl-5-{[(E)-(2-oxo-4,8b-dihydro-2H-indeno[1,2-b]furan-3(3aH) ylidene)methyl]oxy}-1-phenyl-1,5-dihydro-2H-pyrrol-2-one (compound Ia-23); LCMS (Method B): RT 1.64 min, ES+ 388 (M+H$^+$); $^1$H NMR (400 MHz, CDCl$_3$): δ ppm 1.94 and 1.96 (m, 3H), 2.01 and 2.03 (m, 3H), 2.60 and 2.97 (dd, 1H), 3.26 and 3.40 (dd, 1H), 3.79-3.92 (m, 1H), 5.88 (t, 1H), 6.03 and 6.08 (bs, 1H), 7.02-7.59 (m, 10H).

Tables 2, 3 and 4 below provide physical data for compounds of formula (I) according to the invention made analogously by the methodology described above.

TABLE 2

Compounds of Formula (IA) and ring system A, wherein Y$_1$ is NR$^5$: Y$_2$, R$^5$, X$^3$ and X$^4$ are as defined.

(IA)

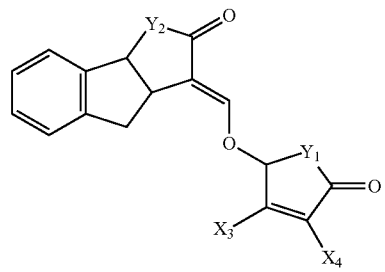

| Compound | Y$_2$ | R$^5$ | X$_3$ | X$_4$ | LCMS method | Retention (min.) | Mass |
|---|---|---|---|---|---|---|---|
| Ib-1 | NH | CH$_2$OMe | H | Me | A | 0.81 | 353 (M + Na$^+$) |
| Ib-2 | NH | Ph | H | Me | A | 0.92 | 373 (M + H$^+$) |
| Ib-3 | NH | OMe | H | Me | A | 0.82 | 327 (M + H$^+$) |
| Ib-6 | NH | CH$_2$CCH | H | Me | A | 0.84 | 335 (M + H$^+$) |
| Ib-7 | NH | CH$_2$CF$_3$ | H | Me | A | 0.90 | 379 (M + H$^+$) |
| Ib-5 | NH | CH(CH$_2$CH$_2$) | H | Me | A | 0.83 | 337 (M + H$^+$) |
| Ib-4 | NH | Bn | H | Me | A | 0.93 | 387 (M + H$^+$) |
| Ia-1 | NBoc | CH$_2$OMe | H | Me | A | 1.07 | 441 (M + H$^+$) |
| Ia-2 | NBoc | Ph | H | Me | A | 1.14 | 472 (M + H$^+$) |
| Ia-3 | NBoc | OMe | H | Me | A | 1.06 | 490 (M + MeCN + Na$^+$) |
| Ia-6 | NBoc | CH$_2$CCH | H | Me | A | 1.08 | 435 (M + H$^+$) |
| Ia-7 | NBoc | CH$_2$CF$_3$ | H | Me | A | 1.14 | 479 (M + H$^+$) |
| Ia-5 | NBoc | CH(CH$_2$CH$_2$) | H | Me | A | 1.09 | 437 (M + H$^+$) |
| Ia-19 | NBoc | CH$_2$CF$_3$ | Me | Me | A | 1.14 | 479 (M + H$^+$) |
| Ib-19 | NH | CH$_2$CF$_3$ | Me | Me | A | 0.91 | 393 (M + H$^+$) |
| Ia-8 | NBoc | (4-F)Ph | H | Me | B | 1.94 | 491 (M + H$^+$) |
| Ib-8 | NH | (4-F)Ph | H | Me | A | 0.93 | 391 (M + Hl$^+$) |
| Ia-9 | NBoc | (3-F)Ph | H | Me | A | 1.15 | 490 (M + H$^+$) |
| Ib-9 | NH | (3-F)Ph | H | Me | A | 0.93/0.94 | 782 [2(M + H$^+$)] |
| Ia-10 | NBoc | (2-F)Ph | H | Me | A | 1.12 | 491 (M + H$^+$) |
| Ib-10 | NH | (2-F)Ph | H | Me | B | 1.35 | 782 [2(M + H$^+$)] |
| Ia-11 | NBoc | (3,5-F)Ph | H | Me | B | 2.00/2.03 | 509 (M + H$^+$) |
| Ib-11 | NH | (3,5-F)Ph | H | Me | A | 0.96/0.98 | 818 [2(M + H$^+$)] |

TABLE 2-continued

Compounds of Formula (IA) and ring system A, wherein $Y_1$ is $NR^5$: $Y_2$, $R^5$, $X^3$ and $X^4$ are as defined.

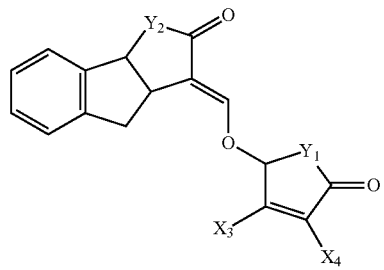

(IA)

| Compound | $Y_2$ | $R^5$ | $X_3$ | $X_4$ | LCMS method | Retention (min.) | Mass |
|---|---|---|---|---|---|---|---|
| Ia-12 | NBoc | (2,6-F)Ph | H | Me | A | 1.12 | 509 (M + H$^+$) |
| Ib-12 | NH | (2,6-F)Ph | H | Me | A | 0.91 | 818 [2(M + H$^+$)] |
| Ia-13 | NBoc | (3,5-CF$_3$)Ph | H | Me | A | 1.29 | 607 (M + H$^+$) |
| Ib-13 | NH | (3,5-CF$_3$)Ph | H | Me | A | 1.09/1.10 | 509 (M + H$^+$) |
| Ia-20 | NBoc | Ph | Me | Me | B | 1.96 | 497 (M + H$^+$) |
| Ib-20 | NH | Ph | Me | Me | B | 1.46 | 776 [2(M + H$^+$)] |
| Ia-21 | O | Ph | H | Me | A | 0.99 | 374 (M + H$^+$) |
| Ia-22 | O | (3,5-CF$_3$)Ph | H | Me | A | 1.16/1.17 | 510 (M + H$^+$) |
| Ia-23 | O | Ph | Me | Me | B | 1.64 | 388 (M + H$^+$) |
| Ia-24 | NBoc | -(2-thiazoyl) | Me | Me | B | 1.90 | 495 (M + H$^+$) |
| Ib-24 | NH | -(2-thiazoyl) | Me | Me | B | 1.42 | 394 (M + H$^+$) |
| Ia-25 | NBoc | -(3-thienyl) | Me | Me | A | 1.18 | 493 (M + H$^+$) |
| Ib-25 | NH | -(3-thienyl) | Me | Me | A | 0.94/0.95 | 393 (M + H$^+$) |
| Ia-26 | NBoc | (4-Ph)Ph | Me | Me | A | 1.28 | 563 (M + H$^+$) |
| Ib-26 | NH | (4-Ph)Ph | Me | Me | A | 1.09 | 463 (M + H$^+$) |
| Ia-27 | NBoc | Ph | Me | H | A | 1.12 | 471 (M + H$^+$) |
| Ib-27 | NH | Ph | Me | H | A | 0.89 | 373 (M + H$^+$) |
| Ia-28 | NBoc | (4-CF$_3$)Ph | Me | Me | A | 1.26 | 554 (M + H$^+$) |
| Ib-28 | NH | (4-CF$_3$)Ph | Me | Me | A | 1.06 | 455 (M + H$^+$) |
| Ia-29 | NBoc | (3-CF$_3$)Ph | Me | Me | A | 1.31 | 554 (M + H$^+$) |
| Ib-29 | NH | (3-CF$_3$)Ph | Me | Me | A | 1.04 | 455 (M + H$^+$) |
| Ia-30 | NBoc | (3,5-CF$_3$)Ph | Me | Me | A | 1.32 | 662 (M + H$^+$) |
| Ib-30 | NH | (3,5-CF$_3$)Ph | Me | Me | A | 1.15 | 521 (M + H$^+$) |
| Ia-31 | NBoc | 1-pyrimidin-5-yl | Me | Me | A | 1.09 | 489 (M + H$^+$) |
| Ib-31 | NH | 1-pyrimidin-5-yl | Me | Me | A | 0.77 | 389 (M + H$^+$) |
| Ia-32 | NBoc | 1-pyrazin-2-yl | Me | Me | A | 1.16 | 489 (M + H$^+$) |
| Ib-32 | NH | 1-pyrazin-2-yl | Me | Me | A | 0.86 | 389 (M + H$^+$) |

TABLE 3

Compounds of Formula (ID) and ring system D, wherein $Y_1$ is $NR^5$: $Y_2$, $R^5$, $X^3$ and $X^4$ are as defined.

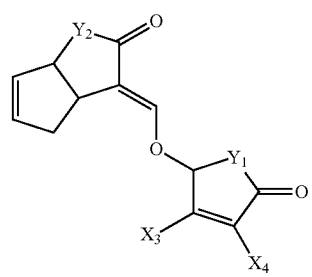

(ID)

| Compound | $Y_2$ | $R^5$ | $X_3$ | $X_4$ | LCMS method | Retention (min.) | Mass |
|---|---|---|---|---|---|---|---|
| Ia-17 | NBoc | Ph | Me | Me | A | 1.09 | 895 (2M + Na$^+$); |
| Ib-17 | NH | Ph | Me | Me | A | 0.85 | 337 (M + H$^+$) |

TABLE 4

Compounds of Formula (IF) and ring system F, wherein $Y_1$ is $NR^5$: $Y_2$, $R^5$, $X^3$ and $X^4$ are as defined.

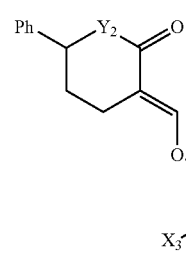

(IF)

| Compound | $Y_2$ | $R^5$ | $X_3$ | $X_4$ | LCMS method | Retention (min.) | Mass |
|---|---|---|---|---|---|---|---|
| Ia-8 | NBoc | Ph | H | Me | A | 1.13 | 475 (M + H$^+$) |
| Ia-18 | NBoc | Ph | Me | Me | A | 1.15 | 489 (M + H$^+$) |
| Ib-8 | NH | Ph | H | Me | A | 0.94 | 375 (M + H$^+$) |
| Ib-18 | NH | Ph | Me | Me | A | 0.98 | 389 (M + H$^+$) |

TABLE 5

Compounds of Formula (IV)

(IV)

| Compound | $X_3$ | $X_4$ | R5 | $^1$H NMR (400 MHz, CDCl$_3$) δ ppm |
|---|---|---|---|---|
| IV-1 | H | Me | CH$_2$OMe | 6.65 (1 H, s), 5.50 (1 H, d), 4.90 (1 H, d), 4.73 (1 H, d), 3.97 (1 H, d), 3.33 (3H, s), 1.90 (3 H, s) |
| IV-3 | H | Me | OMe | 6.47 (1 H, s), 5.47 (1 H, s), 3.93 (3 H, s), 1.91 (3 H, s). |
| IV-5 | H | Me | CH(CH$_2$CH$_2$) | 6.49 (1 H, s), 5.22 (1 H, brs), 3.61 (1H, brs), 2.61 (1 H, m), 1.83 (3 H, s), 1.01-0.66 (4 H, m). |
| IV-6 | H | Me | CH$_2$CCH | 6.65 (1 H, s), 5.52 (1 H, d), 4.53 (1 H, d), 4.02 (1 H, d), 2.27 (1 H, s), 2.20 (1 H, d), 1.94 (3 H, s). |
| IV-7 | H | Me | CH$_2$CF$_3$ | 6.69 (1 H, s), 5.48 (2 H, d), 4.25 (1 H, m), 3.82 (1 H, m), 2.50 (1 H, d), 1.94 (3 H, s) |
| IV-8 | Me | Me | CH$_2$CF$_3$ | 5.25 (d, 1H), 4.18 (dd, 1H), 3.71-3.83 (m, 1H), 3.47 (d, 1H), 2.00 (s, 3H), 1.78 (t, 3H) |
| IV-9 | H | Me | (4-F)—Ph | 7.64-7.68 (m, 2H), 7.02-7.09 (m, 2H), 6.66 (m, 1H), 5.78 (m, 1H), 2.83 (d, 1H), 1.89 (m, 3H) |
| IV-10 | H | Me | (3-F)—Ph | 7.66 (dt, 1H), 7.53 (dd, 1H), 7.32-7.41 (m, 1H), 6.89 (td, 1H), 6.73 (bt, 1H), 5.88 (bs, 1H), 2.47-2.63 (m, 1H), 1.93 (m, 3H) |
| IV-11 | H | Me | (2-F)—Ph | 7.45 (td, 1H), 7.13-7.33 (m, 3H), 6.71 (bt, 1H), 5.85 (bd, 1H), 2.52 (bd, 1H), 1.98 (bt, 3H) |
| IV-12 | H | Me | (3,5-F)—Ph | 7.38-7.46 (m, 2H), 6.69-6.73 (m, 1H), 6.59 (tt, 1H), 5.77 (bs, 1H), 3.10 (bs, 1H), 1.86 (bt, 3H) |
| IV-13 | H | Me | (2,6-F)—Ph | 7.32 (m, 1H), 7.00 (t, 2H), 6.76 (m, 1H), 5.70 (bs, 1H), 2.33 (bs, 1H), 1.99 (bs, 3H) |
| IV-14 | H | Me | (3,5-CF$_3$)—Ph | 8.29 (bs, 2H), 7.61 (bs, 1H), 6.75 (m, 1H), 5.89 (bd, 1H), 3.45 (bd, 1H), 1.81 (bs, 3H) |
| IV-15 | Me | Me | -(3-thienyl) | 7.52 (dd, 1H), 7.48 (dd, 1H), 7.27 (dd, 1H), 5.46 (d, 1H), 3.11 (d, 1H), 2.01 (s, 3H), 1.60 (s, 3H) |
| IV-16 | Me | Me | 1-pyrimidin | 1.92 (m, 3 H), 2.11 (s, 3 H), 5.70 (s, 1 H), 8.97 (s, 1 H), 9.24 (s, 2 H). |

Biological Examples

A. *Orobanche* Seed Germination

The effect of the compounds of Formula (I) on the germination of *Orobanche cumana* Wallr. seeds was evaluated on glass fibre filter paper (GFFP) in petri dishes. Seeds were pre-conditioned at moisture and suitable temperature to become responsive to the specific chemical germination stimulants.

Test compounds were dissolved in DMSO (10 000 mgl$^{-1}$) and stored at room temperature in a desiccator with desiccants. The stock solutions were dissolved with sterile deionised water to the appropriate final test concentration.

Seeds of *O. cumana* race 'F' were collected from sunflower fields in Manzanilla (Seville, Spain) in 2008 (seed lot IN153) and stored at room temperature. To separate seeds from heavy organic debris, a modified sucrose floatation technique as described by Hartman & Tanimonure (*Plant Disease* (1991), 75, 494) was applied. Seeds were filled into a separation funnel and stirred in water. When seeds floated to the surface, the water fraction containing heavy debris was discarded. Seeds were re-suspended in 2.5 M sucrose solution (specific gravity of 1.20) and heavy debris was allowed to settle down for 60 minutes. After removing debris, seeds were disinfected in 1% sodium hypochlorite solution and 0.025% (v/v) Tween 20 for 2 minutes. The seeds were decanted onto two layers of cheese cloth, rinsed with sterile deionised water and re-suspended in sterile deionised water. 2 mL of the seed suspension containing approximately 150 to 400 seeds was spread evenly on two layers of sterile glass fiber filter paper disc (Ø9 mm) in Petri dishes (Ø cm). After wetting the discs with 3 mL sterile deionised water, petri dishes were sealed with parafilm. Seeds were incubated for 10 days at 20° C. in the dark for seed conditioning. The upper disc with conditioned seeds was briefly dried, transferred to a petri dish lined with a dry GFFP disc, and wetted with 6 mL of the appropriate test solution. The compounds of Formula (I) were tested at concentrations of 0.01, 0.1, and 1 mg/L. The strigolactone analogue GR24 (commercially available as a mixture of isomers) was included as positive control and 0.01% DMSO as negative control. All treatments were tested in five replicates. Seeds were re-incubated at 20° C. in the dark and examined for germination 10 days later.

The radicles of germinated seeds were stained for 5 minutes with blue ink (PELIKAN #4001, Germany) in 5% acetic acid according to Long et al (Seed Science Research (2008), 18, 125). After staining, seeds were photographed using a camera stand mounted with a digital SLR camera (Canon EOS 5D). Germination of 100 seeds per replicate was evaluated on digital images. Seeds were considered germinated when the radicle protruded from the seed coat.

The results of the *Orobanche* seed germination tests are shown in Table 6.

TABLE 6

Effect of strigolactone analogs on germination of preconditioned *Orobanche cumana* seeds at 1 mg/L

| | Germination (%)* | |
|---|---|---|
| Compound | 0.1 mg/L | 0.01 mg/L |
| Ib-5 | 73 | 68 |
| Ib-7 | 26 | 46 |
| Ia-7 | 8 | 34 |

*N = 5 x 100 seeds; control (0.01% DMSO): 0.75% germination

B. Corn Seed Germination

The effect of compounds of Formula (I) on the germination of NK Falkone corn seeds under cold stress was evaluated as follows.

NK Falkone corn seeds were sorted by size using 2 sieves, one excluding very big seeds and the other with round holes of 8 to 9 mm diameter. The seeds retained by the latter sieve are used for the germination test.

The corn seeds were placed in 24 well plates (each plate is considered as one experimental unit or replicate). Germination is initiated by the addition of 250 µl of distilled water containing 0.5% DMSO per well as a mean for compound solubilization. 8 replicates (ie, 8 plates) were used for each treatment characterization. Plates were sealed using seal foil (Polyolefin Art. Nr. 900320) from HJ-BIOANALYTIK. All plates were placed horizontally on trolleys in a climatic chamber at 15° C. or 23° C. in complete darkness. The experiment is laid out in a completely randomized design in climatic chamber with 75% Relative Humidity. Foils are pierced, one hole per well using a syringe after 72 hours for experiments performed at 15° C. and after 24 hours for experiments performed at 23° C.

Germination is followed over time by taking photographs at different time points. Image analysis is done automatically with a macro developed using the Image J software. A dynamic analysis of germination is carried out by fitting a logistic curve to the relationship between % germination and time for each plate (T50 parameter).

T50 is the time needed for half the seed population to be germinated. A negative value of T50 represents a faster germination rate. The mean of T50 parameters is calculated for the 8 replicates and the kinetic parameter is determined for each germination curve. Data in bold indicate germination enhancing statistically significant differences between treated seeds and control (empty vehicle treated) T50 values (P<0.05) as outlined in Table 7.

TABLE 7

Effect of strigolactone analogs on germination of corn seeds under cold stress condition (15° C.) at various concentrations.

| Compound | Rate (μM)[a] | T50 (% vs control)[b] |
|---|---|---|
| GR-24 | 0.08 | 0.1 |
|  | 0.4 | −2 |
|  | 2 | −0.6 |
|  | 10 | −2.4 |
| Ib-3 | 2 | −4.0 |
|  | 10 | 3.4 |
|  | 50 | −3.8 |
|  | 250 | −5.5 |
| Ib-5 | 2 | −0.8 |
|  | 10 | −4.3 |
|  | 50 | −3.9 |
|  | 250 | −5.8 |
| Ib-2 | 0.4 | −0.4 |
|  | 2 | −2.5 |
|  | 10 | −6.1 |
|  | 50 | −6.2 |
| Ib-7 | 2 | 1.5 |
|  | 10 | −3.0 |
|  | 50 | −3.3 |
|  | 250 | −4.5 |
| Ib-8 | 1 | −2.6 |
|  | 5 | −2.8 |
|  | 25 | 2.0 |
|  | 125 | −2.3 |
| Ib-13 | 0.2 | 1.0 |
|  | 1 | −3.6 |
|  | 5 | −3.6 |
|  | 25 | −2.7 |
| Ib-9 | 0.2 | −0.8 |
|  | 1 | −4.8 |
|  | 5 | −5.6 |
|  | 25 | −5.2 |
| Ib-20 | 0.4 | 1.2 |
|  | 2 | −3.1 |
|  | 10 | −3.2 |
|  | 50 | −3.1 |

[a]Concentration in compound (I) in 250 μl distilled water containing 0.5% DMSO
[b]Control = 250 μl distilled water containing 0.5% DMSO

The invention claimed is:
1. A compound of formula (I)

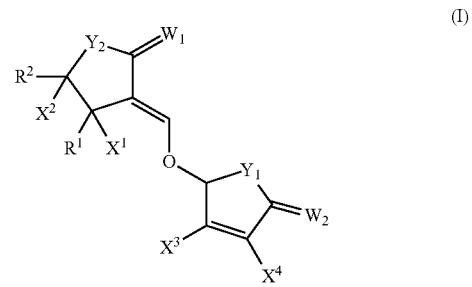

wherein
$W^1$ and $W^2$ are each independently O or S;
$R^1$ and $R^2$ are each independently hydrogen, halogen, nitro, hydroxyl, cyano, substituted or unsubstituted $C_1$-$C_6$alkyl, substituted or unsubstituted $C_1$-$C_6$alkoxy, substituted or unsubstituted aryl, or substituted or unsubstituted heteroaryl; or
$R^1$ and $R^2$ together with the carbon atoms to which they are joined form a saturated or unsaturated, aromatic or non-aromatic, substituted or unsubstituted 3-7-membered carbocycle; or,
$R^1$ and $R^2$ together with the carbon atoms to which they are joined form a saturated or unsaturated, aromatic or non-aromatic, substituted or unsubstituted 4-7-membered carbocycle fused to another saturated or unsaturated, aromatic or non-aromatic, substituted or unsubstituted 3-7-membered carbocycle or heterocycle;
$X_1$ and $X_2$ are independently hydrogen, $C_1$-$C_6$alkyl, $C_1$-$C_6$haloalkyl, halogen, $C_1$-$C_6$alkoxy, cyano, nitro, $C_1$-$C_6$alkylsulfinyl, $C_1$-$C_6$alkylsulfonyl or $C_1$-$C_6$alkylthio;
$Y_2$ is oxygen, or —$(CR^4R^7)_p(CR^3R^8)_nN(R^6)$—, wherein n is 0 or 1, and p is 0 or 1;
$R^3$ and $R^4$ are each independently hydrogen, halogen, nitro, hydroxyl, cyano, substituted or unsubstituted $C_1$-$C_6$alkyl, substituted or unsubstituted $C_1$-$C_6$alkoxy, substituted or unsubstituted aryl, or substituted or unsubstituted heteroaryl; or,
$R^3$ and $R^4$ together with the carbon atoms to which they are joined form a saturated or unsaturated, non-aromatic, substituted or unsubstituted 3-7-membered carbocycle; or
$R^3$ and $R^4$ together with the carbon atoms to which they are joined form a saturated or unsaturated, aromatic or non-aromatic, substituted or unsubstituted 4-7-membered carbocycle fused to another saturated or unsaturated, aromatic or non-aromatic, substituted or unsubstituted 3-7-membered carbocycle; or
$R^2$ and $R^3$ together with the carbon atoms to which they are joined form (i) a saturated or unsaturated, non-aromatic, substituted or unsubstituted 3-7-membered carbocycle, or (ii) a saturated or unsaturated, aromatic or non-aromatic, substituted or unsubstituted 4-7-membered carbocycle fused to another saturated or unsaturated, aromatic or non-aromatic, substituted or unsubstituted 3-7-membered carbocycle;
$R^7$ and $R^8$ are each independently selected from hydrogen, $C_1$-$C_6$ alkyl, $C_1$-$C_6$ haloalkyl, halogen, $C_1$-$C_6$ alkoxy, aryloxy, $C_1$-$C_6$ alkylsulfinyl, $C_1$-$C_6$ alkylsulfonyl, $C_1$-$C_6$ alkylthio;

$Y_1$ is S or $NR^5$;

$R^5$ and $R^6$ are each independently hydrogen, $C_1$-$C_6$ alkoxy, hydroxyl, amine, N—$C_1$-$C_6$ alkylamine, N,N-di-$C_1$-$C_6$ alkylamine, substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_2$-$C_6$ alkynyl, substituted or unsubstituted $C_1$-$C_8$ alkylcarbonyl, substituted or unsubstituted $C_1$-$C_8$ alkoxycarbonyl, substituted or unsubstituted aryl, substituted or unsubstituted heteroaryl, substituted or unsubstituted heterocyclyl, substituted or unsubstituted benzyl; and $X^3$ and $X^4$ are each independently selected from hydrogen, $C_1$-$C_6$ alkyl, $C_2$-$C_3$ alkynyl, $C_1$-$C_6$ haloalkyl, halogen, $C_1$-$C_6$ alkoxy, $C_1$-$C_6$ alkylsulfinyl, $C_1$-$C_6$ alkylsulfonyl, $C_1$-$C_6$ alkylthio; or $X^3$ and $X^4$ together with the carbon atoms to which they are attached form a $C_5$- or $C_6$-cycloalkyl;

or an agrochemically acceptable salt or N-oxide thereof.

2. The compound according to claim 1, wherein $W_1$ is O and $W_2$ is O.

3. The compound according to claim 1, wherein $R^1$, $R^2$ and $R^3$ are each independently hydrogen, substituted or unsubstituted $C_1$-$C_6$alkyl, substituted or unsubstituted $C_1$-$C_6$haloalkyl, substituted or unsubstituted aryl, substituted or unsubstituted heteroaryl; or, $R^1$ and $R^2$, or $R^2$ and $R^3$, together with the carbon atoms to which they are joined form a substituted or unsubstituted, saturated or unsaturated, 5-6-membered carbocycle; or $R^1$ and $R^2$, or $R^2$ and $R^3$, together with the carbon atoms to which they are joined form a substituted or unsubstituted, saturated or unsaturated 5-6-membered carbocycle fused to a further unsaturated aromatic or non-aromatic, substituted or unsubstituted 5-6-membered carbocycle or heterocycle.

4. The compound according to claim 1, which is Formula (IA)

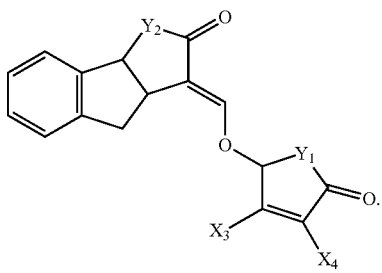

(IA)

5. The compound according to claim 1, wherein $Y_2$ is —$N(R^6)$—.

6. The compound according to claim 1, wherein $R^6$ is hydrogen, substituted or unsubstituted $C_1$-$C_6$ alkyl, $C_1$-$C_8$ alkylcarbonyl, $C_1$-$C_8$ alkoxycarbonyl, substituted or unsubstituted aryl, substituted or unsubstituted heteroaryl.

7. The compound according to claim 1, wherein $X_3$ and $X_4$ are each independently selected from hydrogen, $C_1$-$C_3$ alkyl, $C_1$-$C_3$alkoxy, and halogen.

8. The compound according to claim 1, wherein $Y_1$ is $NR^5$.

9. The compound according to claim 1, wherein $R^5$ is hydrogen, substituted or unsubstituted $C_1$-$C_3$alkyl, $C_3$-$C_6$ cycloalkyl, $C_1$-$C_3$ alkoxy, substituted or unsubstituted phenyl, or substituted or unsubstituted benzyl.

10. A plant growth regulating or seed germination promoting composition, comprising a compound according to claim 1, and an agriculturally acceptable formulation adjuvant.

11. A method for regulating the growth of plants at a locus, said method comprising applying to the locus a compound according to claim 1.

12. A method for promoting the germination of seeds, comprising applying to the seeds, or a locus containing the seeds, a compound according to claim 1.

13. A method for controlling weeds comprising applying to a locus containing weed seeds, a compound according to claim 1, allowing the weed seeds to germinate, and then applying to the locus a post-emergence herbicide.

* * * * *